(12) United States Patent
Houser et al.

(10) Patent No.: US 6,361,559 B1
(45) Date of Patent: *Mar. 26, 2002

(54) THERMAL SECURING ANASTOMOSIS SYSTEMS

(75) Inventors: Russell A. Houser, Livermore; James G. Whayne, San Jose; Sidney D. Fleischman, Menlo Park, all of CA (US)

(73) Assignee: Converge Medical, Inc., Pleasanton, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/329,504

(22) Filed: Jun. 10, 1999

Related U.S. Application Data

(60) Provisional application No. 60/111,948, filed on Dec. 11, 1998, and provisional application No. 60/088,705, filed on Jun. 10, 1998.

(51) Int. Cl.⁷ .................................................. A61F 2/00
(52) U.S. Cl. ...................................... 623/1.36; 606/213
(58) Field of Search ...................... 623/1.36; 606/213, 606/153, 154, 155

(56) References Cited

U.S. PATENT DOCUMENTS

| 4,214,587 A | 7/1980 | Sakura, Jr. |
| 4,366,819 A | 1/1983 | Kaster |
| 4,368,736 A | 1/1983 | Kaster |
| 4,607,637 A | 8/1986 | Berggren et al. |
| 4,624,257 A | 11/1986 | Berggren et al. |
| 4,657,019 A | 4/1987 | Walsh et al. |
| 4,665,906 A | 5/1987 | Jervis |
| 4,787,386 A | 11/1988 | Walsh et al. |
| 4,917,087 A | 4/1990 | Walsh et al. |
| 4,917,090 A | 4/1990 | Berggren et al. |
| 4,917,091 A | 4/1990 | Berggren et al. |

(List continued on next page.)

FOREIGN PATENT DOCUMENTS

| WO | WO 96/22745 | 8/1996 |
| WO | WO 97/13463 A1 | 4/1997 |
| WO | WO 97/13471 A1 | 4/1997 |
| WO | WO 97/16122 A1 | 5/1997 |
| WO | WO 97/27893 A1 | 8/1997 |
| WO | WO 97/27897 A1 | 8/1997 |
| WO | WO 97/27898 A1 | 8/1997 |

(List continued on next page.)

OTHER PUBLICATIONS

Cragg et al. (1982). "Endovascular Diathermic Vessel Occlusion," *Radiology.* 144: 303–308.
Gorisch et al. (1982). "Heat–Induced Contraction of Blood Vessels," *Lasers in Surgery and Medicine.* 2: 1–13.
Heijmen et al. (1999). "A Novel One–Shot Anastomotic Stapler Prototype for Coronary Bypass Grafting on the Beating Heart: Feasibility in the Pig," *J. Thorac Cardiovasc Surg.* 117: 117–125.
Yusuf, S. W. et al. (1994). "Transfemoral Endoluminal Repair of Abdominal Aortic Aneurysm with Bifuricated Graft, "*Lancet*344(8923):650–651.

* cited by examiner

*Primary Examiner*—Michael J. Milano
(74) *Attorney, Agent, or Firm*—Morrison & Foerster LLP

(57) ABSTRACT

A sutureless anastomosis systems for securing a bypass graft to a host vessel or other tubular structure including a bypass graft and fitting. A compression mechanism may be used with the system for attachment of the bypass graft to the fitting. An electrode is connected to the fitting and an energy source. The energy source transmits energy to the electrode and causes the adjacent tissue to rise in temperature and bond to a vessel or fitting.

7 Claims, 70 Drawing Sheets

U.S. PATENT DOCUMENTS

| | | |
|---|---|---|
| 4,950,227 A | 8/1990 | Savin et al. |
| 5,067,957 A | 11/1991 | Jervis |
| 5,078,736 A | 1/1992 | Behl |
| 5,156,613 A | 10/1992 | Sawyer |
| 5,190,546 A | 3/1993 | Jervis |
| 5,234,447 A | 8/1993 | Kaster et al. |
| 5,391,156 A | 2/1995 | Hildwein et al. |
| 5,405,322 A | 4/1995 | Lennox et al. |
| 5,443,497 A | 8/1995 | Venbrux |
| 5,503,635 A | 4/1996 | Sauer et al. |
| 5,571,167 A | 11/1996 | Maginot |
| 5,591,226 A | 1/1997 | Trerotola et al. |
| 5,597,378 A | 1/1997 | Jervis |
| 5,628,784 A | 5/1997 | Strecker |
| 5,657,429 A | 8/1997 | Wang et al. |
| 5,665,117 A | 9/1997 | Rhodes |
| 5,669,934 A | 9/1997 | Sawyer |
| 5,676,670 A | 10/1997 | Kim |
| 5,690,675 A | 11/1997 | Sawyer et al. |
| 5,695,504 A | 12/1997 | Gifford, III et al. |
| 5,697,968 A | 12/1997 | Rogers et al. |
| 5,702,418 A | 12/1997 | Ravenscroft |
| 5,720,755 A | 2/1998 | Dakov |
| 5,725,544 A | 3/1998 | Rygaard |
| 5,728,133 A * | 3/1998 | Kontos ................ 606/213 |
| 5,749,375 A | 5/1998 | Maginot |
| 5,749,895 A | 5/1998 | Sawyer et al. |
| 5,755,775 A | 5/1998 | Trerotola et al. |
| 5,762,458 A | 6/1998 | Wang et al. |
| 5,779,718 A | 7/1998 | Green et al. |
| 5,797,920 A | 8/1998 | Kim |
| 5,797,934 A | 8/1998 | Rygaard |
| 5,810,884 A | 9/1998 | Kim |
| 5,814,005 A * | 9/1998 | Barra ................ 606/153 |
| 5,824,015 A | 10/1998 | Sawyer |
| 5,861,003 A | 1/1999 | Latson et al. |
| 5,868,759 A | 2/1999 | Peyser et al. |
| 5,868,761 A | 2/1999 | Nicholas et al. |
| 5,868,770 A | 2/1999 | Rygaard |
| 5,871,536 A | 2/1999 | Lazarus |
| 5,934,286 A | 8/1999 | Maginot |
| 5,938,672 A | 8/1999 | Nash |
| 5,938,696 A | 8/1999 | Goicoechea et al. |
| 5,944,019 A | 8/1999 | Knudson et al. |
| 5,944,730 A | 8/1999 | Nobles et al. |
| 5,944,738 A | 8/1999 | Amplatz et al. |
| 5,944,750 A | 8/1999 | Tanner et al. |
| 5,954,735 A | 9/1999 | Rygaard |
| 5,957,940 A | 9/1999 | Tanner et al. |
| 5,964,782 A * | 10/1999 | Lafontaine ................ 606/213 |
| 5,968,053 A | 10/1999 | Revelas |
| 5,968,089 A | 10/1999 | Krajiček |
| 5,968,090 A | 10/1999 | Ratcliff et al. |
| 5,972,017 A | 10/1999 | Berg et al. |
| 5,972,023 A | 10/1999 | Tanner et al. |
| 5,976,178 A | 11/1999 | Goldsteen et al. |
| 5,979,455 A | 11/1999 | Maginot |
| 5,984,955 A | 11/1999 | Wisselink |
| 5,989,276 A | 11/1999 | Houser et al. |
| 5,989,287 A | 11/1999 | Yang et al. |
| 5,993,468 A | 11/1999 | Rygaard |
| 6,001,124 A | 12/1999 | Bachinski |
| 6,007,576 A | 12/1999 | McClellan |
| 6,010,529 A | 1/2000 | Herweck et al. |
| 6,017,352 A | 1/2000 | Nash et al. |
| 6,019,788 A | 2/2000 | Butters et al. |
| 6,030,370 A | 2/2000 | Kupka et al. |
| 6,030,392 A | 2/2000 | Dakov |
| 6,036,702 A | 3/2000 | Bachinski et al. |
| 6,036,703 A | 3/2000 | Evans et al. |
| 6,036,705 A | 3/2000 | Nash et al. |
| 6,048,362 A | 4/2000 | Berg |
| 6,056,762 A | 5/2000 | Nash et al. |
| 6,063,114 A | 5/2000 | Nash et al. |
| 6,068,654 A | 5/2000 | Berg et al. |
| 6,071,305 A | 6/2000 | Brown et al. |
| 6,074,416 A | 6/2000 | Berg et al. |
| 6,113,612 A | 9/2000 | Swanson et al. |
| 6,117,147 A | 9/2000 | Simpson et al. |
| 6,120,432 A | 9/2000 | Sullivan et al. |

FOREIGN PATENT DOCUMENTS

| | | |
|---|---|---|
| WO | WO 97/31575 A1 | 9/1997 |
| WO | WO 97/43961 | 11/1997 |
| WO | WO 98/03118 | 1/1998 |
| WO | WO 97/40754 A1 | 2/1998 |
| WO | WO 98/07399 | 2/1998 |
| WO | WO 98/08456 A1 | 3/1998 |
| WO | WO 98/19608 A1 | 5/1998 |
| WO | WO 98/19618 A1 | 5/1998 |
| WO | WO 98/19629 A2 | 5/1998 |
| WO | Wo 98/19630 A2 | 5/1998 |
| WO | WO 98/19631 A1 | 5/1998 |
| WO | WO 98/19632 A1 | 5/1998 |
| WO | WO 98/19634 A2 | 5/1998 |
| WO | WO 98/19635 A1 | 5/1998 |
| WO | WO 98/19636 A2 | 5/1998 |
| WO | WO 98/19732 A1 | 5/1998 |
| WO | WO 98/38939 | 9/1998 |
| WO | WO 98/38941 | 9/1998 |
| WO | WO 98/42262 A1 | 10/1998 |
| WO | WO 98/55027 A2 | 12/1998 |
| WO | WO 98/57590 | 12/1998 |
| WO | WO 98/57591 | 12/1998 |
| WO | WO 98/57592 | 12/1998 |
| WO | WO 99/00055 A3 | 1/1999 |
| WO | WO 99/00055 A2 | 1/1999 |
| WO | WO 99/18887 A1 | 4/1999 |
| WO | WO 99/38454 A2 | 8/1999 |
| WO | WO 99/45852 A2 | 9/1999 |
| WO | WO 99/62408 | 12/1999 |
| WO | WO 99/62415 | 12/1999 |
| WO | WO 00/09040 | 2/2000 |
| WO | WO 00/24339 A1 | 5/2000 |
| WO | WO 00/27311 A1 | 5/2000 |
| WO | WO 00/27313 A2 | 5/2000 |
| WO | WO 00/40176 A1 | 7/2000 |
| WO | WO 00/53104 A1 | 9/2000 |

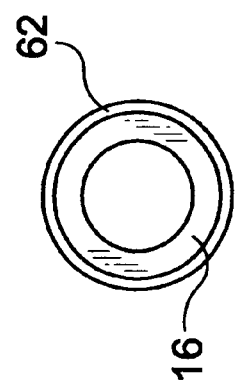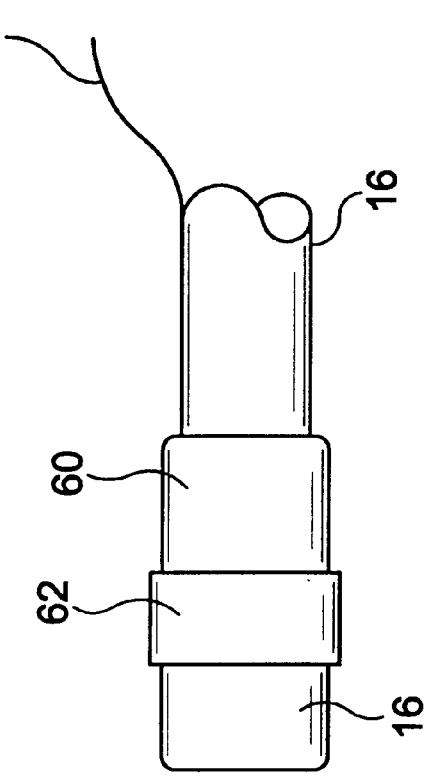

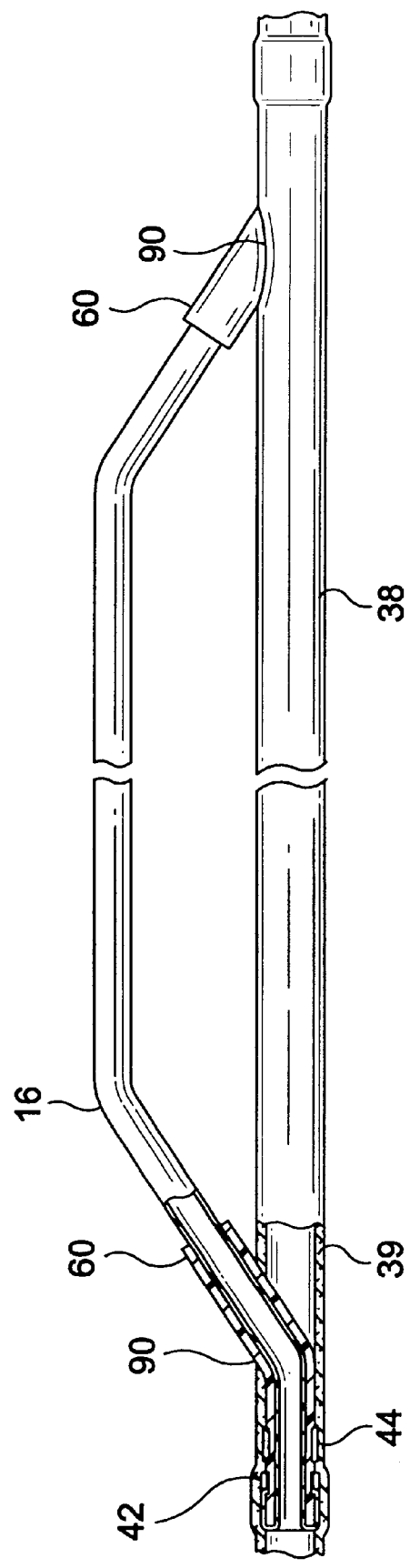

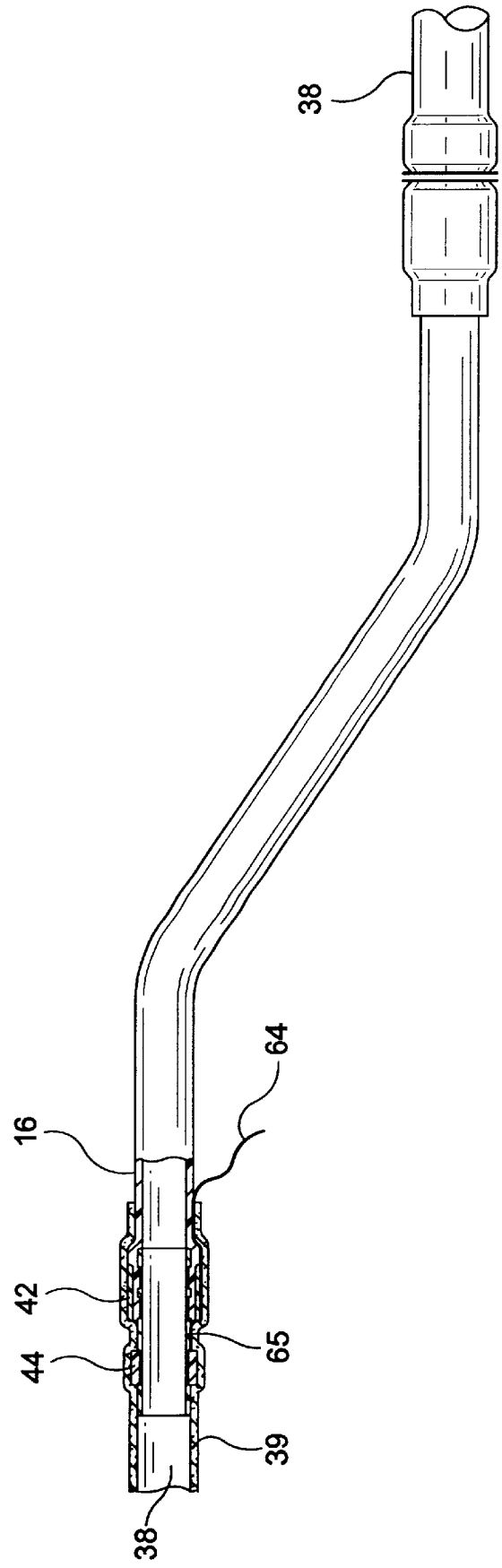

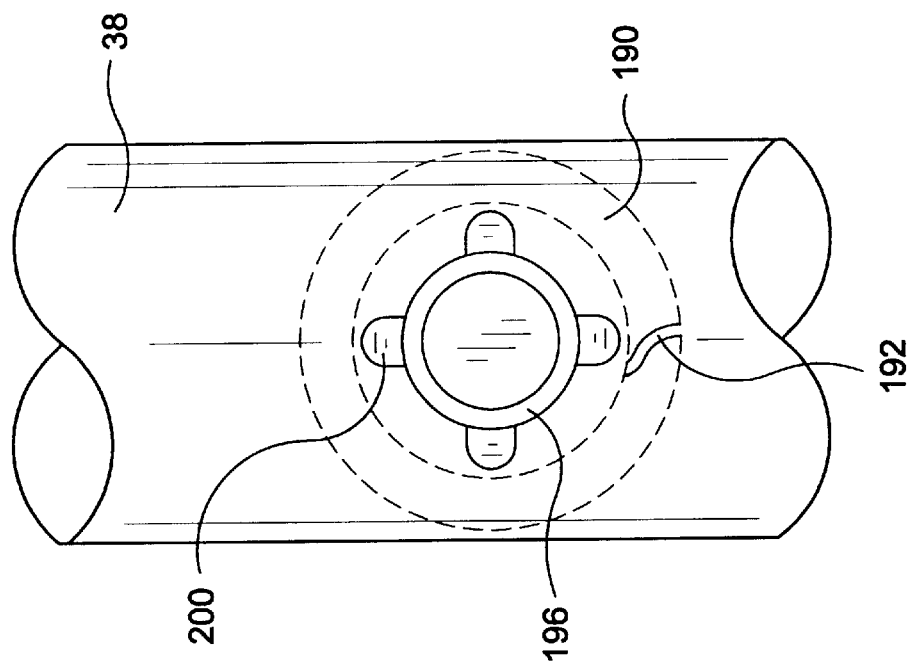
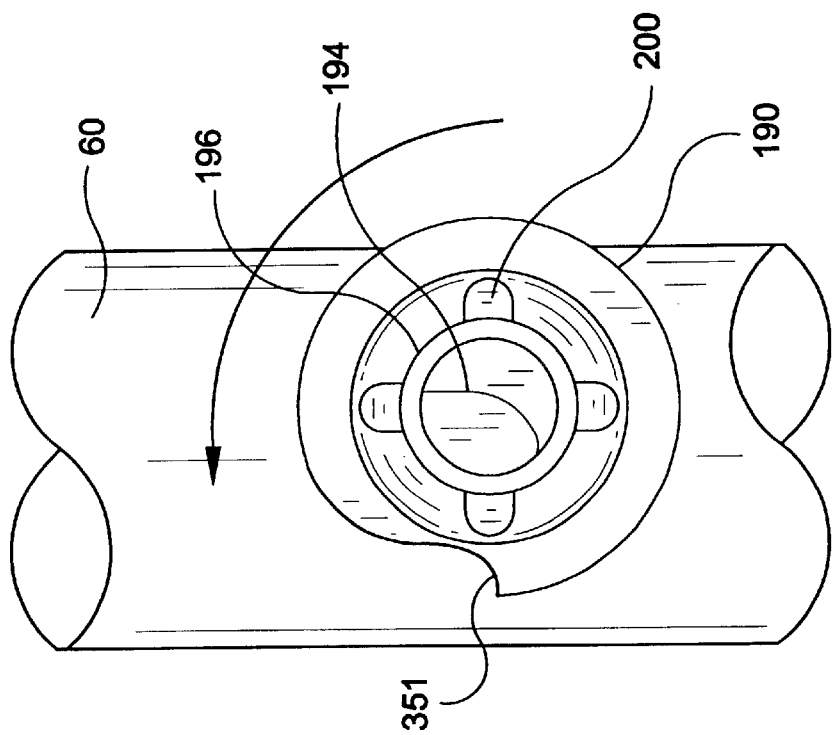

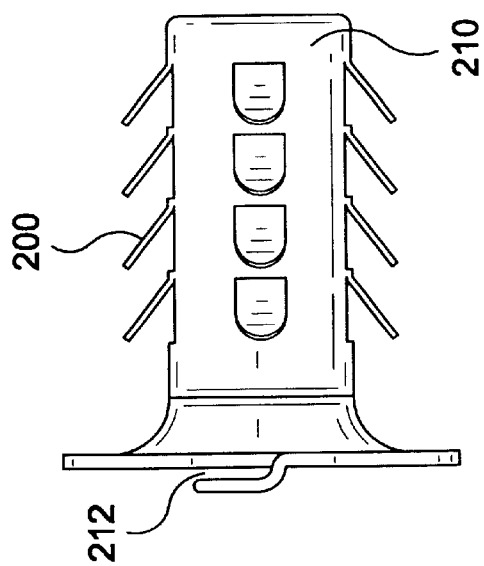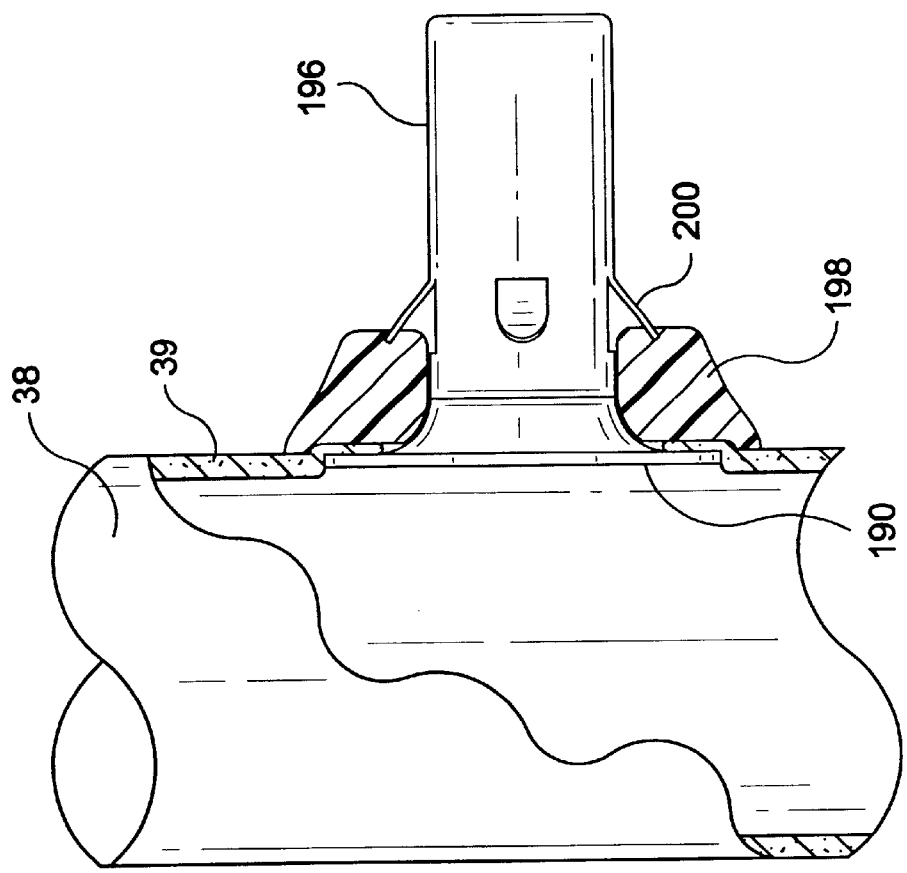

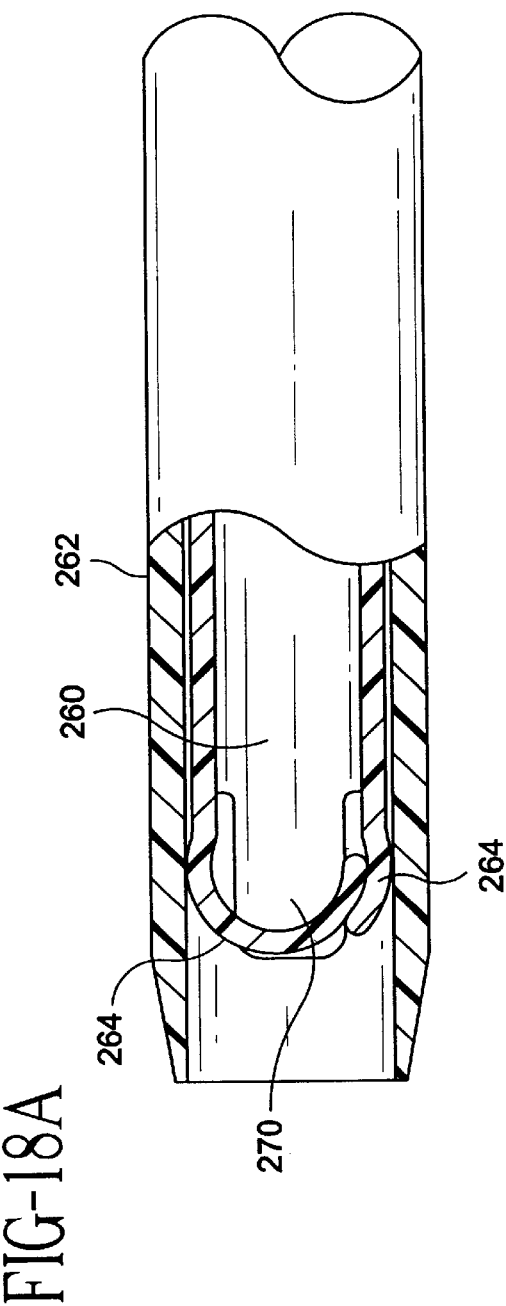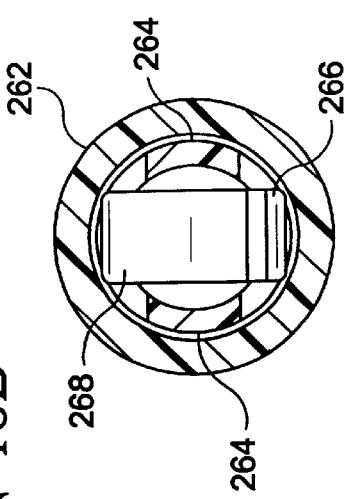
FIG-18A
FIG-18B

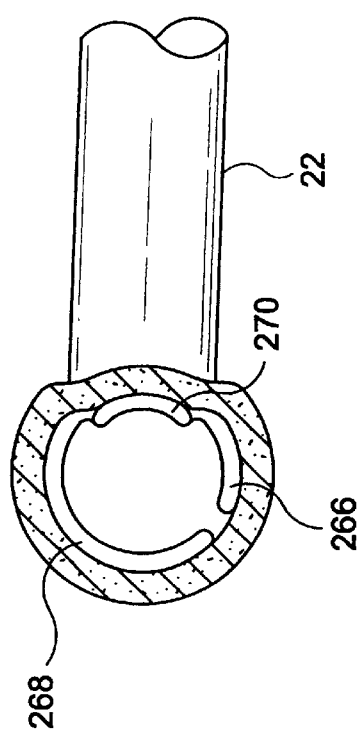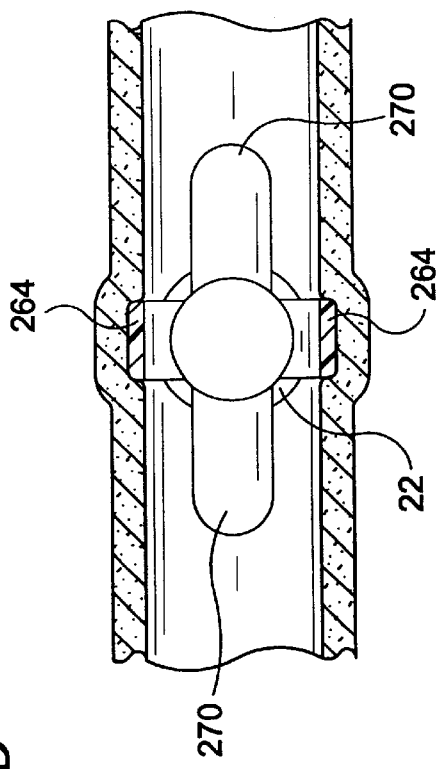

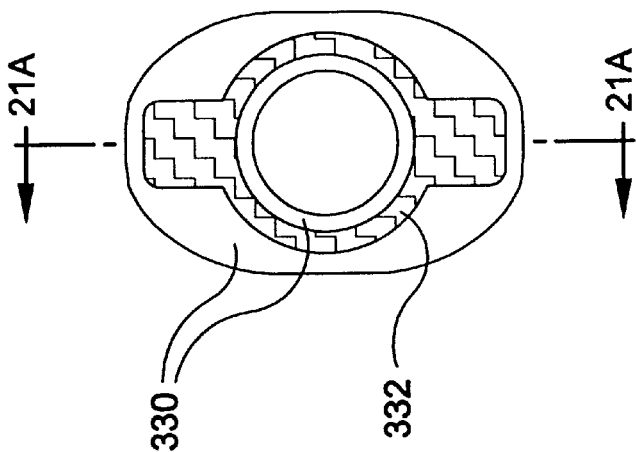
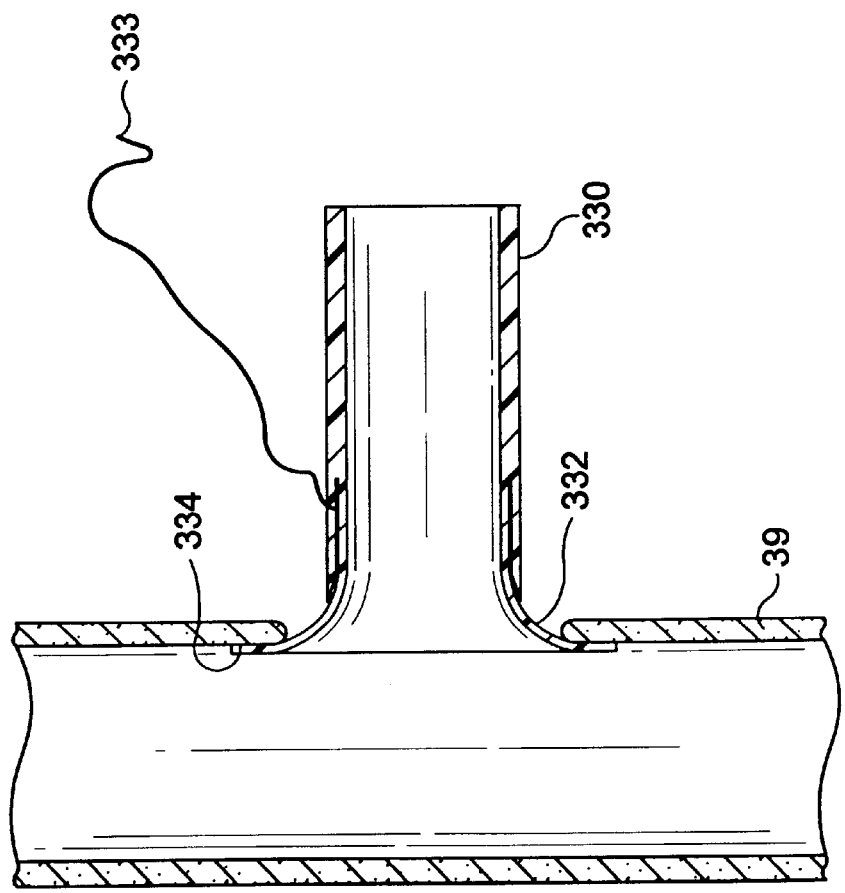

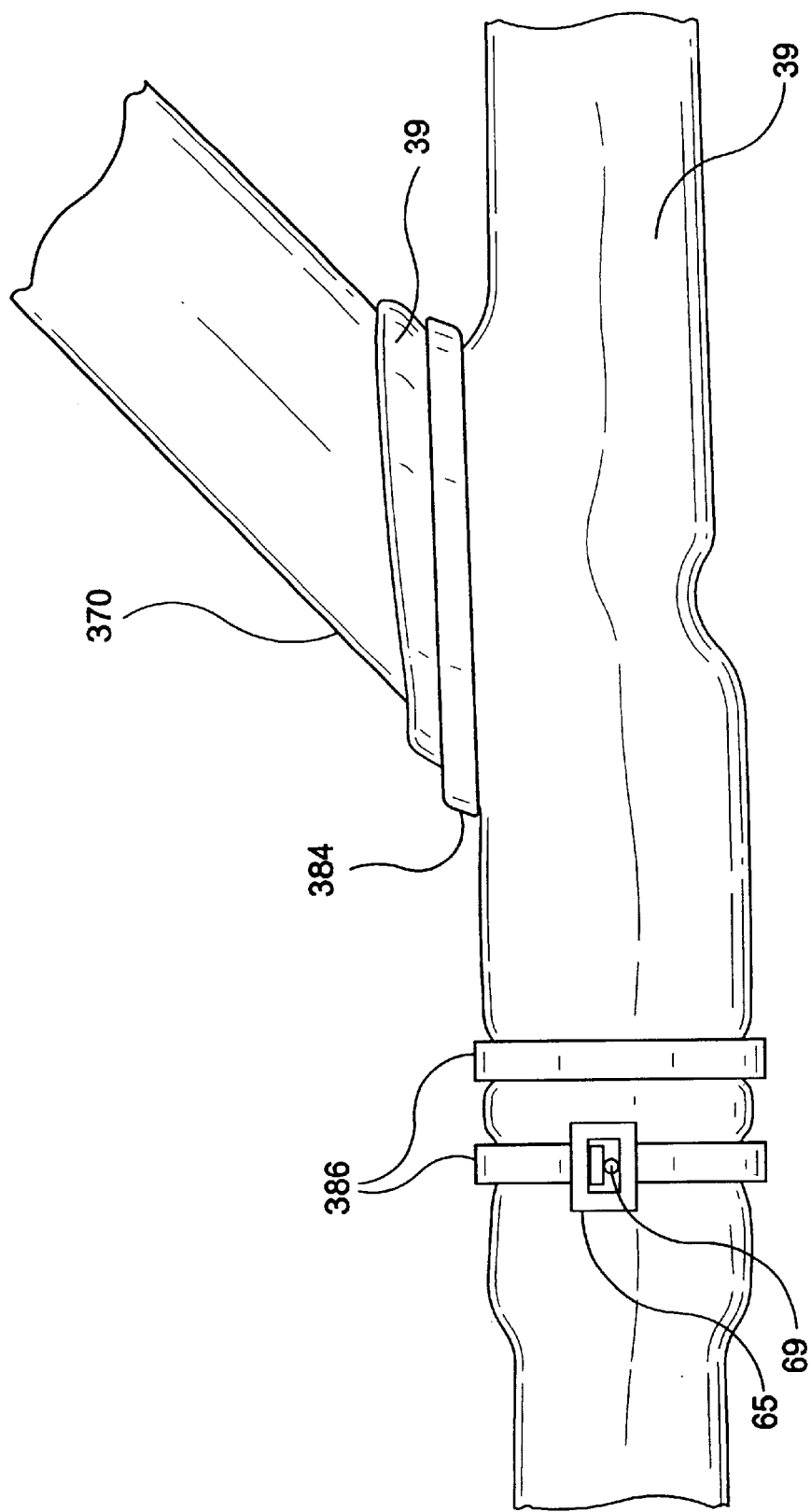

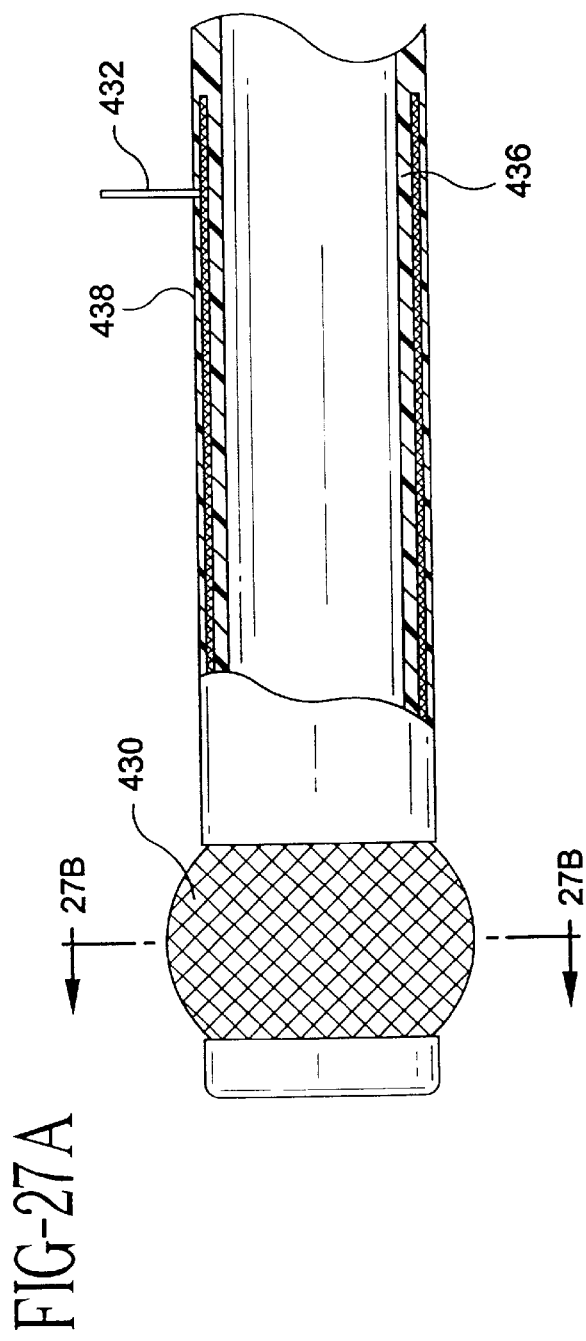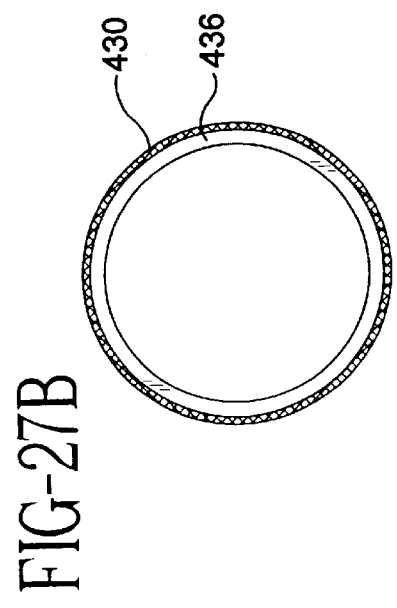
FIG-27A
FIG-27B

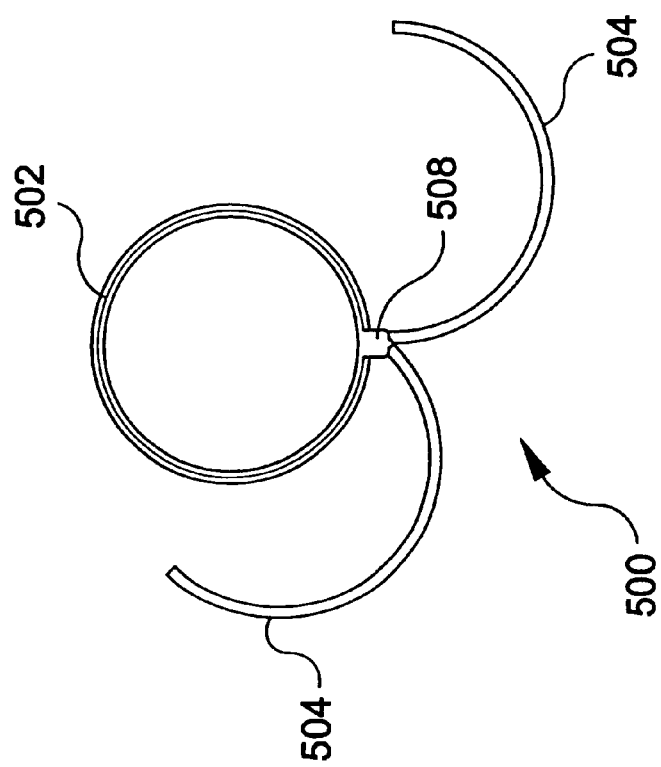
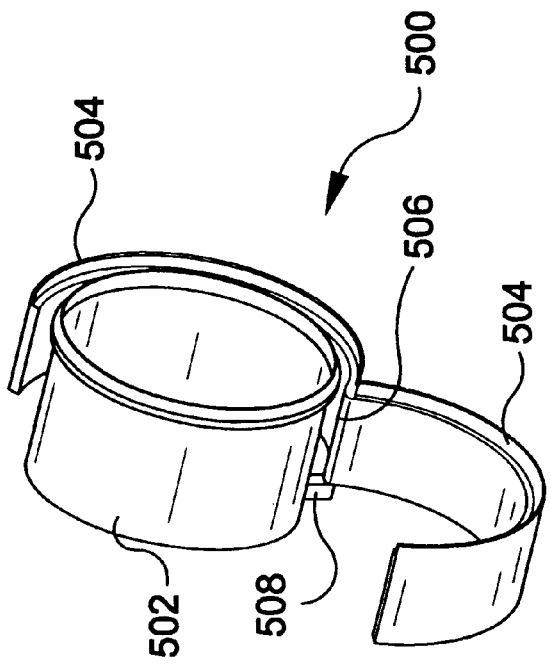
FIG-31B
FIG-31A

THERMAL SECURING ANASTOMOSIS SYSTEMS

This application is related to the following applications: now abandoned Provisional application Serial No. 60/111,948 filed Dec. 11, 1998; now abandoned Provisional application Serial No. 60/088,705 filed Jun. 10, 1998; now abandoned Provisional application Serial No. 60/030,733 filed Nov. 8, 1996; and co-pending U.S. application Serial No. 08/932,566 filed Sep. 19, 1997.

BACKGROUND OF THE INVENTION

The invention relates to devices for deploying and securing the ends of bypass grafts and for providing a fluid flow passage between at least two vessel regions or other tubular structure regions. More particularly, the invention relates to bypass grafts that are thermally secured at target vessel locations thereby producing a fluid flow passage from the first vessel location through the bypass graft to the second vessel location. The bypass grafts and deployment systems of the invention do not require stopping or re-routing blood flow to perform an anastomoses between a bypass graft and a host vessel. Accordingly, this invention describes sutureless anastomosis systems that do not require cardiopulmonary bypass support when treating coronary artery disease.

Stenosed blood vessels may cause ischemia and lead to tissue infarction. Conventional techniques to treat partially or completely occluded vessels include balloon angioplasty, stent deployment, atherectomy, and bypass grafting. Coronary artery bypass grafting (CABG) procedures to treat coronary artery disease have traditionally been performed through a thoracotomy with the patient placed on cardiopulmonary bypass support and using cardioplegia to induce cardiac arrest. Cardiac protection is required when performing bypass grafting procedures having prolonged ischemia times. Current bypass grafting procedures involve interrupting blood flow to suture or staple the bypass graft to the host vessel wall and create the anastomoses. When suturing or clipping the bypass graft to the host vessel wall, a generally large incision is made through the vessel and the bypass graft is sewn to the host vessel wall such that the endothelial layers of the bypass graft and vessel face each other. Bypass graft intima to host vessel intima apposition reduces the incidence of thrombosis associated with biological reactions that result from blood contacting the epithelial layer of a harvested bypass graft. This is especially relevant when using harvested vessels that have a small inner diameter (e.g. <2 mm).

Less invasive attempts for positioning bypass grafts at target vessel locations have used small ports to access the anatomy. These approaches use endoscopic visualization and modified surgical instruments (e.g. clamps, scissors, scalpels, etc.) to position and suture the ends of the bypass graft at the host vessel locations. Attempts to eliminate the need for cardiopulmonary bypass support while performing CABG procedures have benefited from devices that stabilize the motion of the heart, retractors that temporarily occlude blood flow through the host vessel, and shunts that re-route the blood flow around the anastomosis site. Stabilizers and retractors still require significant time and complexity to expose the host vessel and suture the bypass graft to the host vessel wall. Shunts not only add to the complexity and length of the procedure, but they require a secondary procedure to close the insertion sites proximal and distal to the anastomosis site.

Attempts to automate formation of sutureless anastomoses have culminated in mechanical stapling devices. Mechanical stapling devices have been proposed for creating end-end anastomoses between the open ends of transected vessels. Berggren, et al propose an automatic stapling device for use in microsurgery (U.S. Pat. Nos. 4,607,637; 4,624,257; 4,917,090; and 4,917,091). This stapling device has mating sections containing pins that are locked together after the vessel ends are fed through lumens in the sections and everted over the pins. This stapling device maintains intima to intima apposition for the severed vessel ends but has a large profile and requires impaling the everted vessel wall with the pins. Sakura describes a mechanical end-end stapling device designed to reattach severed vessels (U.S. Pat. No. 4,214,587). This device has a wire wound into a zig-zag pattern to permit radial motion and contains pins bonded to the wire that are used to penetrate tissue. One vessel end is everted over and secured to the pins of the end-end stapling device, and the other vessel end is advanced over the end-end stapling device and attached with the pins. Sauer, et al proposes another mechanical end-end device that inserts mating pieces into each open end of a severed vessel (U.S. Pat. No. 5,503,635). Once positioned, the mating pieces snap together thereby bonding the vessel ends. These end-end devices are amenable to reattaching severed vessels but are not suitable to producing end-end anastomoses between a bypass graft and an intact vessel, especially when exposure to the vessel is limited.

Mechanical stapling devices have also been proposed for end-side anastomoses. These devices are designed to insert bypass grafts, attached to the mechanical devices, into the host vessel through a large incision and secure the bypass graft to the host vessel. Kaster describes vascular stapling apparatus for producing end-side anastomoses (U.S. Pat. Nos. 4,366,819; 4,368,736; and 5,234,447). Kaster's end-side apparatus is inserted through a large incision in the host vessel wall. The apparatus has an inner flange that is placed against the interior of the vessel wall, and a locking ring that is affixed to the fitting and contains spikes that penetrate into the vessel thereby securing the apparatus to the vessel wall. The bypass graft is itself secured to the apparatus in the everted or non-everted position through the use of spikes incorporated in the apparatus design.

U.S. Surgical has developed automatic clip appliers that replace suture stitches with clips (U.S. Pat. Nos. 5,868,761; 5,868,759; and 5,779,718). These clipping devices have been demonstrated to reduce the time required when producing the anastomosis but still involve making a large incision through the host vessel wall. As a result, blood flow through the host vessel must be interrupted while creating the anastomoses.

Gifford, et al provides end-side stapling, devices (U.S. Pat. No. 5,695,504) that secure harvested vessels to host vessel walls maintaining intima to intima apposition. This stapling device is also inserted through a large incision in the host vessel wall and uses staples incorporated in the device to penetrate into tissue and secure the bypass graft to the host vessel.

Walsh, et al propose a similar end-side stapling device (U.S. Pat. Nos. 4,657,019; 4,787,386; 4,917,087). This end-side device has a ring with tissue piercing pins. The bypass graft is everted over the ring; then, the pins penetrate the bypass graft thereby securing the bypass graft to the ring. The ring is inserted through a large incision created in the host vessel wall and the tissue piercing, pins are used to puncture the host vessel wall. A clip is then used to prevent dislodgment of the ring relative to the host vessel.

The end-side stapling devices previously described require insertion through a large incision, which dictates that blood flow through the host vessel must be interrupted during the process. Even though these and other clipping and stapling end-side anastomotic devices have been designed to decrease the time required to create the anastomosis, interruption of blood flow through the host vessel increases the morbidity and mortality of bypass grafting procedures, especially during beating heart CABG procedures. A recent experimental study of the U.S. Surgical One-Shot anastomotic clip applier observed abrupt ventricular fibrillation during four of fourteen internal thoracic artery to left anterior descending artery anastomoses in part due to coronary occlusion times exceeding 90 seconds (Heijmen, et al. A novel one-shot anastomotic stapler prototype for coronary bypass grafting on the beating heart: feasibility in the pig. *J Thorac Cardiovasc Surg*. 117:117—25; 1999).

All documents cited herein, including the foregoing, are incorporated herein by reference in their entireties for all purposes.

SUMMARY OF THE INVENTION

The present inventions provide sutureless anastomosis systems that enable a physician to quickly and accurately secure a bypass graft to a host vessel or other tubular body structure. In addition, the invention enables the physician to ensure bypass graft stability, and prevent leaking at the vessel attachment points. The delivery systems of the invention do not require stopping or re-routing blood flow while producing the anastomosis as compared to some current techniques that require interrupting blood flow to suture, clip, or staple a bypass graft to the vessel wall.

A need for bypass grafts and delivery systems that are capable of quickly producing an anastomosis between a bypass graft and a host vessel wall without having to stop or re-route blood flow. These anastomoses must withstand the pressure exerted by the pumping heart and ensure that blood does not leak from the anastomoses into the thoracic cavity, abdominal cavity, or other region exterior to the vessel wall.

Current techniques for producing anastomoses during coronary artery bypass grafting procedures involve placing the patient on cardiopulmonary bypass support, arresting the heart, and interrupting blood flow to suture or staple a bypass graft to the coronary artery and aorta. Cardiopulmonary bypass support is associated with substantial morbidity and mortality. The embodiments of the invention are used to position and secure bypass grafts at host vessel locations without stopping or rerouting blood flow. Accordingly, the embodiments of the invention do not require cardiopulmonary bypass support and arresting the heart while producing anastomoses to the coronary arteries. In addition, the invention generally mitigates risks associated with suturing or clipping the bypass graft to the host vessel, namely bleeding at the attachment site and collapse of the vessel around the incision point.

The invention addresses vascular bypass graft treatment regimens requiring end-to-end anastomoses and end-to-side anastomoses to attach bypass grafts to host vessels. The scope of the invention includes systems to position and thermally secure bypass grafts used to treat vascular diseases such as atherosclerosis, arteriosclerosis, fistulas, aneurysms, occlusions, and thromboses. In addition, the systems may be used to bypass stented vessel regions that have restenosed or thrombosed. The bypass grafts and delivery systems of the invention are also used to attach the ends of ligated vessels, replace vessels harvested for bypass grafting procedures (e.g. radial artery), and re-establish blood flow to branching vessels which would otherwise be occluded during surgical grafting procedures (e.g. the renal arteries during abdominal aortic aneurysm treatment). In addition, the invention addresses other applications including arterial to venous shunts for hemodialysis patients, bypassing lesions and scar tissue located in the fallopian tubes causing infertility, attaching the ureter to the kidneys during transplants, and bypassing gastrointestinal defects (e.g. occlusions, ulcers).

One aspect of the invention provides fittings constructed from a metal (e.g. titanium), alloy (e.g. stainless steel or nickel titanium), thermoplastic, thermoset, composite of the aforementioned materials, or other suitable material, and designed to exert radial force at the vessel attachment points to maintain bypass graft patency. The fittings are advanced through the delivery system and are attached to the vessel wall at target locations. The delivery system is a combination of tear-away sheath, dilator, guidewire, and needle designed to be inserted into the vessel at the desired locations. The tubing, hub and valve of the tear-away sheath are configured to split so the entire sheath may be separated and removed from around the bypass graft after attaching the bypass graft to the host vessel. A plunger is used to insert the bypass graft and fitting combination through the sheath and into the vessel. The dilator and needle may incorporate advanced features, such as steering, sensing, and imaging, used to facilitate placing and locating the bypass graft and fitting combination.

In accordance with the invention, the fittings incorporate mechanisms to thermally secure a bypass graft to a host vessel. One fitting configuration produces an anastomosis between a harvested bypass graft and a host vessel such that only the endothelial layer of the bypass graft is exposed to the interior of the host vessel. The invention also describes fittings designed to permit retrograde flow past the anastomosis site so as to maintain flow through the lesion and to branching vessels located proximal to the anastomosis site. A further aspect of the invention provides fittings having branches to accommodate multiple bypass grafts using a single proximal anastomosis.

Fittings and accompanying components constructed from a conductive material may be used as electrodes to deliver radiofrequency energy to tissue contacting the electrode. Radiofrequency energy is applied to each fitting component (unipolar to an indifferent electrode, or bipolar between fitting components) to thermally secure the bypass graft to the vessel wall. Radiofrequency energy produces ohmic heating of adjacent tissue causing it to coagulate to the electrodes and locally shrinking the vessel wall around the fitting to produce an interference fit between the vessel wall and the bypass graft fitting. This not only thermally secures the bypass graft to the vessel wall but also prevents leaking around the bypass graft to host vessel interface.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTION OF DRAWINGS

FIGS. 3a–c show an end-to-end fitting that thermally secures a bypass graft to a host vessel;

FIGS. 7a–b show a bypass graft everted around and attached to end-to-end fittings, and secured to the host vessel;

FIGS. 8a–d show a bypass graft secured to the host vessel;

FIGS. 15a–e show an end-to-side fitting that may be delivered past a vessel wall without the need for a sheath;

FIGS. 16a–g show alternative end-to-side fitting embodiments that may be delivered past a host vessel wall without the need for a sheath;

FIGS. 18a–g show an end-to-side fitting for host vessels having small and medium diameters;

FIGS. 21a–d show an end-to-side fittings having an electrode incorporated in the fitting;

FIGS. 24a–b are close-up views of the bypass graft and fitting combination shown in FIG. 23;

FIGS. 27a–b show an end-to-end bypass graft having an expandable and compressible electrode secured to the bypass graft;

FIGS. 31a–d show other embodiments of a fitting system; and

DETAILED DESCRIPTION OF PREFERRED EMBODIMENTS

The fittings and delivery systems are intended to produce anastomoses between bypass grafts and host vessels to treat vascular abnormalities such as stenoses, thromboses, other occlusions, aneurysms, fistulas, or other indications requiring a bypass graft. The systems are useful in bypassing stented vessels that have restenosed. Some approaches to treating stenosed stents have not been successful and reliable at removing the lesion and opening the vessel lumen. The approach described by this invention, produces a blood flow conduit around the stented lesion and mitigates concerns associated with damaging the stent or forming emboli when removing deposits attached to the stent. The fittings are used for securing and supporting the ends of transected vessels cut during organ transplantations. The embodiments also provide mechanisms to secure branching vessels to a replacement graft during surgical procedures in which the branching vessels would otherwise be occluded from the blood flow (e.g. reattaching the renal arteries, mesenteric artery, celiac artery, and intercostal arteries during treatment of abdominal aortic aneurysms that are pararenal, suprarenal, or thoracoabdominal in classification).

Figure 1:
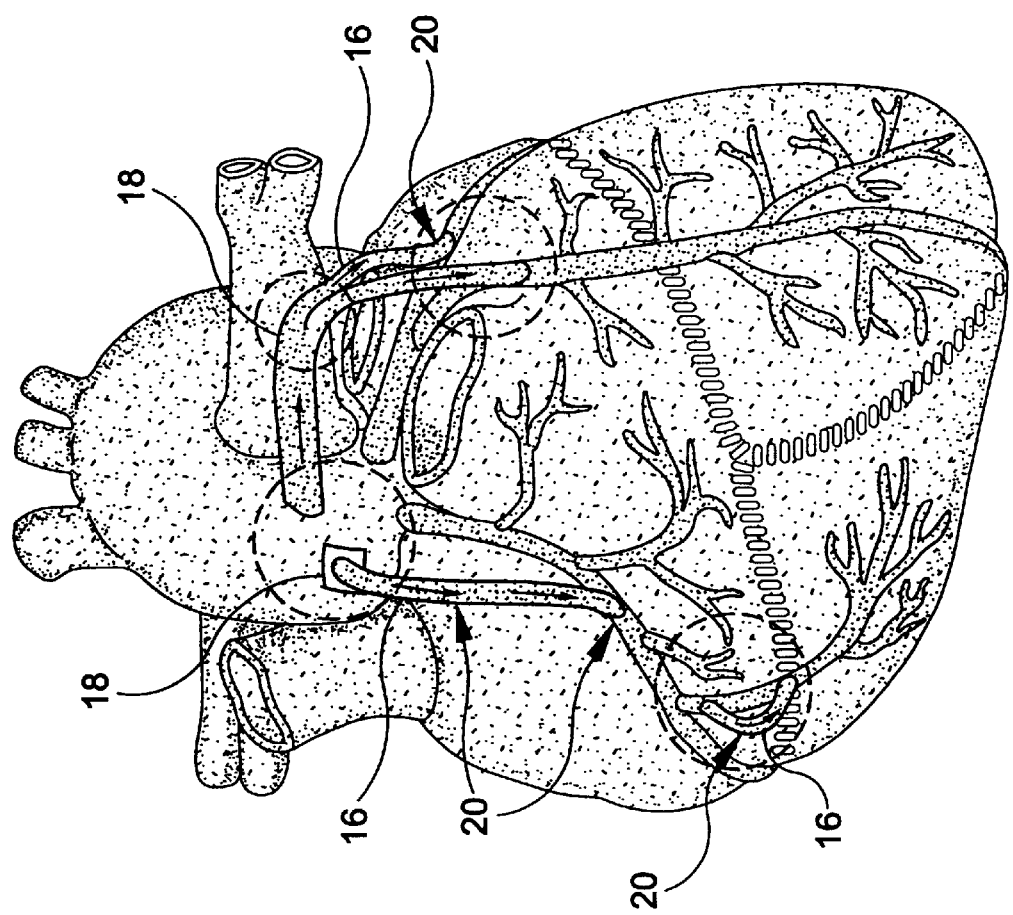
FIG. 1 shows a heart containing multiple bypass grafts positioned and secured to host vessels.

Referring more particularly to the drawings, FIG. 1 illustrates bypass grafts secured to host vessels during coronary artery bypass grafting (CABG) procedures. Bypass graft 16 provides a blood flow passage from the aorta to the right coronary artery. An end-to-side fitting 18 is used to secure the proximal end of the bypass graft 16 to the aorta and fitting 18 or end-to-end fitting 20 is used to secure the distal end of the bypass graft to the right coronary artery. Bypass graft 16 provides a blood flow passage along a small vessel such as a coronary artery by securing the bypass graft to the host vessel with fittings 18, 20. Bypass graft 16 is secured to the aorta with a fitting 18, 20 that branches into distinct bypass grafts which are further secured to the left anterior descending artery and circumflex artery using fittings 18, 20. The bypass grafts and fittings in these examples demonstrate representative applications and should not limit the scope of use for the embodiments of the invention. It should be noted that the combination of fittings used to secure a bypass 16 graft to a host vessel, along a host vessel, or between host vessels depends on the application.

The bypass graft 16 may be a synthetic graft material biological bypass graft, harvested vessel, or other tubular body structure, depending on the indication. The harvested vessels may be an internal mammary artery, radial artery, saphenous vein or other body tubing. Harvested vessels may be dissected using newer minimally invasive, catheter-based techniques or standard surgical approaches. Fittings in accordance with the invention are designed to attach bypass grafts to host vessels (or other tubular structures). The fittings 18, 20 used to position and attach such bypass grafts 16 are extensions of the collet and grommet embodiments described in U.S. application Serial No. 08/966,003 filed Nov. 7, 1997. An advantage of biological bypass grafts over available synthetic materials is the reduction in thrombosis, especially when using small diameter (e.g. <2 mm) bypass grafts. The fittings and delivery systems of the invention are generally equally effective at positioning and securing all types of bypass grafts, biological and synthetic.

Synthetic bypass grafts may be manufactured by extruding, injection molding, weaving, braiding, or dipping polymers such as PTFE, expanded PTFE, urethane, polyamide, nylon, silicone, polyethylene, collagen, polyester or composites of these representative materials. These materials may be fabricated into a sheet or tubing using one or a combination of the stated manufacturing processes. The sides of sheet materials may be bonded using radiofrequency energy, laser welding, ultrasonic welding, thermal bonding, sewing, adhesives, or a combination of these processes to form tubing. The synthetic bypass graft may also be coated, deposited, or impregnated with materials, such as paralyne, heparin, hydrophilic solutions, or other substrates designed to reduce thrombosis or mitigate other risks that potentially decrease the patency of synthetic bypass grafts. The primary advantage of synthetic bypass graft materials is the ability to bond the bypass graft to the fittings prior to starting the procedure or incorporate the fittings into the bypass graft design by injection molding or other manufacturing process. Currently, synthetic bypass grafts are indicated for blood vessels having medium and large diameters (e.g. >3 mm), such as peripheral vessels, tubular structures such as the fallopian tubes, or shunts for hemodialysis. However, medical device manufacturers such as Possis Medical, Inc. and Thoratec Laboratories, Inc. are clinically evaluating synthetic bypass grafts for coronary indications.

Support members may be incorporated into a graft as referenced in co-pending U.S. application Serial No. 08/932, 566 filed Sep. 19, 1997 and in co-pending U.S. application Serial No. 08/966,003 filed Nov. 7, 1997. When using synthetic bypass grafts, the support members may be laminated between layers of graft material. The synthetic bypass graft 16 may be fabricated by extruding, injection molding, or dipping a primary layer of the graft over a removable mandrel; positioning, winding or braiding the support members on the primary layer; and extruding, injection molding, or dipping a secondary layer over the material/support member combination. The support members preferably have a shape memory. Memory elastic alloys, such as nickel titanium, exhibiting stress-induced martensite characteristics may be used to reinforce the bypass graft and/or vessel wall and prevent permanent deformation upon exposure to external forces.

Alternatively, synthetic bypass grafts 16 incorporating support members may be fabricated using cellulosic materials such as regenerated cellulose. Cellulosic materials may be extruded, wrapped, injection molded, or dipped in layers to laminate the support members between graft material layers. Cellulosics, and other such materials, which have a high water adsorption rate, are relatively stiff when dehydrated and flexible when hydrated. This characteristic provides a means to maintain a self-expanding material such as the support members in a collapsed state. The cellulosic material in its dry, stiff state counteracts the radial force of the self-expanding support members and prevents the graft from expanding until it becomes hydrated, thus more flexible. When the bypass graft 16 is inserted through the delivery system and into the vessel, the cellulosic material contacts fluid, causing it to become more flexible and the support members of the bypass graft 16 to expand towards its resting state and the graft into intimate contact with the vessel wall.

Figure 2A:
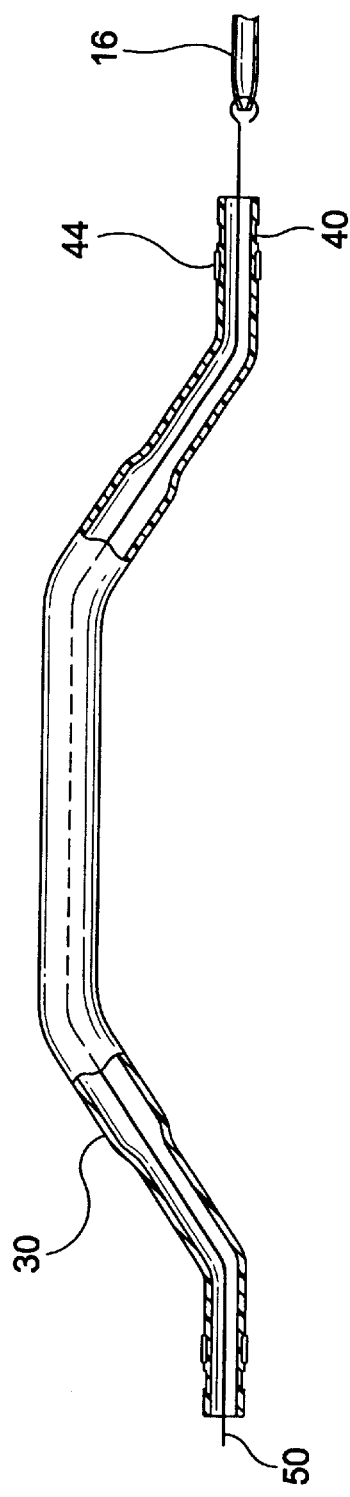
FIGS. 2a–b are side-sectional views of a bypass graft support structure incorporating fittings.
Figure 2B:
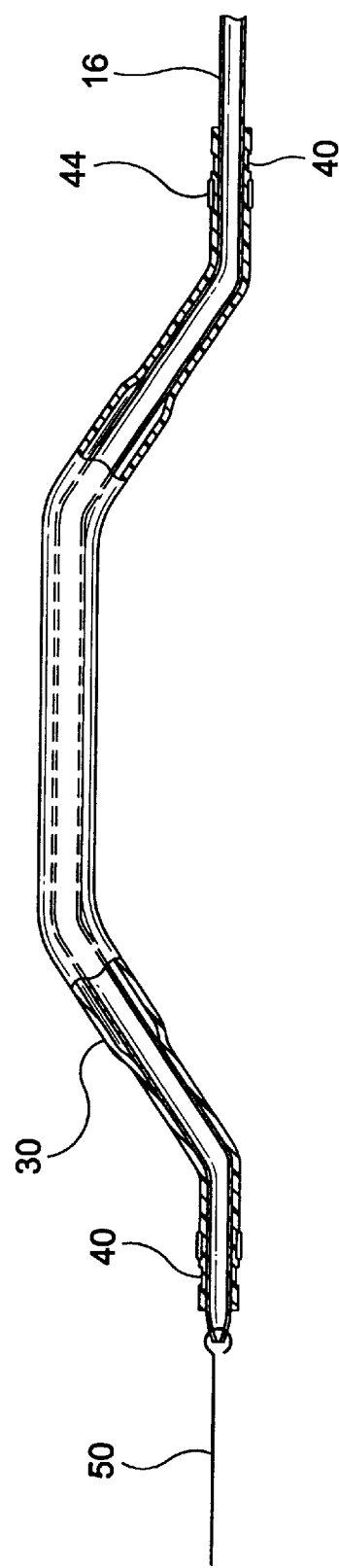
Figure 2C:
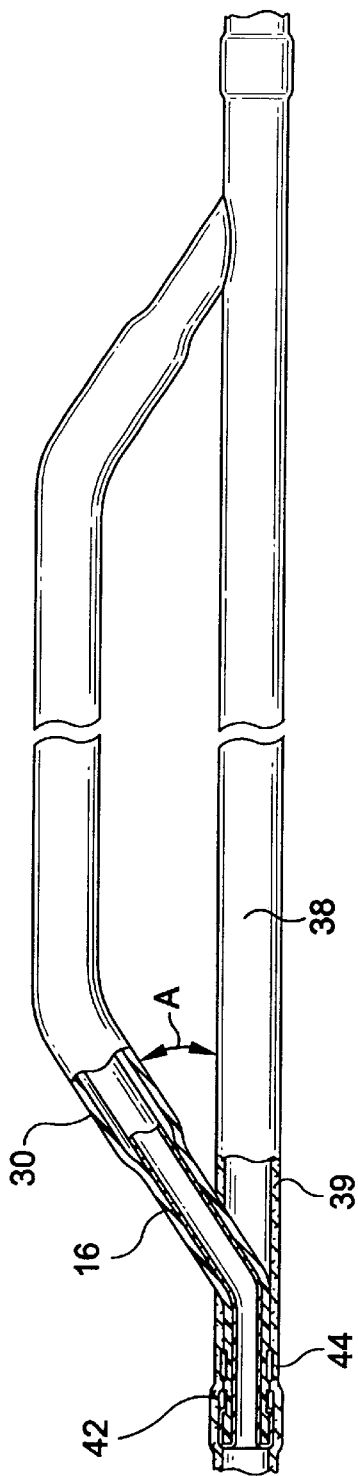
FIG. 2c shows a support structure, with an attached bypass graft, thermally secured to a host vessel at two locations.

Biological bypass grafts 16 may be reinforced with a support structure 30 as shown in FIGS. 2a–c. This support structure 30 may consist of a wire material wound into a helix or braided into a mesh. Other reinforcing structures that limit expansion of the bypass graft 16 may also be used. The support structure 30 is bonded to fittings at each end by spot welding, crimping, soldering, ultrasonic welding, thermal bonding, adhesively bonding, or other bonding process, depending on the materials. The support structure 30 defines a lumen into which the bypass graft 16 is inserted. After advancing the bypass graft 16 through the support structure 30, the bypass graft 16 is secured to the fittings at each end of the support structure 30. The support structure 30 generally reduces the potential for kinking of the bypass graft 16, limits the radial expansion of the bypass graft 16, prevents aneurysm formation, and increases the burst strength of the bypass graft 16. By mitigating the failure mechanisms of bypass grafts 16 such as the saphenous veins, such reinforcing structures may improve the long-term durability and patency of the bypass graft 16.

The support structure 30 may alternatively be a synthetic graft material formed into a tube, with or without support members. The support structure 30 may be fabricated from a polymer that is macroporous to permit blood leaking through the bypass graft to flow outside the support structure. Biological bypass grafts typically have branches that are sutured or stapled closed while harvesting the vessel and may leak for a period of time immediately after implantation. Blood leaking through a biological bypass graft enclosed in a nonporous or microporous (e.g. pore size <8 $\mu$m) support structure may accumulate between the bypass graft and the support structure 32 and occlude the bypass graft depending on the pressure gradient between the inside of the bypass graft 16 and the space between the graft and the support structure 30. For applications where the biological bypass graft is completely impervious to leaking or where the external surface of the biological bypass graft can be bonded to the support structure (e.g. using adhesives), nonporous or microporous support structures may be used.

The support structure 30 is preferably affixed to the fittings before attaching the bypass graft 16 to the fittings. This ensures the support structure reinforces the entire length of the bypass graft 16. Using a support structure that is not affixed to the fittings may cause kinking of the bypass graft in the region between the anastomosis site and the end of the support structure, which defines a region where the bypass graft is not reinforced. The support structure 30 incorporates fittings at each end for attachment of a harvested vessel 16 and for securing the bypass graft to the host vessel 38. As shown in FIGS. 2a–b, a grasping tool 50 including a suture with a noose or a wire with a distal gripping end such as forceps, is fed through the support structure and is used to grab the harvested vessel 16. The harvested vessel 16 is pulled through the support structure 30 such that a length of the harvested vessel extends beyond both ends of the support structure fittings. FIG. 2c shows the ends of the harvested vessel 16 everted around the support structure fittings and secured at the notched regions 40 of the fittings using retaining rings 42. Electrodes 44 may be included in the support structure to thermally secure the support structure 30 and the bypass graft to the host vessel wall 39. The blood flowing through the bypass graft 16 contacts the endothelial layers of the harvested bypass graft and host vessel thereby minimizing the potential for thrombosis or biological reactions to foreign materials.

When microporous or nonporous support structures may be used, the support structures may serve dual purposes. They may function as synthetic bypass grafts designed to produce two end-end anastomoses at opposite ends of the bypass grafts. The support structure/bypass grafts may be configured with one or both ends incorporating fittings that enable end-side anastomoses. They also function as sutureless anastomosis devices to attach harvested vessels and reinforce the biological bypass grafts. This combined functionality minimizes the product portfolio required for bypass grafting indications because a single device may reinforce and facilitate attaching harvested vessels between anastomosis sites and act as a synthetic bypass graft capable of producing sutureless anastomoses.

Figure 8B:
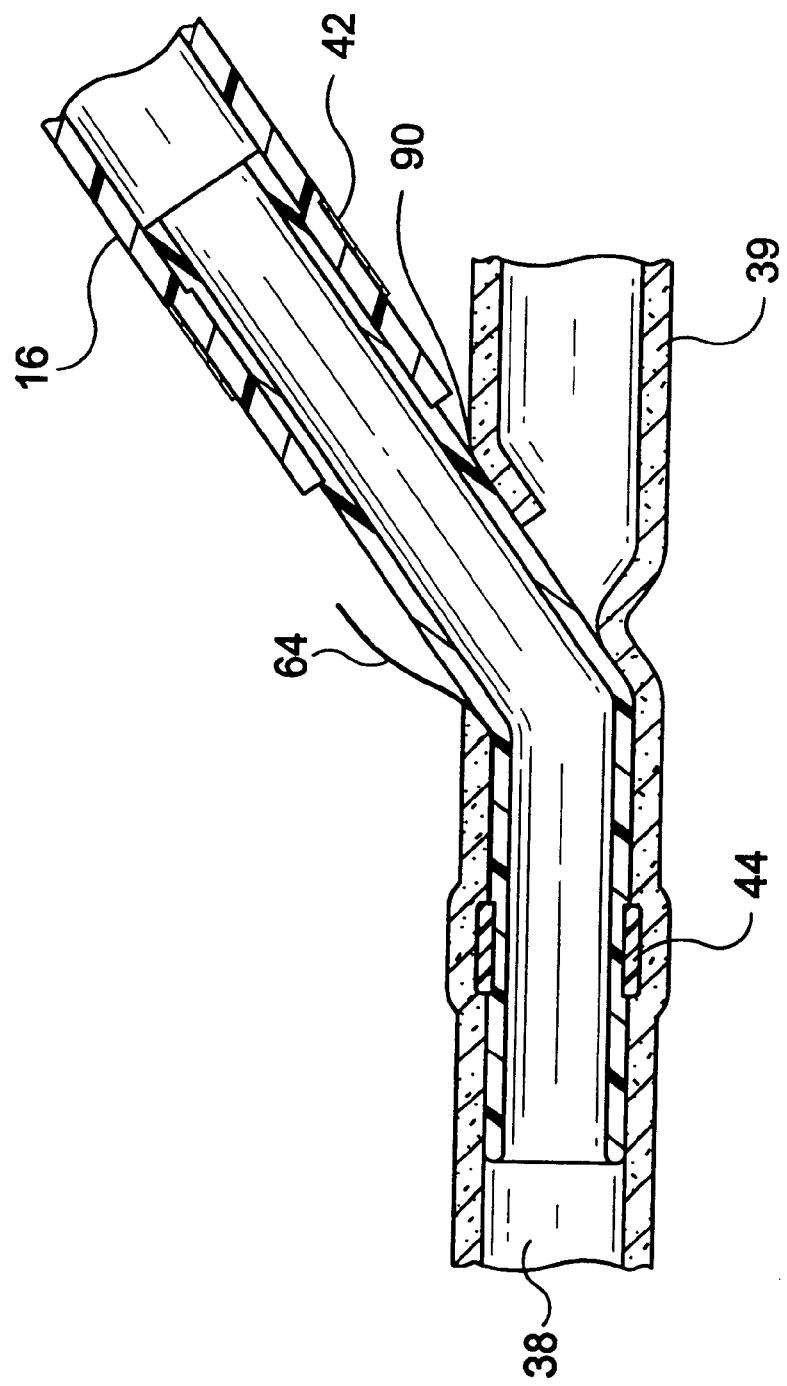
Figure 8C:
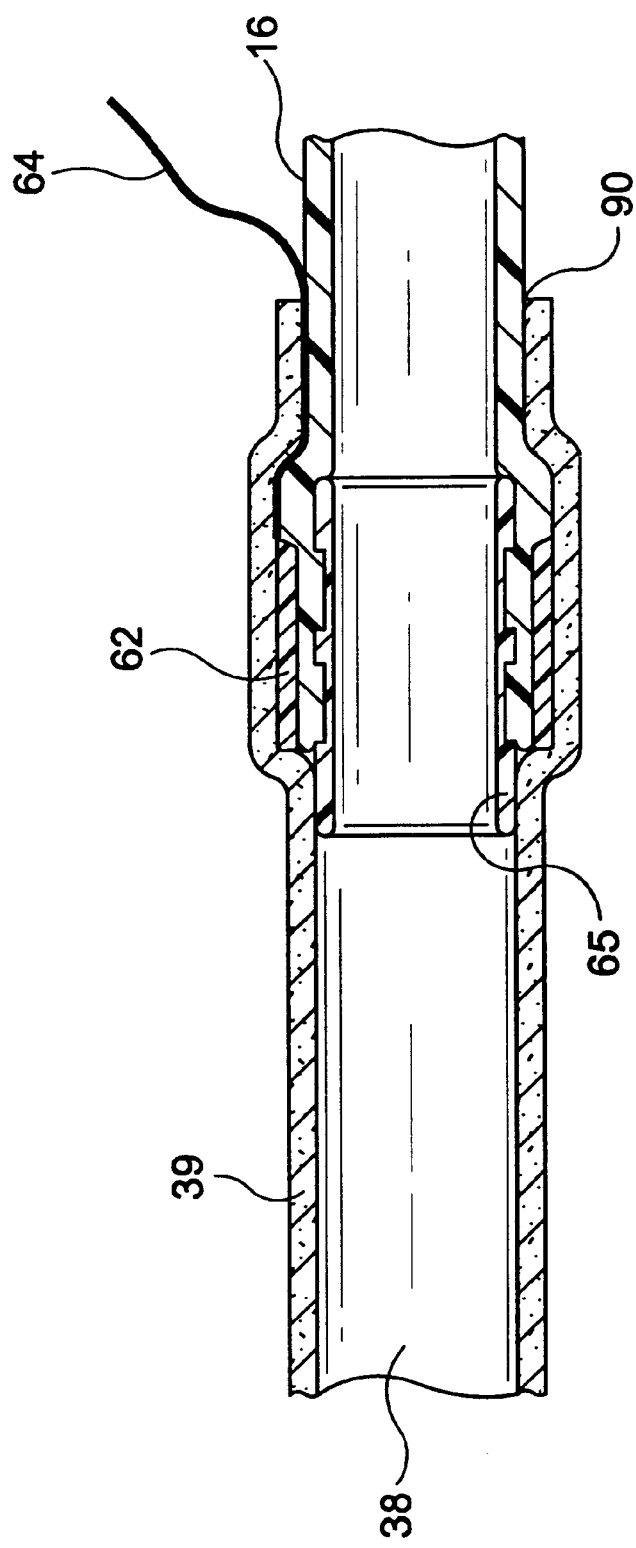
Figure 8D:
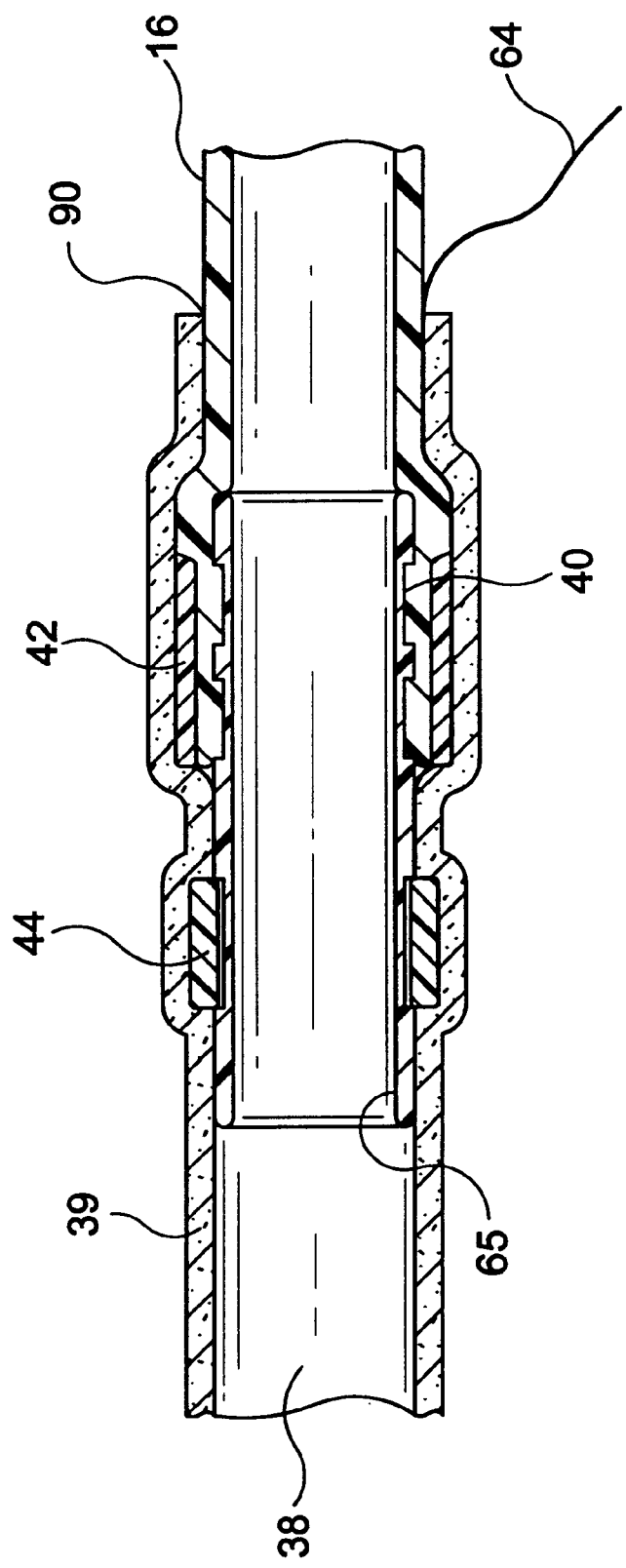

The bypass graft fittings are constructed from a metal (e.g. titanium), alloy (e.g. stainless steel or nickel titanium), thermoplastic, thermoset plastic, silicone or combination of the aforementioned materials into a composite structure; other materials may also be used. The fittings may be coated with materials such as paralyne or other hydrophilic substrates that are biologically inert and reduce the surface friction. Alternatively, the fittings may be coated with heparin or thrombolytic substances designed to prevent thrombosis around the attachment point between the bypass graft and the host vessel. The fittings consist of one or more components designed to secure a bypass graft to the fitting and the fitting to the host vessel wall for a fluid tight bond between the bypass graft and the host vessel. The fittings may be used at end-to-end anastomoses for applications where retrograde blood flow is not essential (e.g. total occlusions) as shown in FIGS. 2c and 8a; end-to-side anastomoses for medium and small diameter vessels (e.g. peripheral vessels and coronary vessels) where retrograde blood flow is essential as shown in FIG. 19c; and end-to-side anastomoses for large diameter vessels (e.g. the aorta) as shown in FIG. 18a. The end-side fittings may be configured to orient the bypass graft at an angle, A, relative to the host vessel ranging between approximately 30 and 90 degrees. This helps optimize fluid flow through the bypass graft.

Figure 3A:
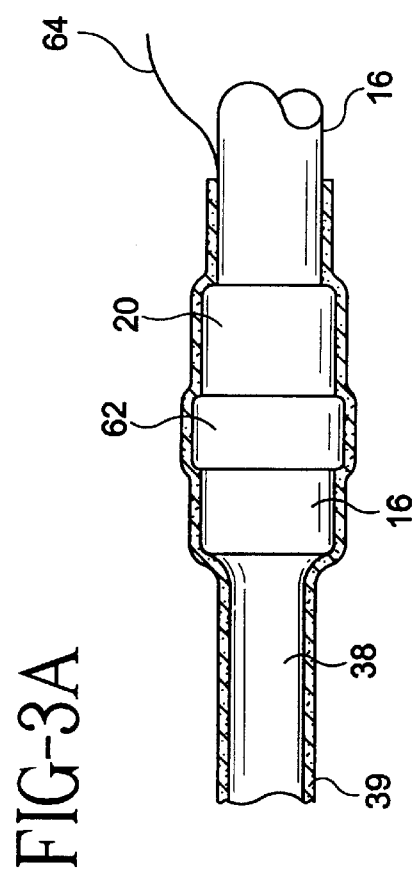

FIGS. 3a–c show an end-end fitting 20 designed to secure bypass grafts constructed from an internal mammary artery, radial artery, saphenous vein, or other harvested vessel such that only the endothelial layer of the bypass graft is exposed to blood flow. In FIGS. 3a–c, the bypass graft 16 is fed through the interior of the fitting and is wrapped around the distal end. A grasping tool may be used to pull the bypass graft through the fitting, especially when using long fittings. An everting tool may be used to wrap the bypass graft around the fitting prior to securing the bypass graft to the fitting. After the bypass graft is everted around the fitting, a retaining ring 62 is positioned over the everted bypass graft to compress it against the fitting. This secures the bypass graft to the fitting. The retaining ring 62 is connected to a signal wire 64 that is routed to a radiofrequency generator to deliver radiofrequency energy to the retaining ring 62 for thermal securing of the fitting to the host vessel 38.

Figure 4B:
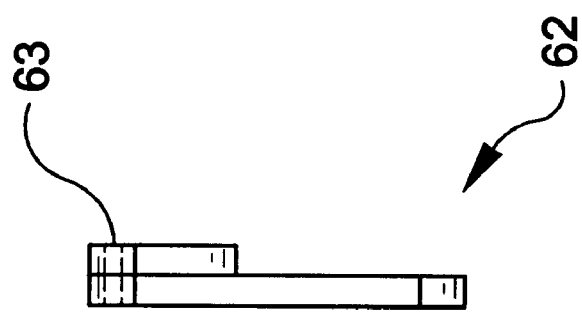
FIGS. 4a–i show retaining rings used to bond the bypass graft to the fitting and/or the fitting to the vessel wall.
Figure 4A:
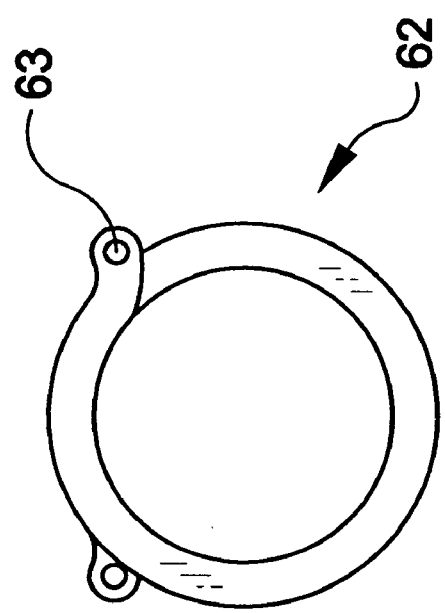
Figure 4D:
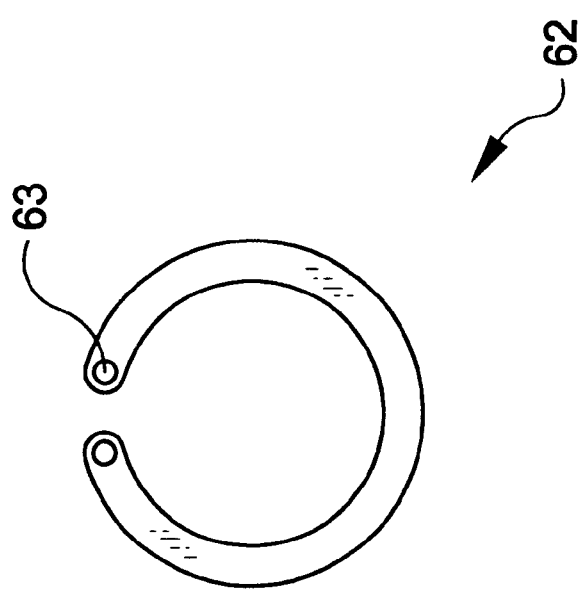
Figure 4C:
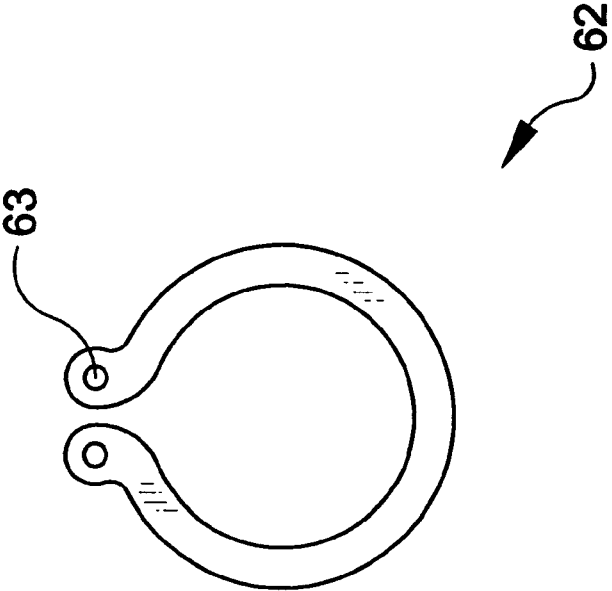
Figure 4F:
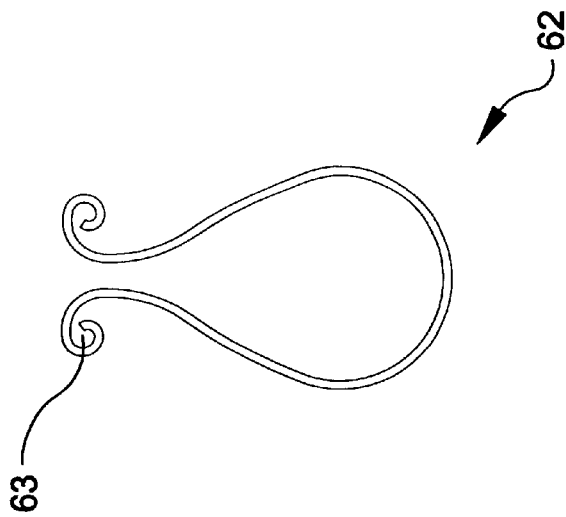
Figure 4E:
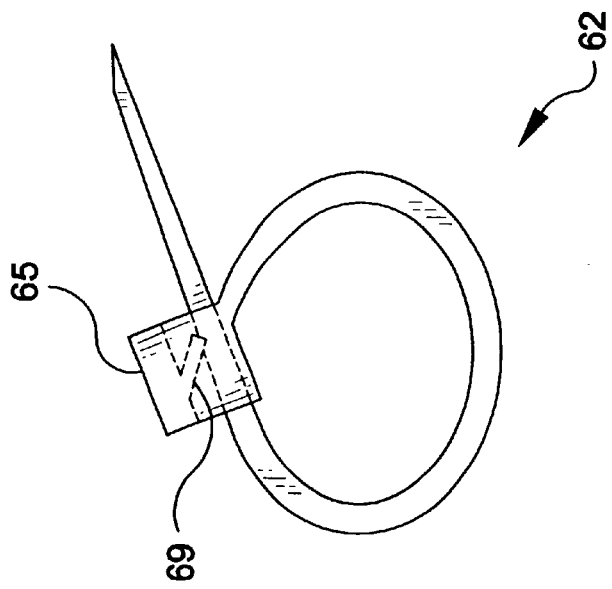

FIGS. 4a–i show embodiments of the retaining ring 62 used to secure the bypass graft 16 to the fitting. The retaining rings may be fabricated from a metal, alloy, thermoplastic material, thermoset, composite of these materials, or other material. However, the retaining rings must permit at least 30% enlargement in diameter without becoming permanently deformed. Thus, after placement, the retaining ring will compress around the bypass graft and fitting interface to form a secure seal. In FIGS. 4a–f, the retaining ring is a preshaped member having a rectangular, circular, or elliptical cross-section and eyelets 63 that facilitate positioning the retaining ring over the fitting and may be used to suture the retaining ring closed for additional support. The retaining ring shown in FIGS. 4a–b has a preshaped member wound beyond a single turn. When the eyelets 63 are squeezed together, the diameter of the retaining ring enlarges making it easier to position over the bypass graft and fitting combination. In FIGS. 4c–d, the retaining ring 62 is a coiled wire extending to just less than a single turn. When the eyelets 63 are spread apart, the diameter of the retaining ring enlarges.

Figure 4H:
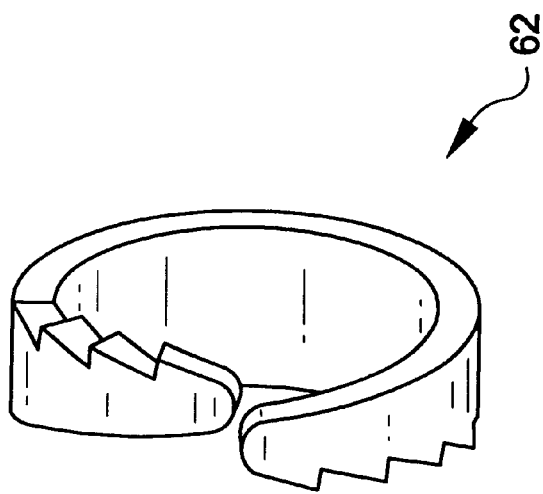
Figure 4G:
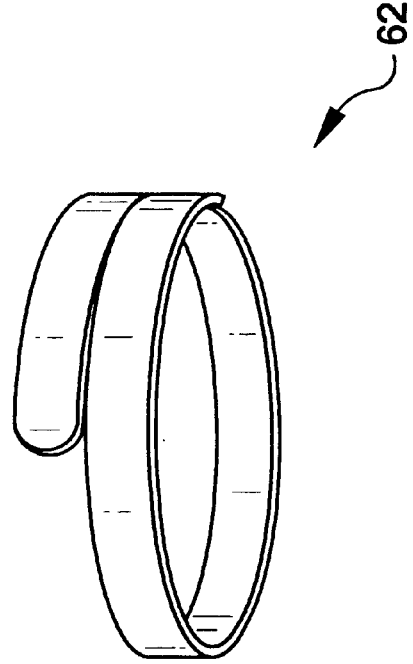
Figure 5A:
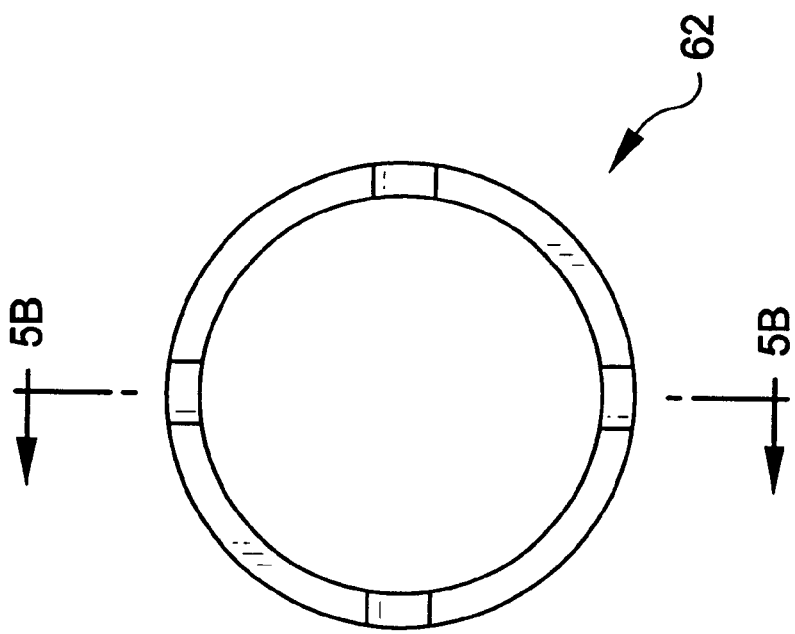
FIGS. 5a–e show retaining ring embodiments that act as electrodes for thermally securing the fitting to the host vessel wall.

The retaining ring 62 shown in FIG. 4g is a preshaped member wound beyond a single turn and having radiused edges and ends. One representative fabrication process for the preshaped retaining ring involves forming the raw material into a desired geometry and exposing the material to sufficient heat to anneal the material into this predetermined shape. This process applies to metals (e.g. nickel titanium) and polymers. The preshaped retaining ring configuration is expanded by inserting the expansion tool into the middle of the retaining ring and opening the expansion tool thereby enlarging the diameter of the retaining ring. Once the retaining ring is positioned, the force causing the retaining ring to enlarge is removed causing the retaining ring to return towards its pre-formed shape thereby compressing the bypass graft over the fitting. This retaining ring may also be used to secure a fitting to a host vessel since this retaining ring may be expanded to expose an opening between opposite ends adapted for placement over the host vessel. Once positioned over the host vessel to fitting interface, the retaining ring is allowed to return towards its preformed shape thereby compressing the host vessel against the fitting.

Figure 4I:
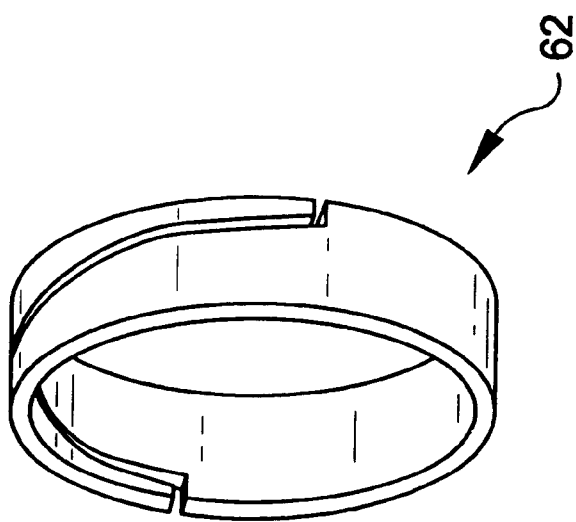

The retaining rings may incorporate elastic memory characteristics. For example, a retaining ring shown in FIG. 4g, may be manufactured from a deformable material and crimped over the bypass graft to fitting interface or host vessel wall to fitting interface for securing purposes. FIG. 4h shows another retaining ring that does not incorporate elastic memory characteristics. This retaining ring is opened for positioning around the bypass graft to fitting interface or the host vessel to fitting interface and is closed thereby causing the teeth to engage and lock the retaining ring in the closed position. Further closing the retaining ring causes the diameter to decrease and increase compression. FIG. 4i shows another retaining ring 62 configuration having a preshaped member wound beyond a single turn. This embodiment also permits expansion of the retaining ring to facilitate positioning, but is configured to form a complete ring in its resting shape.

Figure 5C:
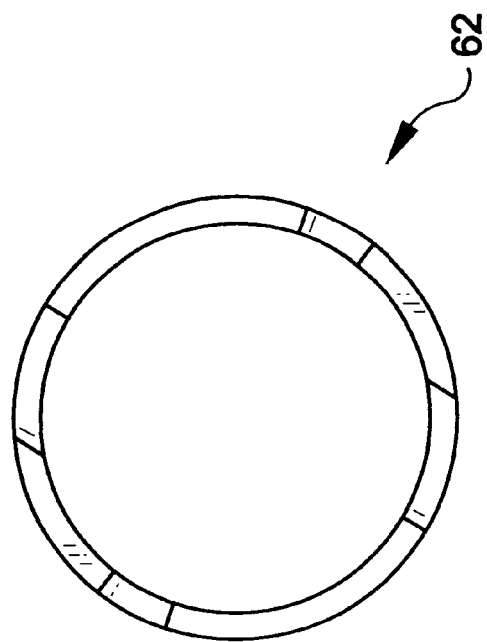
Figure 5B:
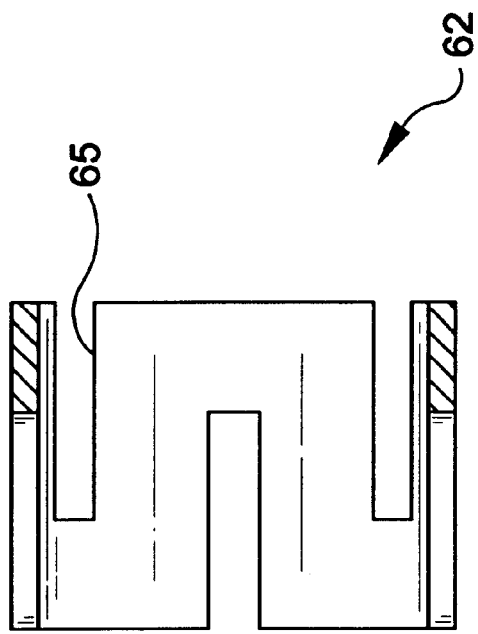
Figure 5E:
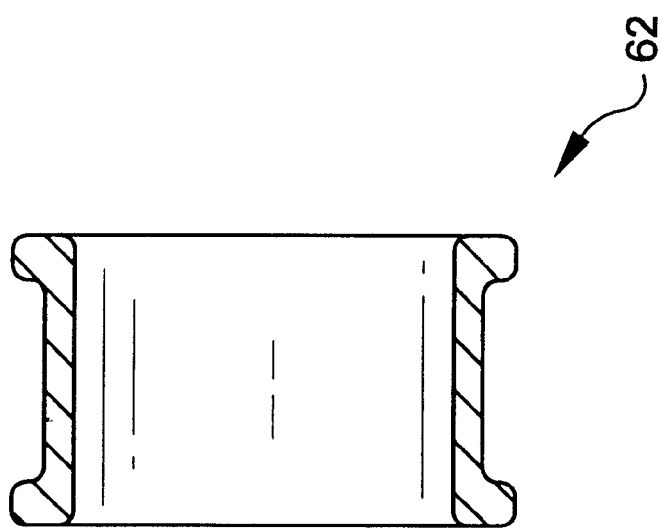
Figure 5D:
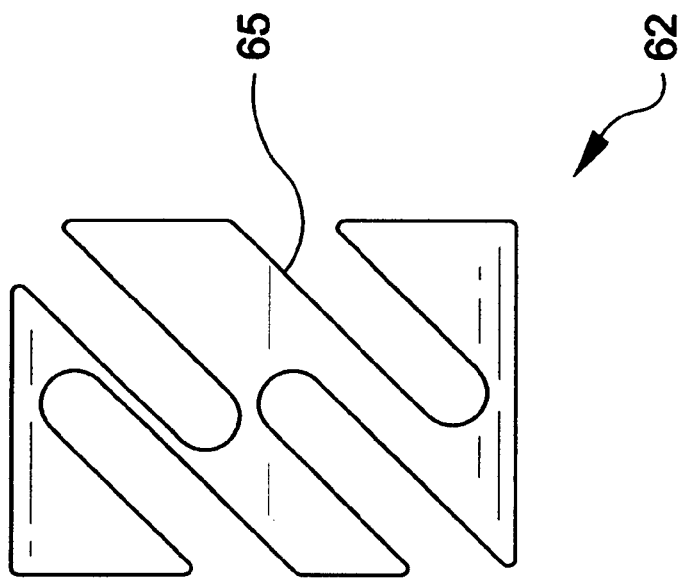

FIGS. 5a–e and FIGS. 6a–f show retaining rings 62 which are particularly useful when utilizing the thermal securing process in attaching a bypass graft and fitting to a host vessel. The retaining rings 62 may be embedded in the bypass graft when using synthetic materials or advanced over the bypass graft and fitting interface to produce an interference fit at the bond joint. The retaining rings 62 shown in FIGS. 6a–d may be enlarged while being deployed around the bypass graft and fitting combination and allowed to return to its preformed shape, once positioned, thereby securing the bypass graft to the fitting and providing a fluid tight seal. The retaining rings 62 have numerous edges 65 including straight notches as shown in FIG. 5b, slanted notches as shown in FIG. 5d, holes through the retaining ring, spaces defined by mesh material, or other geometry forming edges. The edges 65 produce high current densities when radiofrequency energy is transmitted through the retaining rings. The retaining ring electrodes have several spaces into which the vessel can shrink and coagulum can infiltrate thereby providing adherence between the host vessel and the retaining ring 62. The retaining rings 62, shown in FIGS. 6e–f, incorporate petals 67 so that an end-to-end fitting may be used for an end-to-side anastomosis.

The bypass graft may be bonded to the fittings prior to securing the fittings to the host vessel. This step may be performed outside the patient to allow the physician to ensure a strong and leak resistant bond. Another advantage of the fittings is that they only expose the endothelial layer of a biological bypass graft to blood flow which generally prevents thrombosis and other interactions between foreign materials and blood.

Conventional anastomosis techniques require a relatively large incision through the vessel wall and use of sutures, commercially available clips, or stapling devices to bond the end of the bypass graft to the exposed edges of the vessel wall. In certain cases, the structural integrity of the vessel wall may be weakened causing the vessel to collapse at the anastomosis site, especially when the bypass graft is not appropriately aligned to the host vessel incision. Therefore, the delivery system embodiments are designed to access the vessel through a small puncture in the vessel wall. The delivery systems are designed to prevent excess blood loss when accessing the host vessel and deploying the bypass graft and fitting combination thereby eliminating the need to stop or re-route blood flowing through the host vessel. This approach also generally improves the leak resistance around the fitting due to elastic compression of the vessel wall around the fitting and aligns the bypass graft to the host vessel wall at the anastomosis site.

The particular delivery system embodiment used depends on the application. For catheter-based bypass grafting applications, further referenced in U.S. application Serial No. 08/966,003 filed Nov. 7, 1997, a catheter (e.g. guiding member) is intralumenally advanced to the proximal anastomosis site. A puncture device (e.g. needle) is used to perforate the vessel wall and enable advancing a guiding member exterior to the vessel. A dilating member expands the opening to atraumatically advance the guiding member through the vessel wall. A balloon may be attached to the guiding member and inflated to restrain the guiding member outside the host vessel and to prevent leaking at the puncture site. The balloon is deflated while the guiding member is advanced through the vessel wall. The catheter is then manipulated to the distal anastomosis site. The puncture device is used to perforate the vessel wall and access the interior of the vessel at the distal anastomosis site. A guidewire may be advanced through the puncture device or the puncture device may function as a guidewire to provide a passage to advance the guiding member into the interior of the host vessel at the distal anastomosis site. Once the guiding member is advanced through the puncture and into the interior of the host vessel, the bypass graft is advanced inside or outside the guiding member to the distal anastomosis site. A stylet may be used to advance the bypass graft along the guiding member or maintain the position of the bypass graft as the guiding member is retracted. The balloon attached to the guiding member may again be inflated to keep the guiding catheter within the vessel at the distal anastomosis site and prevent leaking. The bypass graft is secured to the host vessel at the distal anastomosis site. The guiding member may be retracted so the bypass graft is able to contact the host vessel wall at the proximal anastomosis site. If a balloon was inflated to maintain the position of the guiding member within the vessel, it must be deflated prior to retracting the guiding member through the vessel wall. The bypass graft is then secured to the host vessel wall at the proximal anastomosis site and the guiding member is removed leaving the bypass graft as a conduit for blood to flow from the proximal anastomosis to the distal anastomosis. The fittings used to secure the bypass graft to the host vessel wall at the proximal and distal anastomosis sites depend on the application and whether retrograde blood flow through the anastomosis site is desired. Some fittings used for end-to-end anastomoses may not permit retrograde blood flow.

Figure 7B:
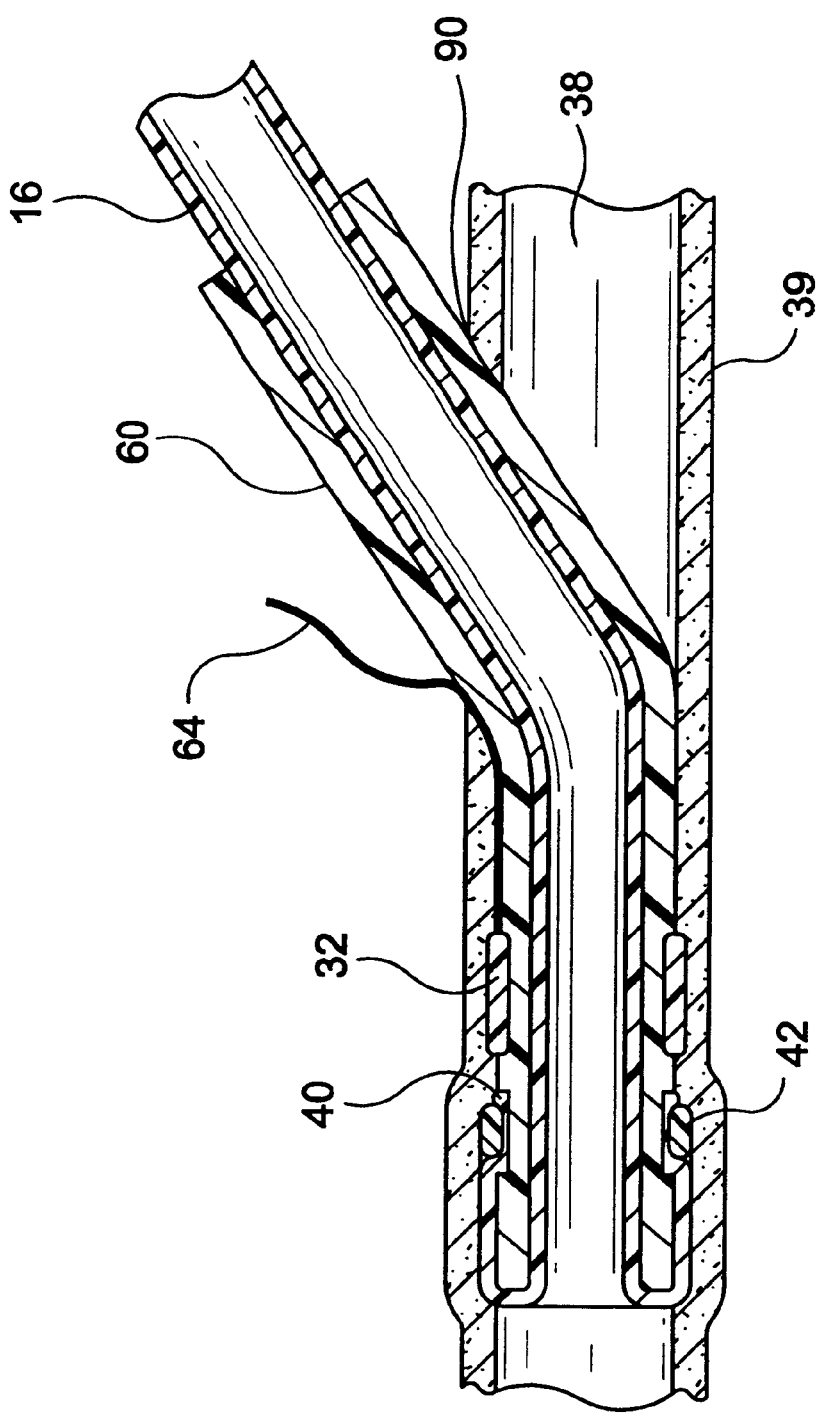

FIGS. 7a–b show fittings 60 attached in-line along a vessel 38. The fittings 60 are designed to support the bypass graft at the vessel wall insertion site 90 and prevent the host vessel 38 from constricting the diameter of the bypass graft 16. The bypass graft 16 is advanced through the fitting 60 and is everted around the distal end of the fitting 60. A retaining ring 42 is used to secure the bypass graft 16 to the fitting 60 and is positioned within the notched region 40.

The bypass graft may be secured to the vessel by transmitting radiofrequency energy to electrodes 44 attached to the bypass graft 16. The electrodes 44 may be conductive fittings or retaining rings bonded to the bypass graft as previously described. The electrodes 44 may be fabricated from stainless steel, nickel titanium, platinum, platinum iridium, gold, titanium, tungsten, tantalum, or other material and may provide structural support to the bypass graft. Electrodes 44 may be incorporated into the fittings to thermally secure the fitting and the bypass graft to the vessel wall at each anastomosis. The retaining rings may serve to bond the bypass graft to the fitting and act as the electrodes for thermal securing. Alternatively, the electrodes may be added to the fitting as separate components aside from the retaining rings. When fittings are laminated within layers of synthetic bypass graft material eliminating the need for retaining rings, the electrodes will be bonded to the fittings or bypass graft during manufacturing. These end-to-end fittings are particularly useful when performing in-line anastomoses along a vessel and around a vascular abnormality. They are also useful to treat total occlusions when retrograde blood flow is not beneficial.

For surgical applications, physicians may access the anastomosis sites from the exterior surface of the host vessel. Unlike the catheter-based approach where the bypass graft is advanced past the distal end of the delivery catheter during deployment, the delivery system of the surgical approach must permit removal after both ends of the bypass graft have been secured and the delivery system resides around the attached bypass graft.

FIGS. 8a–d show that the bypass graft 16 does not need to be everted. For example, synthetic bypass grafts may be attached to the exterior of the fitting 65. The fitting 65 may be laminated between layers of the bypass graft 16.

Figure 9A:
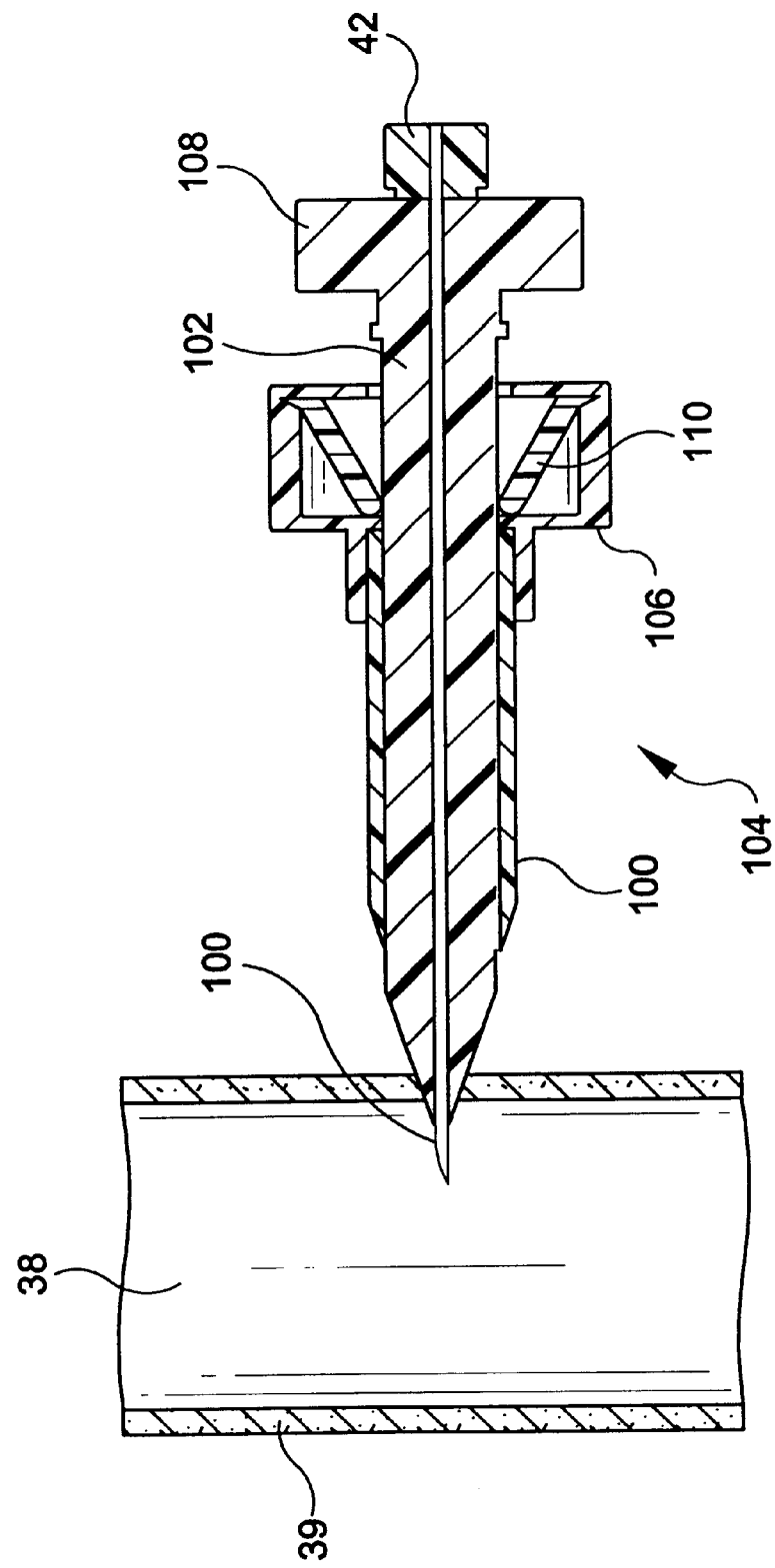
FIGS. 9a–c show a delivery system.
Figure 9B:
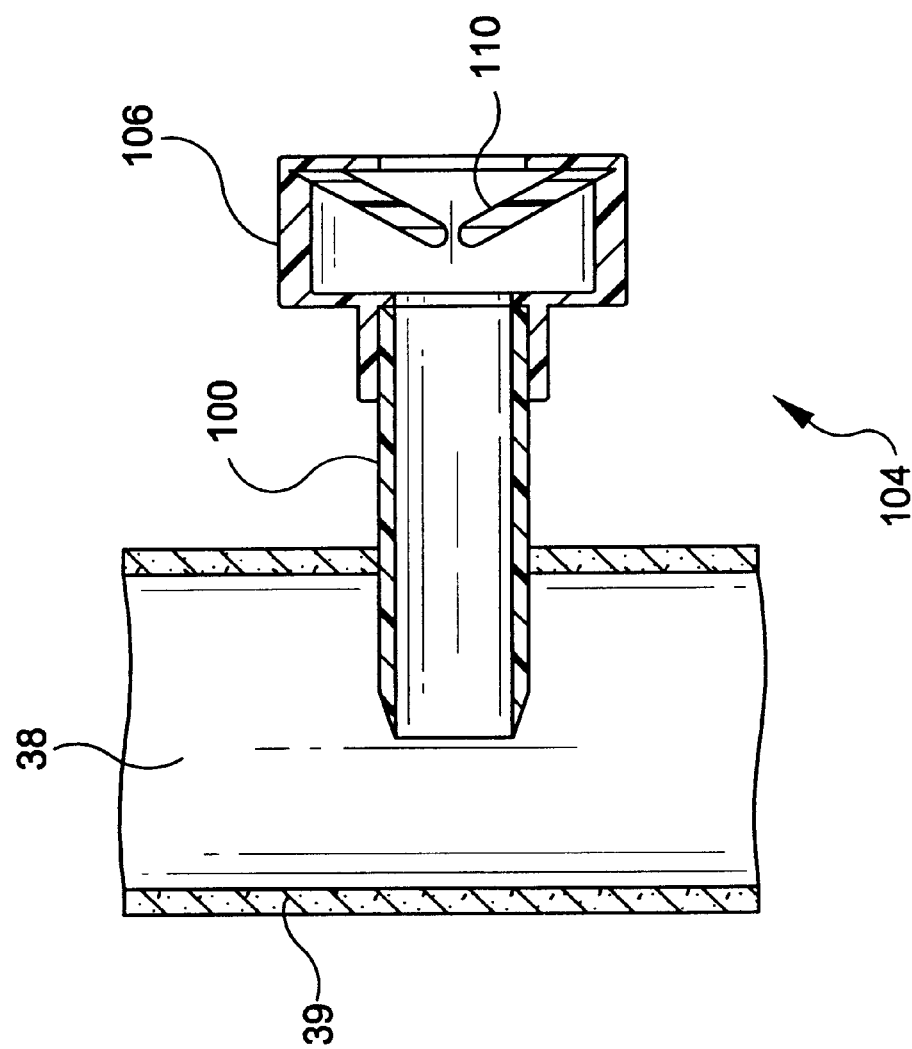
Figure 9C:
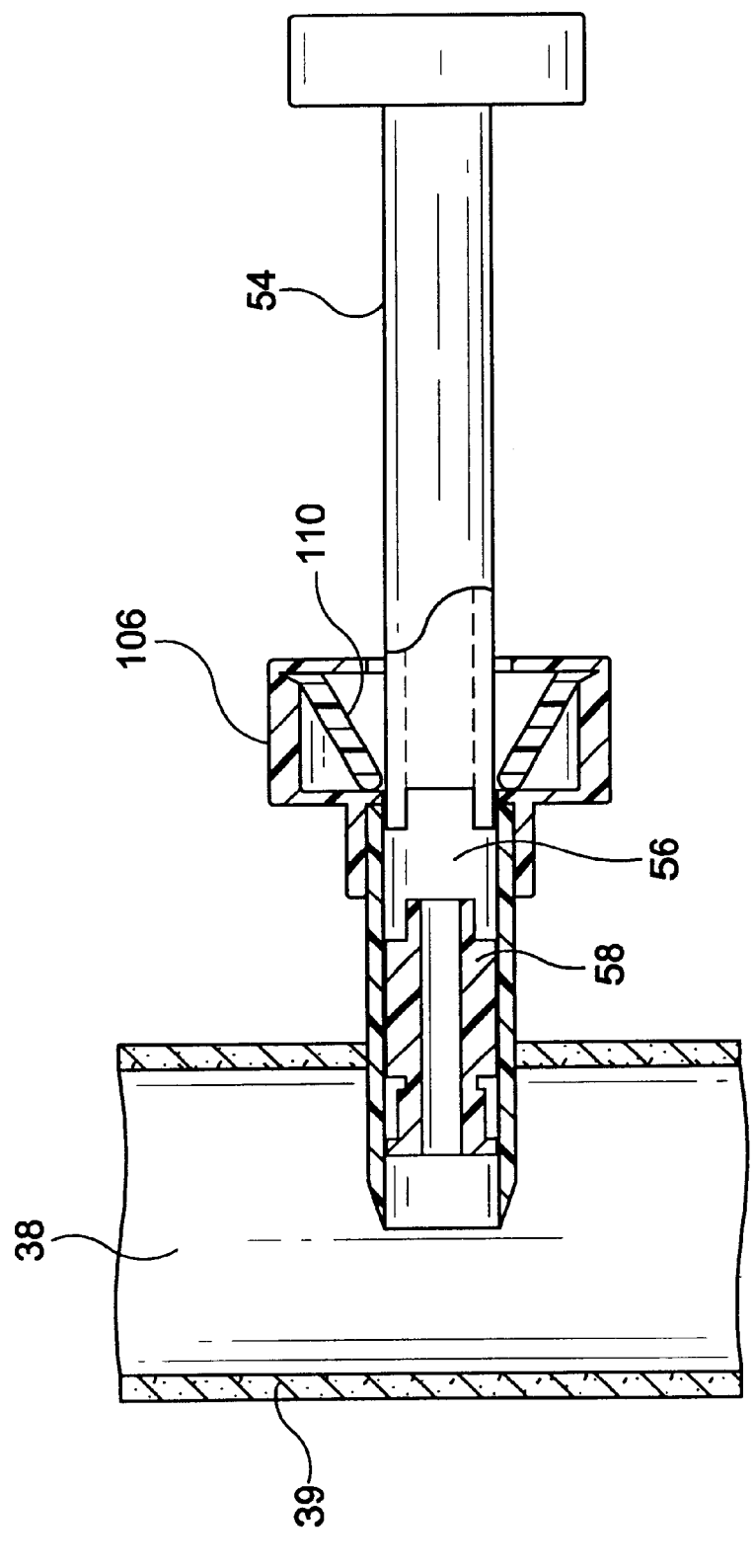

FIGS. 9a–c show steps to position a bypass graft and fitting combination through a vessel wall 39. A needle 100 is inserted through a dilator 102 and a sheath 104. The needle, dilator, and sheath combination is positioned at the target vessel location. Especially for minimal access procedures involving endoscopic visualization and manipulation through small incisions, sensors may be incorporated in the needle, dilator, and/or sheath to position the delivery system at the target location. The sensors can include ultrasonic transducers, such as those fabricated from piezoelectric material, doppler crystals, infrared transducers, or fiberoptics. Alternatively a lumen may permit the injection of radiopaque contrast material within the vessel to verify the position using fluoroscopy.

FIG. 9a illustrates needle 100 being used to puncture the vessel wall 39 and advancing into the interior of the vessel 38. The needle 100 may be designed with a tapered or stepped distal end to restrict movement of the needle beyond the end of the dilator 102 and prevent perforating the opposite side of the vessel or unwanted anatomy. A guidewire (not shown) may be advanced through the needle to provide a path over which the dilator and sheath may be advanced. When using a guidewire, the needle may be retracted to prevent unwanted perforations or abrasions to the vessel or adjacent anatomy. The dilator 102 is then advanced over the needle 100 or guidewire into the host vessel. Subsequently, the needle 100 (if not already retracted to insert the guidewire) may be removed from the vessel or retracted inside the dilator 102. The dilator 102 is tapered to provide a smooth transition when advancing through the vessel wall 39. The vessel wall 39 forms a seal around the dilator 102 to preventing excess blood leakage from the vessel. A sheath 104 having a radius or tapered distal end forms a smooth transition around the dilator 102. Once the dilator 102 is positioned within the vessel 38, the sheath 104 may be advanced over the dilator 102 and into the vessel 38 as shown in FIG. 9b. At this point, the dilator 102 may be removed. Insertion of a sheath 104 into a vessel 38 over a dilator 102 and needle 100 is commonly used by physicians when performing the Seldinger technique during catheterization procedures or inserting I.V. catheters into veins for withdrawal of blood or introduction of medicines. The sheath 104 and dilator 102 may be constructed from polyethylene, or other polymer and be extruded or molded into a tube. The sheath 104 and dilator 102 may incorporate a braided layer laminated between two polymers to resist kinking and improve the column strength and torque response. A taper and radius may be formed in the distal end of the dilator and sheath by thermally forming the raw tubing into the desired shape.

The hub 106, 108 on the sheath 104 and dilator 102, respectively may be fabricated from polycarbonate, polyethylene, PEEK, urethane or other material and be injection molded, adhesively bonded, or thermally bonded to the tube. The hub 106 contains at least one and preferably two grooves, slits, or series of perforations along the hub to enable the operator to split the hub when removing the sheath from around the bypass graft. The hub 106 houses a hemostatic valve 110 constructed of silicone or other material having a large percent elongation characteristic. The hemostatic valve 110 prevents excess blood loss through the sheath when positioned into the vessel. The valve 110 also incorporates at least one groove, slit, or series of perforations to permit separation when tearing the sheath from around the bypass graft. A side port may be included to aspirate and flush the sheath. The hub may alternatively be a separate piece from the tear-away sheath and be independently removed from around the bypass graft. This hub may include a luer fitting to enable screwing onto a mating piece of the tear-away sheath, or other mechanism to permit removable attachment of the hub to the tear-away sheath. This hub may incorporate at least one groove, slit, or series of perforations to enable splitting the hub to form an opening to remove the hub from around the bypass graft. Alternatively, the hub may include a slot which may be closed to prevent fluid leaking and may be aligned to form an opening for removal from around the bypass graft.

The needle 100 and dilator 102 may incorporate a number of additional features to facilitate positioning at the host vessel. For example, a number of sensors may be placed within the tapered region of the dilator such that they face axially or laterally with respect to the axis of the dilator lumen. As a result, imaging modalities may be directed forward or around the periphery of the dilator. For both configurations, the sensors may be oriented around the dilator 102 at known angular increments. Sensors used to position the delivery system include ultrasonic transducers, such as those fabricated from piezoelectric material, infrared transducers, or fiberoptics. For example, four ultrasonic transducers may be placed around the dilator 102 separated by 90 degrees to provide a 3-dimensional interpretation of anatomic structures in front of the dilator to better detect the host vessel. Conventional phased array imaging modalities may be used to derive images extending distal to the dilator 102 or around the circumference of the dilator 102. Sensors may be placed at the distal end of the needle 100 to facilitate positioning the needle at vessel location. The sensors may be used with the dilator sensors to provide better imaging resolution and determine the location of the needle tip relative to the end of the dilator 102.

Another feature which may be used in the dilator 102 and needle 100 is the inclusion of unidirectional or bi-directional steering. A steering mechanism may be positioned within the sheath, dilator, and/or needle. Typically, the steering mechanism may include a pull-wire terminating at a flat spring or collar in the sheath, dilator, or needle. The steering system has a more flexible distal section compared to the proximal tube body. When tension is placed on the pullwire, the sheath, dilator, or needle is deflected into a curve which helps direct the delivery system to the target vessel location. The pullwire may be wound, crimped, spot welded or soldered to the flat spring or collar placed in the sheath or dilator. This provides a stable point within the sheath or dilators for the pullwire to exert tensile force thus steer the sheath or dilator. To incorporate steering in the needle, the pullwire may be spot welded or soldered to one side of the needle hypotubing. The proximal tube body of the sheath or dilator may be reinforced by incorporating a helically wound wire within the tube extrusion to provide column support from which to better deflect the distal section.

Figure 10:
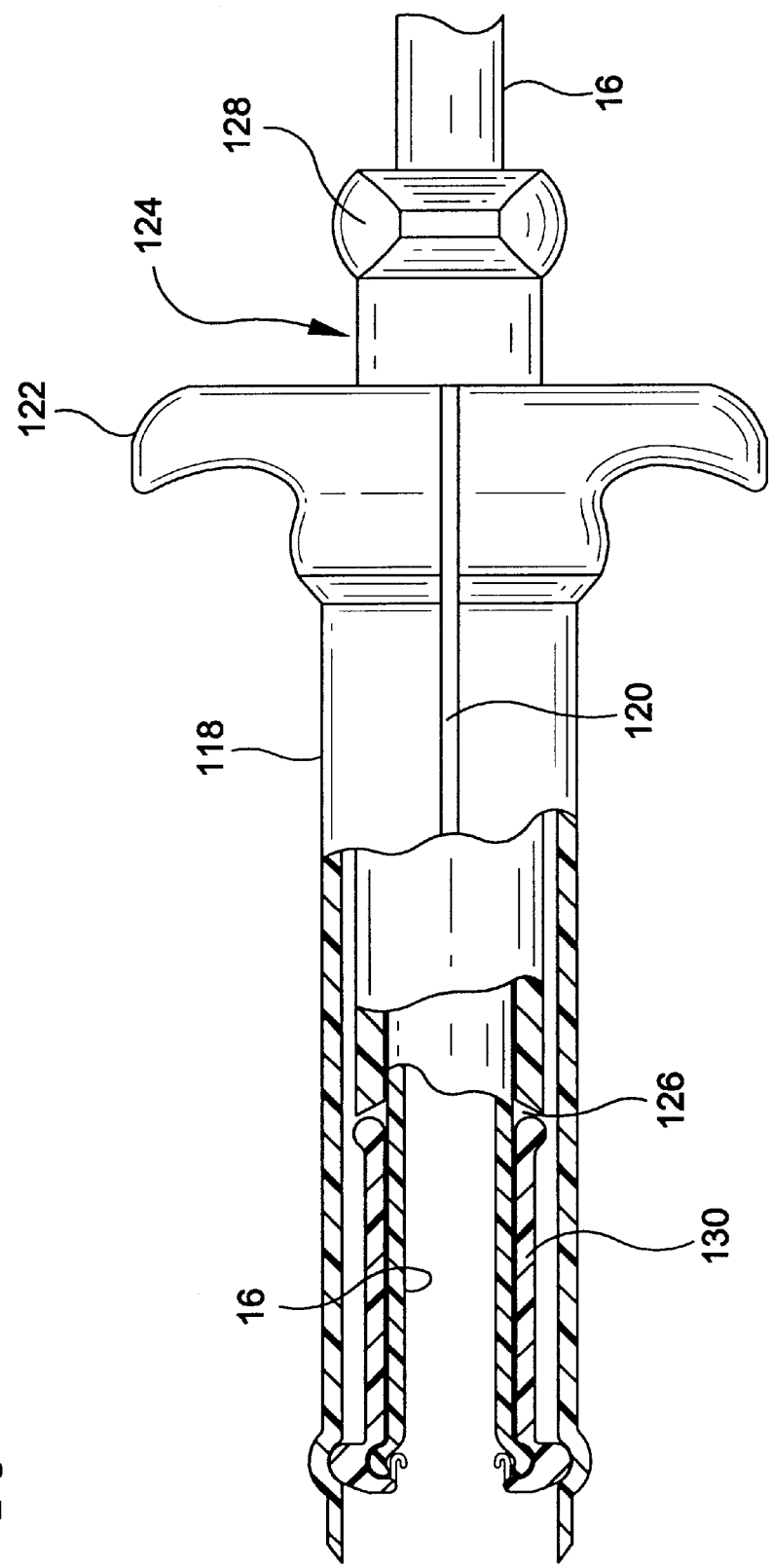
FIG. 10 shows a delivery system.

FIG. 10 shows sheath 118 with at least one groove 120, slit, or series of perforations formed along the tube and hub 122 to provide a tear-away mechanism along at least one side for use after securing the bypass graft to the vessel wall. Alternatively, the sheath 118 may include a section of tubing material pre-split into at least two sections such that the tubing tends to continue to split into two pieces as the sections are pulled apart. This feature is essential for removal of the sheath 118 from around a bypass graft 16 when the sheath 118 is unable to slide past the opposite end of the bypass graft 16. Support material incorporated into a tear-away sheath to improve column strength should split along the grooves formed in the sheath. The support material may be fabricated into two braided sections oriented on opposite sides of the sheath such that the grooves reside along the spaces between the braided sections. Alternatively, the supporting material may be strands of wire (e.g. stainless steel, nylon, etc.) laminated between layers of sheath material and oriented axially along the longitudinal axis of the sheath. The tear-away sheath 118 may further incorporate features to maintain blood flow through the host vessel while positioned inside the lumen of the host vessel as further referenced in FIGS. 28a–b.

The plunger 124 is designed to insert the bypass graft 16 and fitting 130 as an attached unit and includes a lumen to pass the bypass graft 16 through while inserting the fitting 130 into the host vessel. A plunger 124 is essential when inserting biological bypass grafts or synthetic bypass grafts that do not have adequate column strength to be pushed through the hemostatic valve of the sheath. In addition, the plunger 124 protects the bypass graft during insertion through the hemostatic valve of the sheath. After one side of the bypass graft is placed at a first vessel location, the plunger 124 must be removed. The plunger 124 may be retracted beyond the opposite end of the bypass graft, if possible, or the plunger 124 may be split along at least one groove 120, 126 incorporated along the side of the plunger. The plunger 124 is used to insert the opposite end of the bypass graft, attached to a fitting, through a second sheath inserted at a second vessel location. After attaching the second end of the bypass graft to the vessel, the plunger 124 is contained between the ends of the attached bypass graft and must be removed by tearing the plunger along at least one and preferably two grooves 120, 126. The tear-away groove 120, 126 must permit splitting the plunger wall and hub 128 along at least one side to remove the plunger 124 from around the bypass graft. To facilitate removal from around the bypass graft, the plunger 124 and tear-away sheath 118 discussed above preferably incorporate grooves, slits, or perforations 126 on two sides to enable separation into two components.

Figure 11:
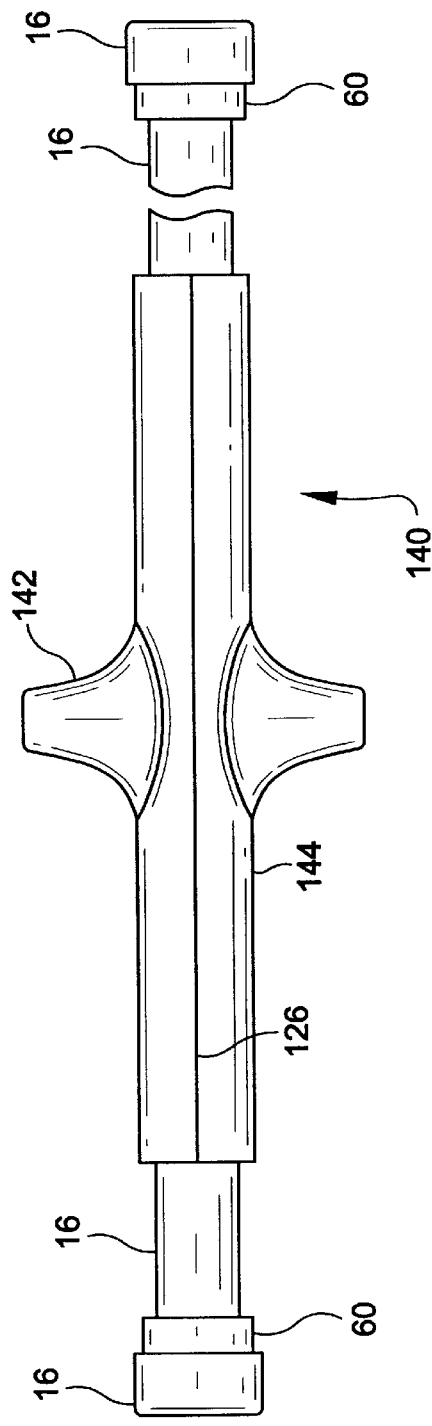
FIG. 11 shows a two-way plunger used to deliver the bypass graft and fitting combination through the sheath and into the host vessel.

FIG. 11 shows a bypass graft assembly containing fittings 60 already attached at the bypass graft 16 ends and plunger 140 preloaded onto the bypass graft 16. This plunger 140 is designed with the hub 142 located at the middle region to facilitate insertion of both ends of the bypass graft and attached fittings without removal and repositioning of the plunger prior to insertion of the second end of the bypass graft. The plunger 140 has grooves, slits, or perforations 126 along at least one side of the plunger tube 144 and hub 142 to permit removal after positioning and attachment of the bypass graft at both ends.

Figure 12A:
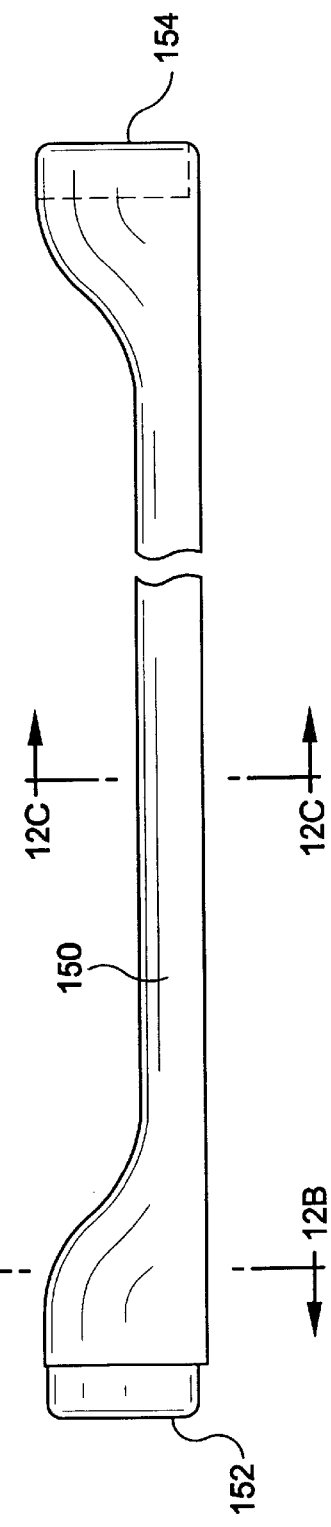
FIGS. 12a–c show an alternative plunger embodiment.
Figure 12C:
Figure 12B:
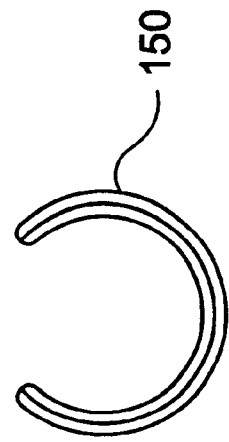

FIGS. 12a–c illustrate another plunger embodiment. Plunger 150 includes an axial slot through its entire length. The slot enables pulling of the plunger 150 from the side of the bypass graft when removing the plunger and permits pressing of the plunger 150 over the side of the bypass graft when placing the plunger over the bypass graft. One end 152 has a short length stepped down to form a smaller outer diameter that fits inside the inner diameter of the fitting and provides a stable anchor to insert and manipulate during delivery of the bypass graft and fitting combination into the vessel. The other end 154 has the inner diameter reamed out and notched for a short length to fit over the outer diameter of the bypass graft and fitting combination during manipulations. The plunger 150 maintains its integrity upon removal from the bypass graft and may be used to deploy multiple bypass graft and fitting combinations through sheaths.

Figure 13:
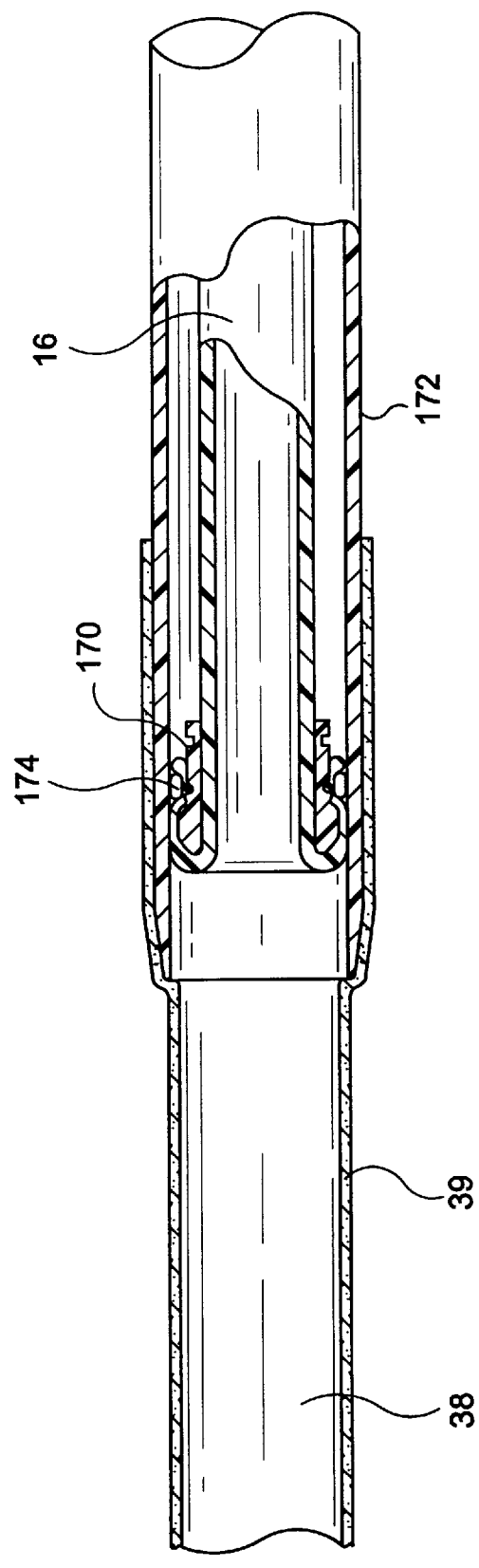
FIG. 13 shows a bypass graft and fitting combination being inserted through a sheath.

FIG. 13 is an enlarged view of sheath 172 inserted into host vessel 39 with dilator removed, and with bypass graft 16 everted about fitting 170 and retained by ring 174.

For situations where blood flow is occluded and an incision has been made through the vessel wall, a modified hockey stick introducer may be used to insert the bypass graft and fitting combination into the host vessel. The hockey stick introducer has a tapered distal end and a partially enclosed body. This introducer is advanced through the incision and is used to expand the vessel wall so the bypass graft and fitting combination may be advanced through the lumen of the introducer and into the host vessel without catching the top part of the fitting on the vessel wall. This is especially important when the bypass graft and fitting combination has an outer diameter larger than the inner diameter of the vessel where the host vessel must be expanded to insert the bypass graft and fitting combination. The introducer may incorporate an extension perpendicular to the longitudinal axis that provides a handle to manipulate the introducer.

Figure 14:
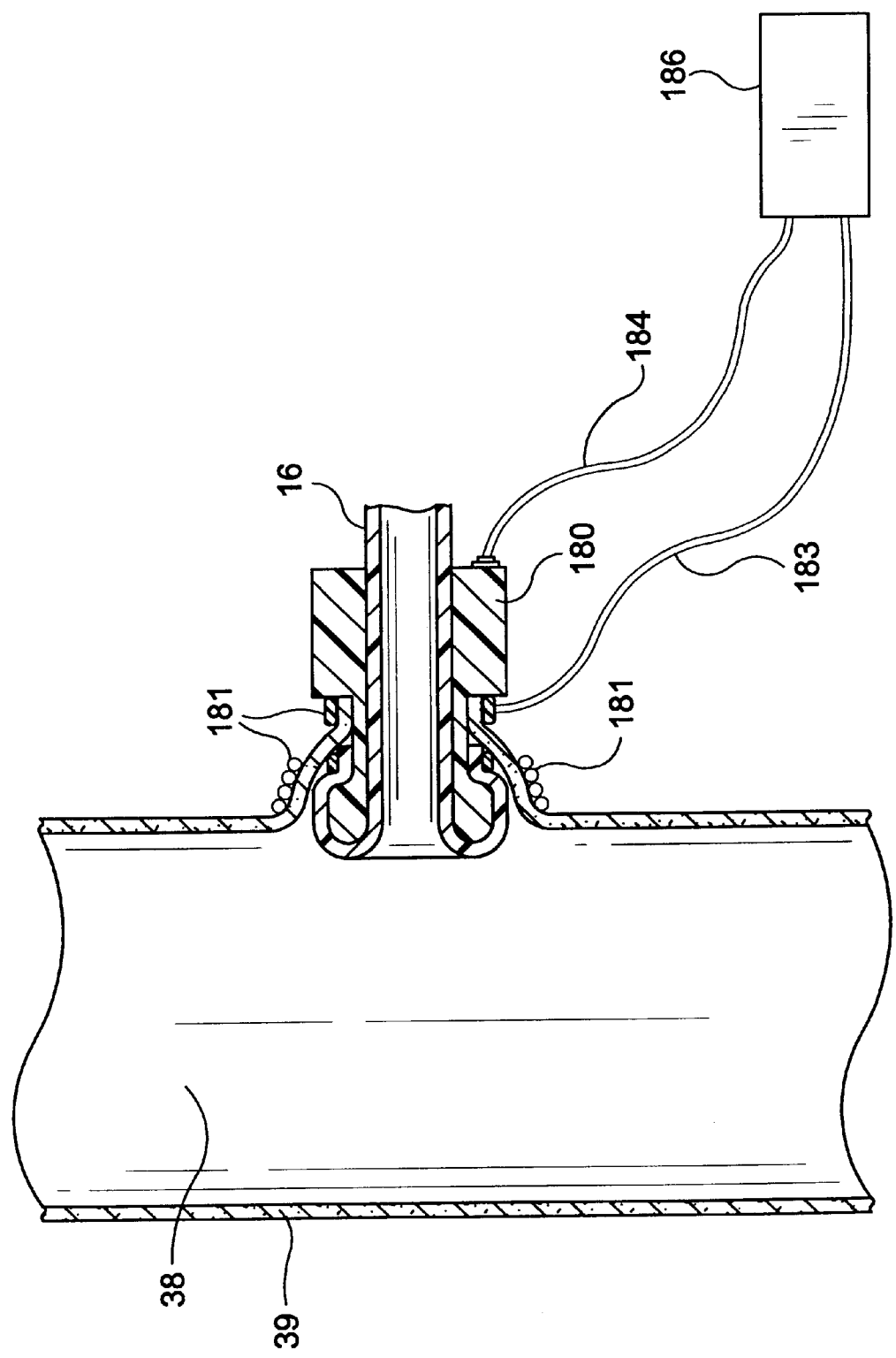
FIG. 14 shows a schematic of the system used to thermally secure a bypass graft to a host vessel wall.

FIG. 14 shows electrodes 181 including conductive material bonded to the bypass graft or fitting 180. The electrodes 181 are used to transmit energy to the vessel wall and may be deposited (e.g. ion beam assisted deposition, sputter coating, pad printing, silk screening, soldering, or painting conductive epoxy) on the fittings 180, bypass graft 16 or retaining ring 182. The electrodes 181 may be flexible and follow the contours of the fittings and/or bypass graft. The electrodes may be formed in a helix, mesh, or braid and bonded to the exterior surface of the fitting and/or bypass graft. Signal wires 183 and 184 are connected to the electrodes through spot welding, mechanical fit, or soldering, and are routed to the leads of a radiofrequency generator 186. A large surface area indifferent ground pad may be placed on the patient's back, thigh, or other location so radiofrequency energy may be delivered in a unipolar configuration. Alternatively, energy may be delivered between electrode pairs in bipolar configuration.

By delivering radiofrequency energy to the electrodes, tissue contacting the electrodes heats and coagulates the vessel wall to the electrode and provides a secure, leak resistant bond. A dramatic increase in impedance results from the formation of coagulum on the electrode. This measurement of the bond strength can be used to determine the quality of the bond generated between the electrode 44 and the vessel wall 39. Different impedance thresholds may specify different degrees of thermal bonding. Initial thermal bonding has been demonstrated during experimental studies when impedance increased above 300Ω using a signal frequency of 500 kHz, which represented a threshold approximately 50% above baseline. The baseline impedance differs depending on the frequency of the signal and the surface area of the electrode; these characteristics must be taken into account when determining the thresholds. Commercial electrosurgical generators operating at a frequency of approximately 500 kHz commonly measure impedances up to and exceeding 1 kΩ when producing complete hemostasis using tissue coagulating probes.

Figure 15B:
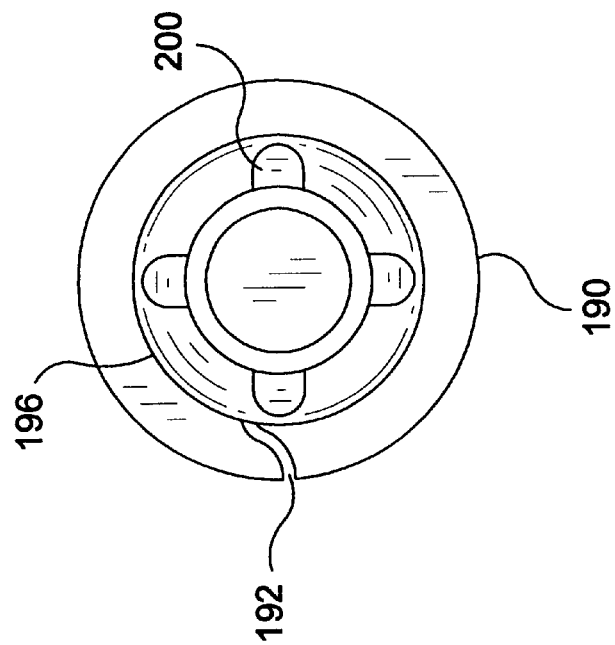
Figure 15A:
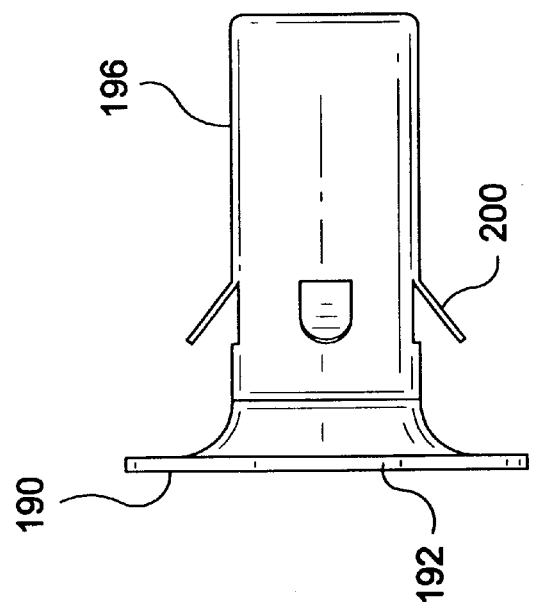

FIGS. 15a–e show a system for producing an end-to-side anastomosis that compresses the vessel wall between two fitting components. In this embodiment, the fitting 196 incorporates a flared distal region 190 having a slot 192 that defines two edges. The slotted distal end of the fitting is inserted through a puncture 194 of the vessel wall 39 by positioning the edge of the slotted fitting at the puncture site 194, angling the distal flared region 190 so the edge may be further advanced through the vessel wall, and rotating the fitting 196. Upon further rotation of the fitting 196, the entire flared region of the fitting is advanced into the interior of the vessel 38, as shown in FIG. 15d. Then a compression ring 198 is positioned over the fitting 196 and past the tabs 200 to compress the vessel wall 39 between the flared distal end 190 and the compression ring 198.

Figure 16C:
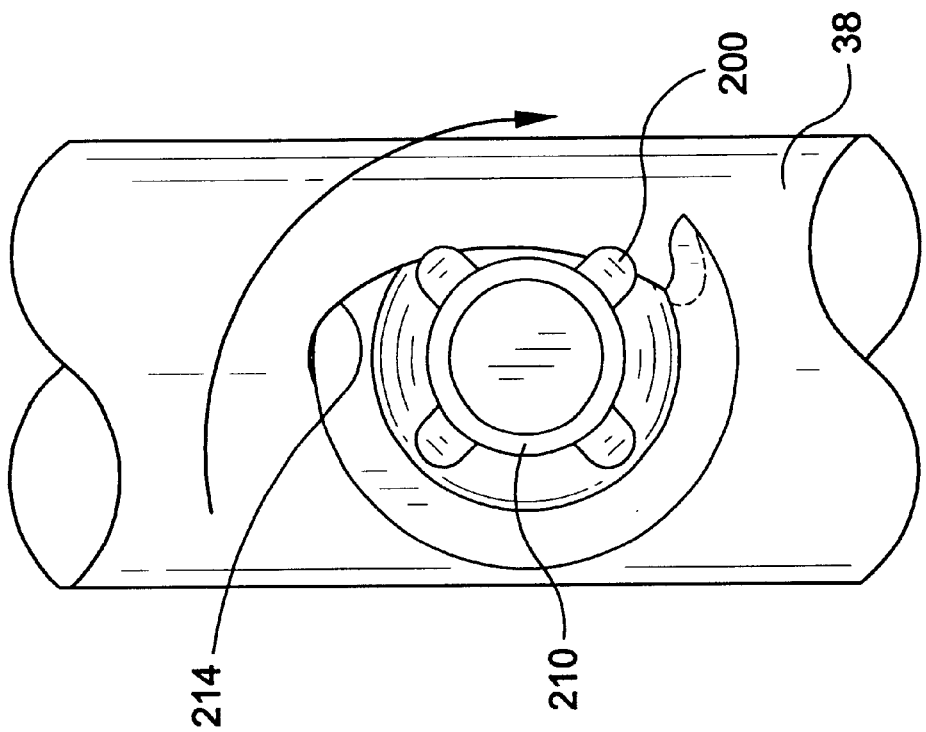
Figure 16B:
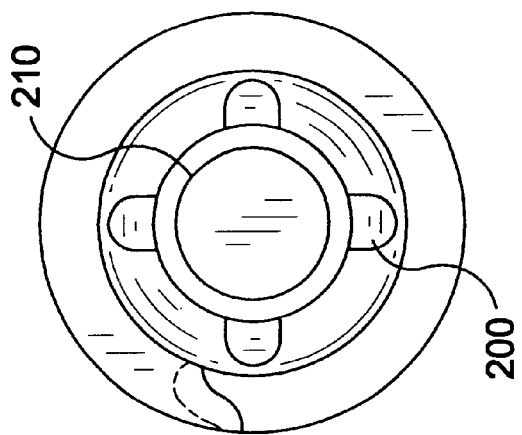

FIGS. 16a–c show fitting 210 including edge 212 at a flared end, and a slotted region to ensure a fluid tight fit after deployment and securement of the fitting 210 to a vessel with a compression ring (not shown). As shown in FIG. 16c, the lower edge is advanced through the puncture site 214, and the fitting 210 is rotated to advance the distal, flared end of the fitting into the vessel. Once in the vessel, a compression ring is advanced over the fitting 210 and is locked in place with the tabs 200 thereby securing the vessel wall between the distal, flared end of the fitting and the compression ring. The fitting 210 includes multiple rows of tabs 200 to accommodate various sized vessel walls. This feature is important when treating vascular diseases associated with thickening of the vessel wall.

Figure 16D:
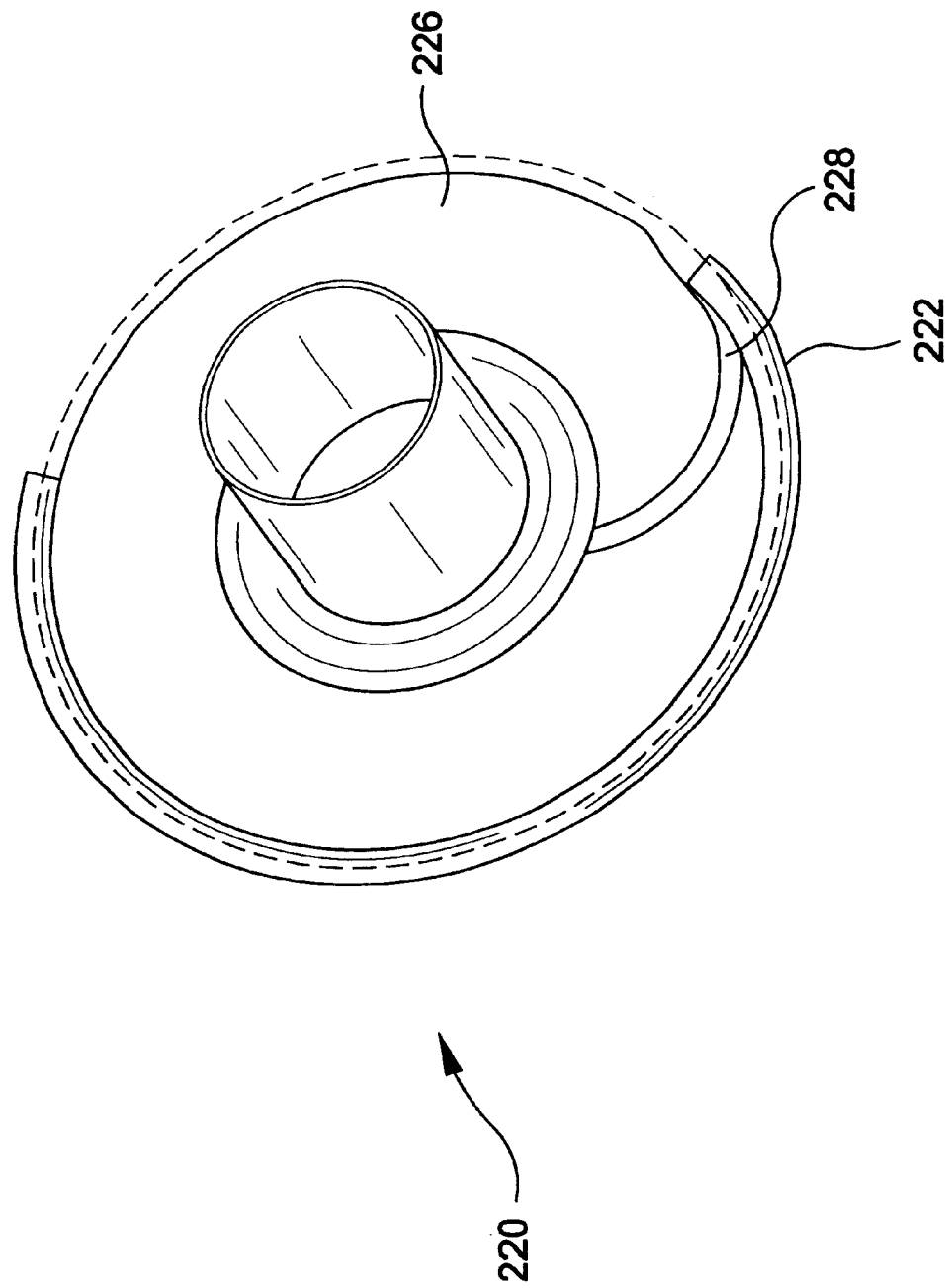
Figure 16E:
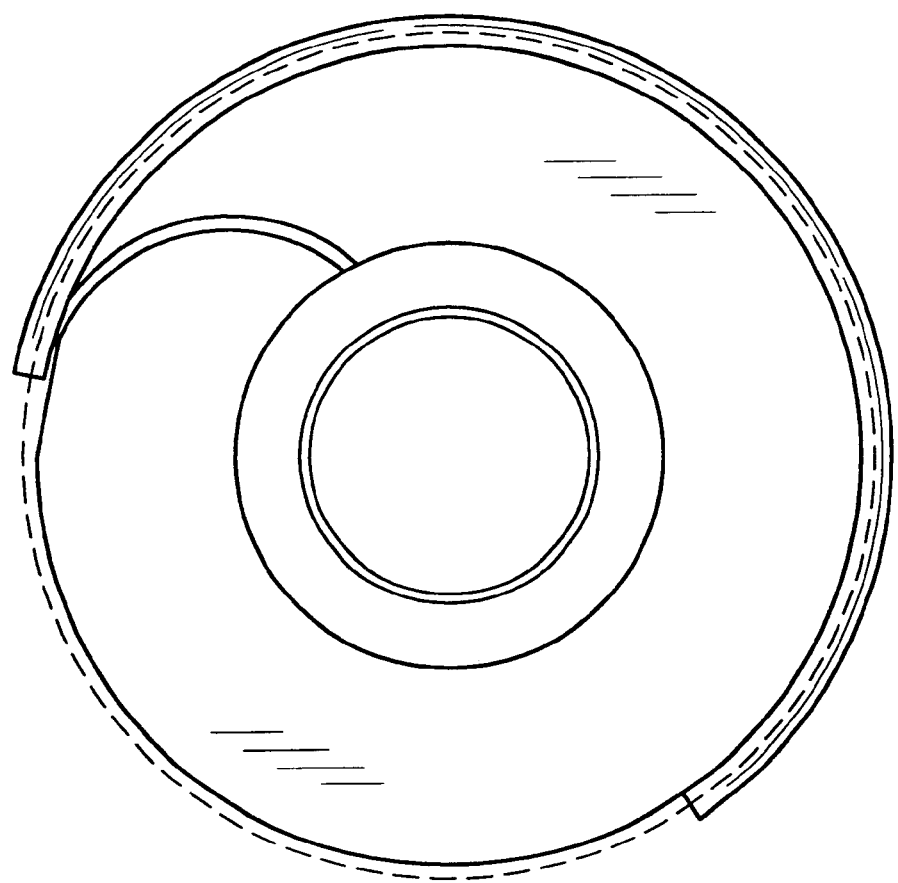
Figure 16E:
Figure 16F:
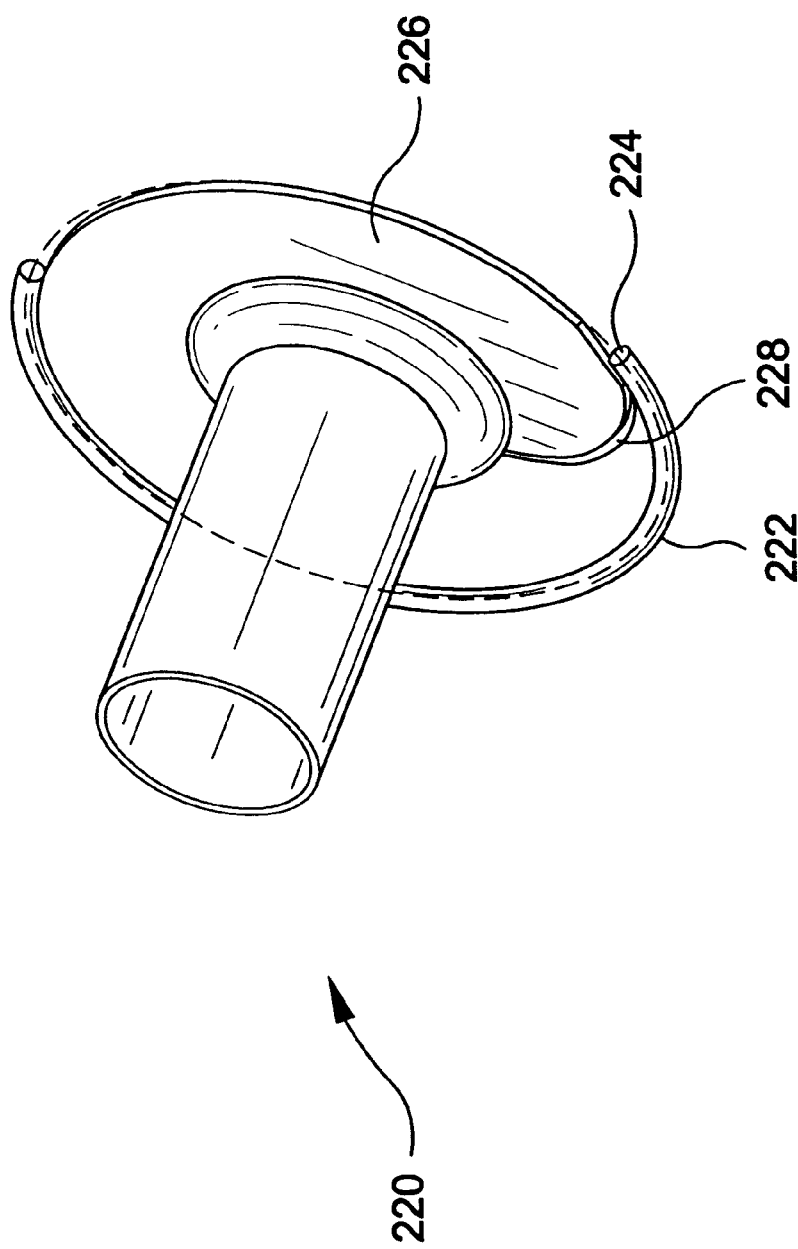
Figure 16G:
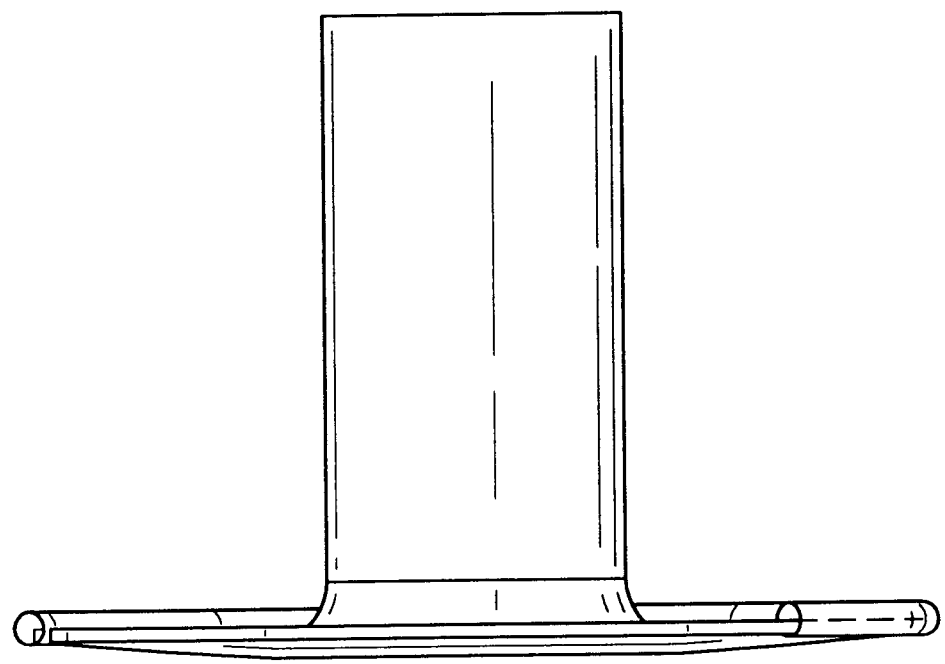

FIGS. 16d–e show fitting 220. In this configuration, a guidewire is inserted through the vessel wall and into the interior of the host vessel by puncturing the vessel wall with a needle and inserting the guidewire through the lumen of the needle. The needle is removed from around the guidewire after inserting the guidewire through the vessel wall. An insertion tubing 222 containing a central lumen 224 follows the periphery of the flared end 226 and is adapted to pass a guidewire. The guidewire is fed through the insertion tubing 222 to facilitate the screwing of the fitting past the vessel wall. The insertion tubing 222 extends approximately 40% to 80% around the flared end circumference. Alternatively, the insertion tubing 222 may be configured in sections extending around the circumference of the flared end such that a physician may determine how far around the flared end the guidewire must extend in order to rotate the flared end past the host vessel wall. A slot 228 through the distal flared end is adapted to accept the thickness of the vessel wall and enables the screwing of the fitting through the vessel wall. As the fitting 220 is advanced over the guidewire and rotated, the fitting 220 simultaneously expands the puncture through the vessel wall and inserts more of the distal flared end into the vessel interior. Once the flared end of the fitting 220 is inserted into the host vessel interior, the guidewire is removed and the fitting 220 is secured to the vessel wall using a compression ring and/or thermal securing. When using thermal securing, the distal flared end (at least the side facing the vessel wall) is made conductive and is attached to an energy source to heat the vessel and to thermally secure the fitting 220 to the vessel wall.

The fittings may be configured to incorporate electrodes to facilitate thermal securing of the fitting to the vessel wall. The electrodes may be fabricated from stainless steel, nickel titanium, platinum, platinum iridium, gold, titanium, tungsten, tantalum, or other conductive material and may also be fabricated to provide structural support to the bypass graft. Alternatively, the electrodes may be deposited (e.g. ion beam assisted deposition, sputter coating, solder, silk screen, pad printing, painting conductive epoxy, or other process) on the fittings and/or bypass graft such that the electrodes are thin and flexible and follow the contours of the fittings and/or bypass graft. The thermal securing properties may be the only attachment means required to provide a fluid tight bond between the fitting and the vessel wall. Alternatively, thermal securing may be augmented by attaching a compression ring as described above, applying adhesives to the bond, or suturing the fitting to the vessel wall. After securing the bypass graft to the fitting and advancing the fitting into the host vessel, the bypass graft and fitting combination may be attached to the host vessel wall.

Figure 6B:
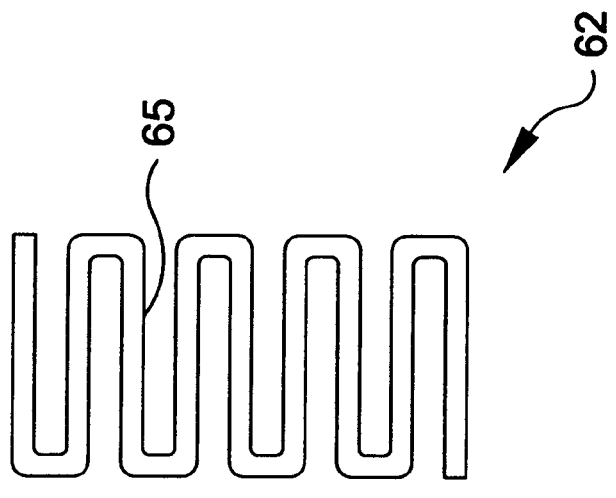
FIGS. 6a–d show expandable retaining ring embodiments capable of serving as electrodes for thermally securing the fitting to the host vessel wall.
Figure 6A:
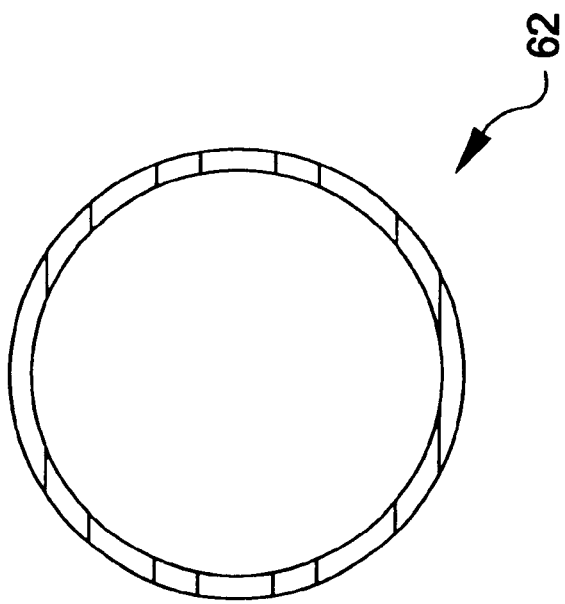
Figure 6D:
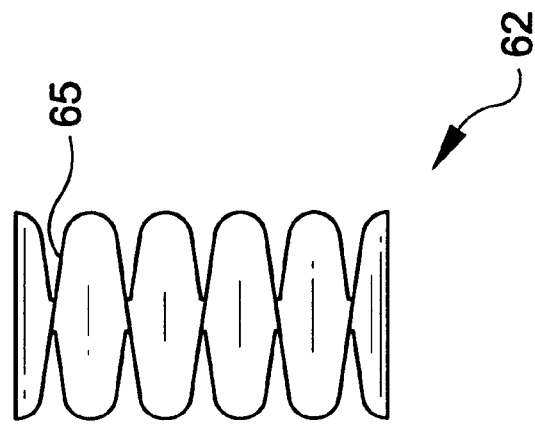
Figure 6C:
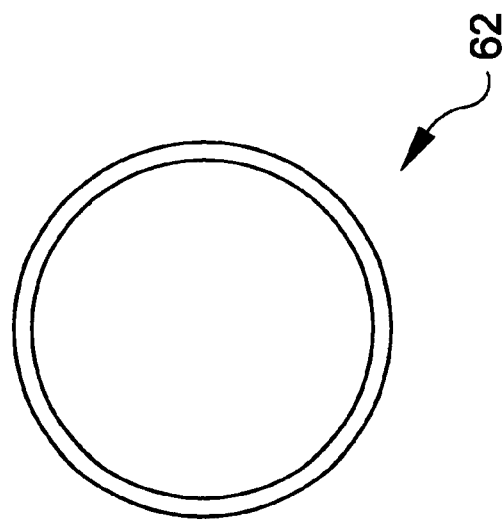
Figure 6F:
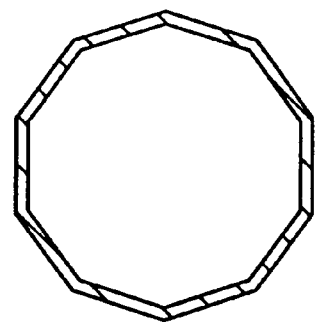
FIGS. 6e–f show an expandable retaining ring including petals to make an end-to-end fitting able to produce an end-to-side anastomosis.
Figure 6E:
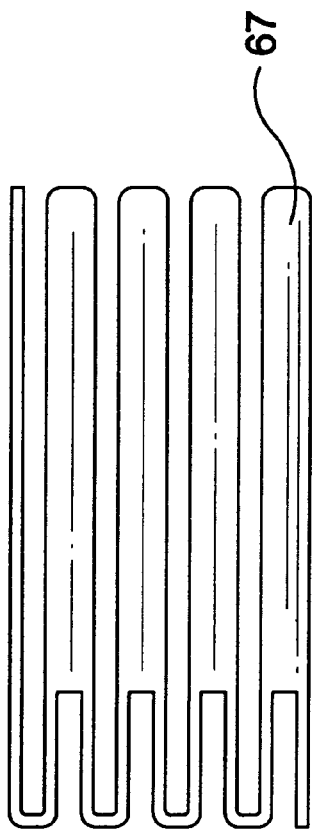
Figure 17A:
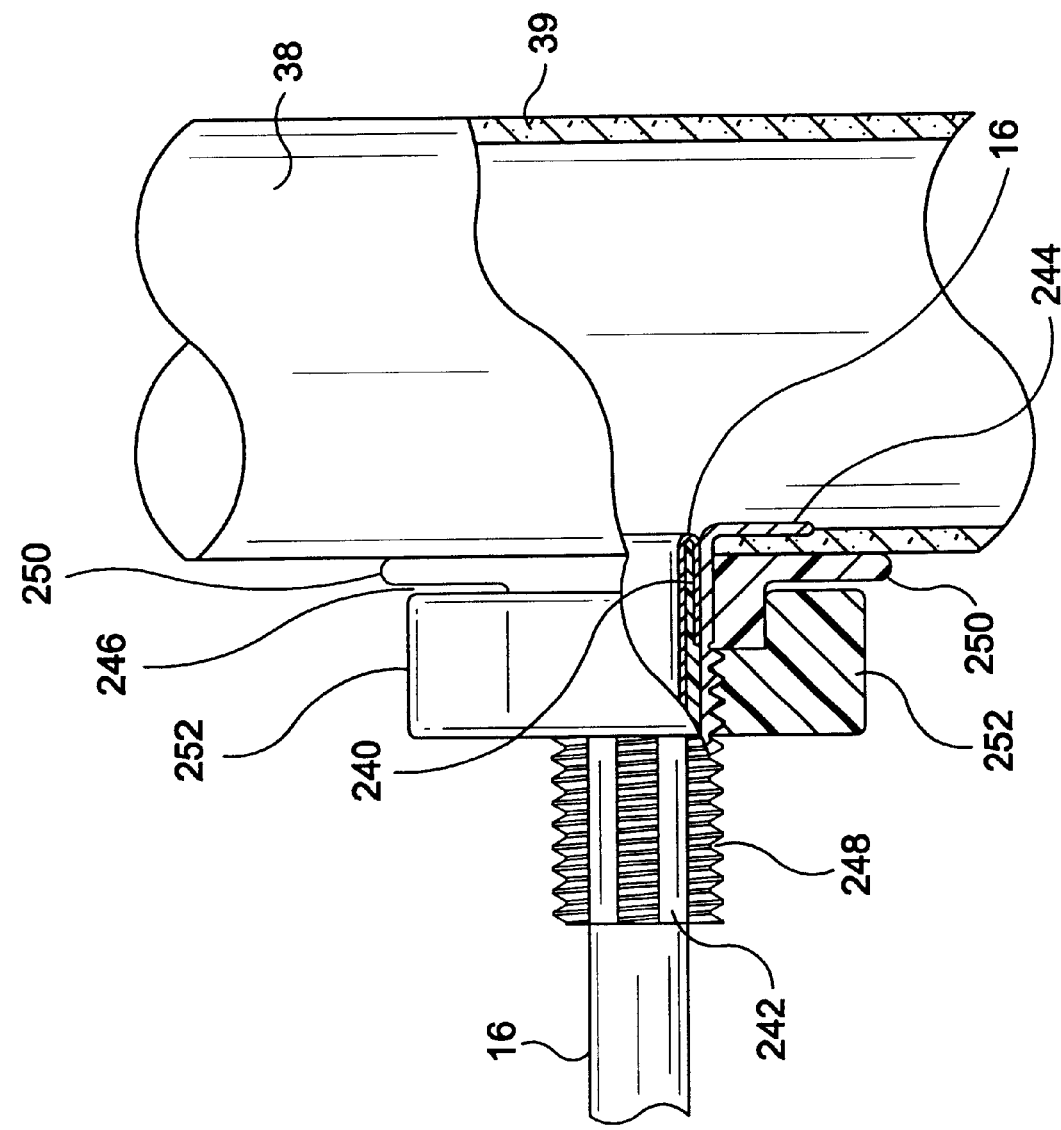
FIGS. 17a–b show an end-to-side fitting incorporating a retaining ring with petals.
Figure 17B:
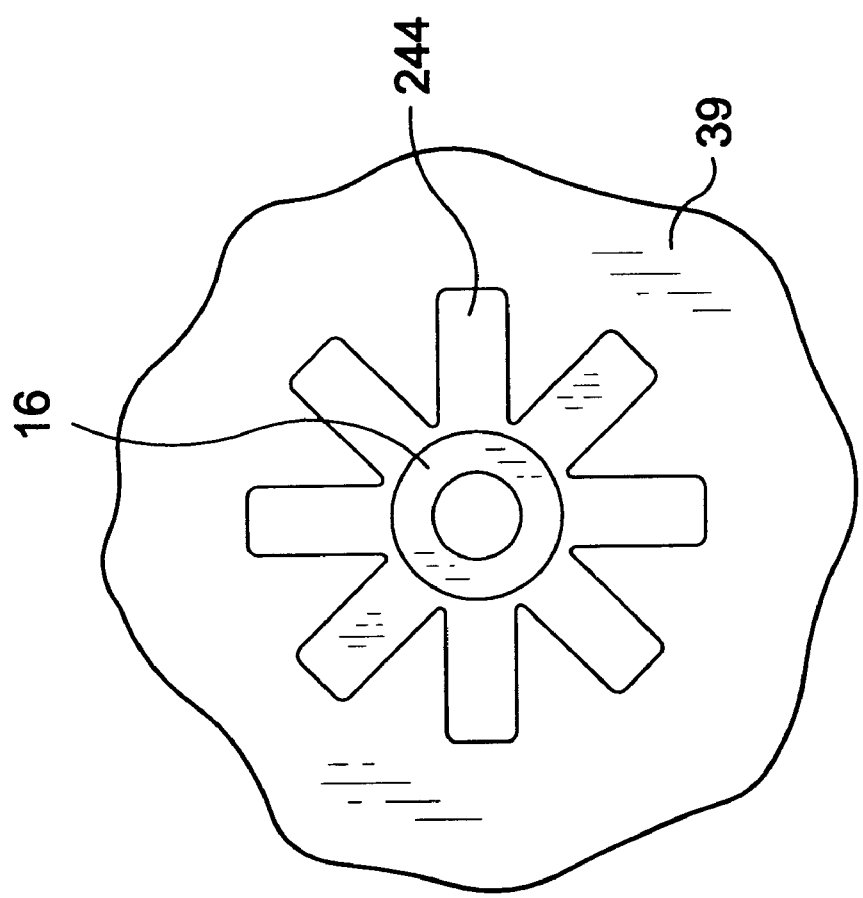

FIGS. 17a–b show a fitting 240 for performing an end-to-side anastomosis. A bypass graft 16 is everted over the distal end of the fitting 240. A retaining housing 242, similar to that shown in FIGS. 6e–f, is used to secure the bypass graft to the fitting. This retaining housing 242 permits radial expansion during placement over the bypass graft 16 and fitting and has a preshaped memory to compress around the bypass graft and fitting 240 to secure the bypass graft. This retaining housing 242 has petals 244 at its distal end, which compress into a low profile during delivery through a sheath and expand radially once deployed into the vessel 38. The number of petals 244 depends on the size of the bypass graft and the size of the host vessel. In this embodiment, eight petals are used. After advancing the fitting through a sheath, the fitting is advanced beyond the end of the sheath and is no longer constrained by the sheath, and expands towards its resting configuration. Then the bypass graft and fitting combination is gently retracted to engage the interior vessel wall at the petals 244. For mechanical securing, a compression ring 246 is advanced over the fitting thereby compressing the vessel wall 39 between the petals 244 of the retaining housing and the compression ring 246. The retaining housing may incorporate a threaded mechanism 248 to screw on the compression ring and secure the compression ring relative to the retaining housing. The threads are oriented only along the sections of the retaining housing configured to engage the compression ring. The slotted regions enabling the retaining housing to radially expand and collapse do not include threads. The compression ring 246 is alternatively locked in place using a screw mechanism, a ratchet mechanism, adhesives, sutures, or other attachment means to secure the compression ring in place. The compression ring 246 incorporates two components: 1) a distal, flexible o-ring or disk 250 designed to produce a fluid tight seal and prevent damaging the vessel wall by excess compression; and 2) a proximal, more rigid locking ring 252 used to maintain the position of the o-ring or disk relative to the vessel wall. The locking ring 252 is designed to match the threads incorporated in the retaining housing. Mechanical securing may be replaced or augmented with thermal securing.

Figure 18F:
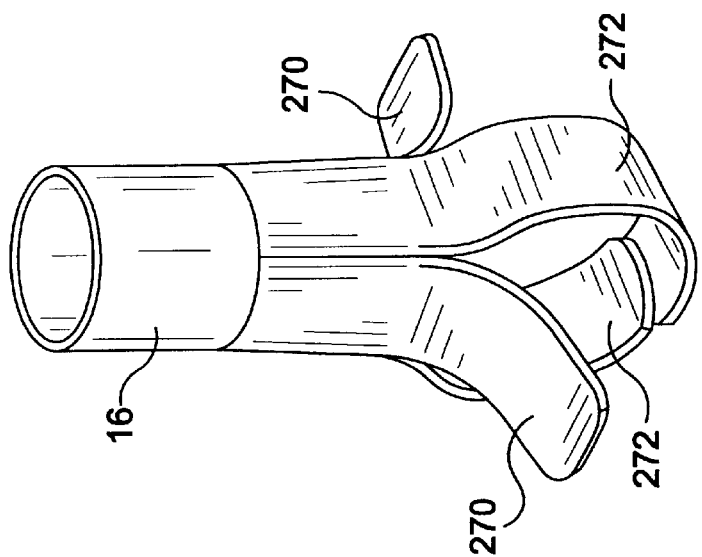
Figure 18E:
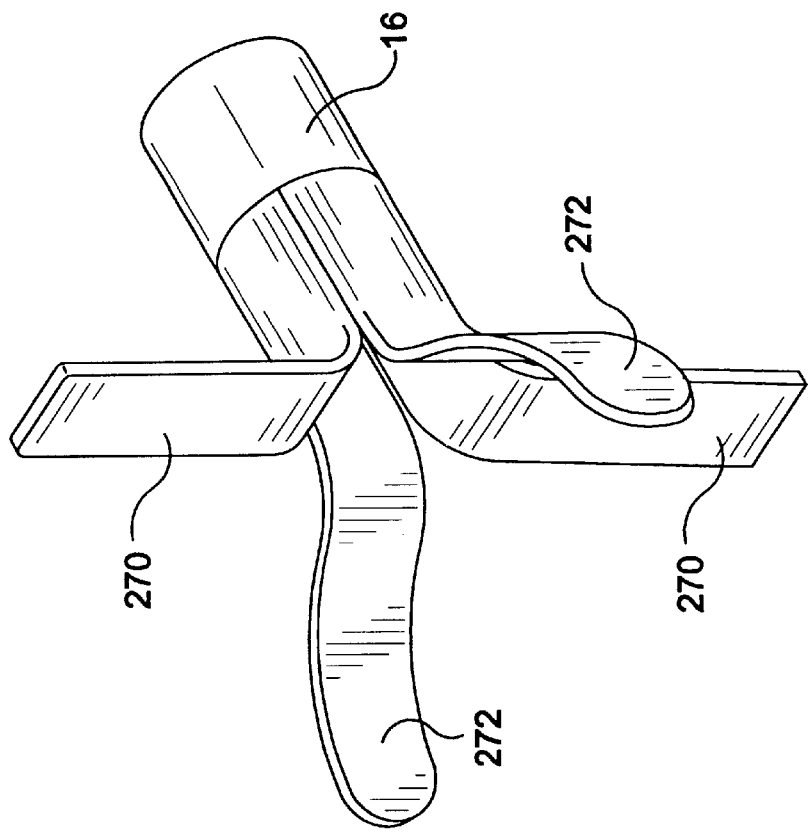
Figure 18G:
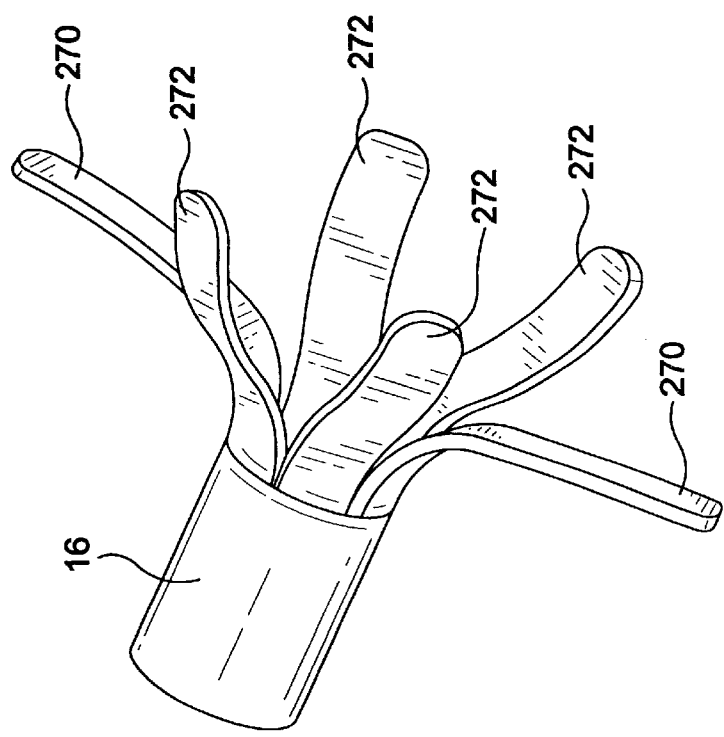

FIGS. 18a–g show a fitting 260 used to produce an end-to-side anastomosis, especially for medium to small diameter vessels (e.g. peripheral vessels and coronary vessels). As shown in FIG. 18a, four petals are collapsed into a low profile for insertion through a sheath 262 during deployment into the vessel. Once positioned, the sheath 262 is retracted enabling the petals to expand toward their resting shape. This fitting 260 includes two petals 264 designed to extend axially along the vessel and pre-formed to contact the host vessel wall. The fitting also includes two other petals 266 and 268 designed to extend radially around a portion of the vessel. The petals provide a structure to prevent the fitting from pulling out of the vessel, restrict rotation of the fitting relative to the graft, ensure the host vessel does not collapse or constrict at the anastomosis site, and provide a support to compress the vessel wall between fitting components. The petals 266 and 268 may be configured to return to a closed configuration in their resting state, as shown in FIG. 18f. Alternatively, the petals 266 and 268 may be configured to expand beyond the closed configuration in their resting state, as shown in FIG. 18e. This configuration helps the fitting petals exert radial force on the host vessel to better support the fitting within the host vessel and keep the host vessel open at the bond interface. These end-side fittings may alternatively include more than 4 petals. FIG. 18g shows an end-side fitting having two axially oriented petals, 270 and four radially oriented petals, 272. The petals, 270, 272 are configured to expand beyond the closed configuration in their resting state; alternatively, the petals may be configured to return to a closed configuration in their resting state. The fittings that produce end-to-side anastomoses may be configured to produce an angle (A) between the bypass graft 16 and the interior of the host vessel 38.

Figure 19A:
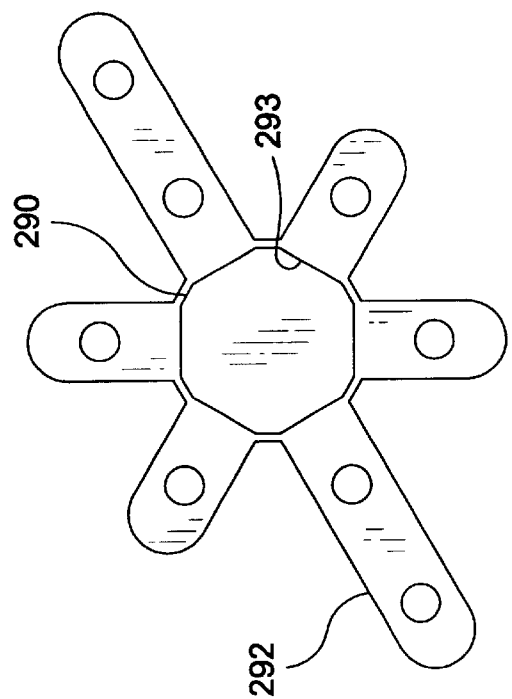
FIGS. 19a–f show a foldable end-to-side fitting.
Figure 19B:
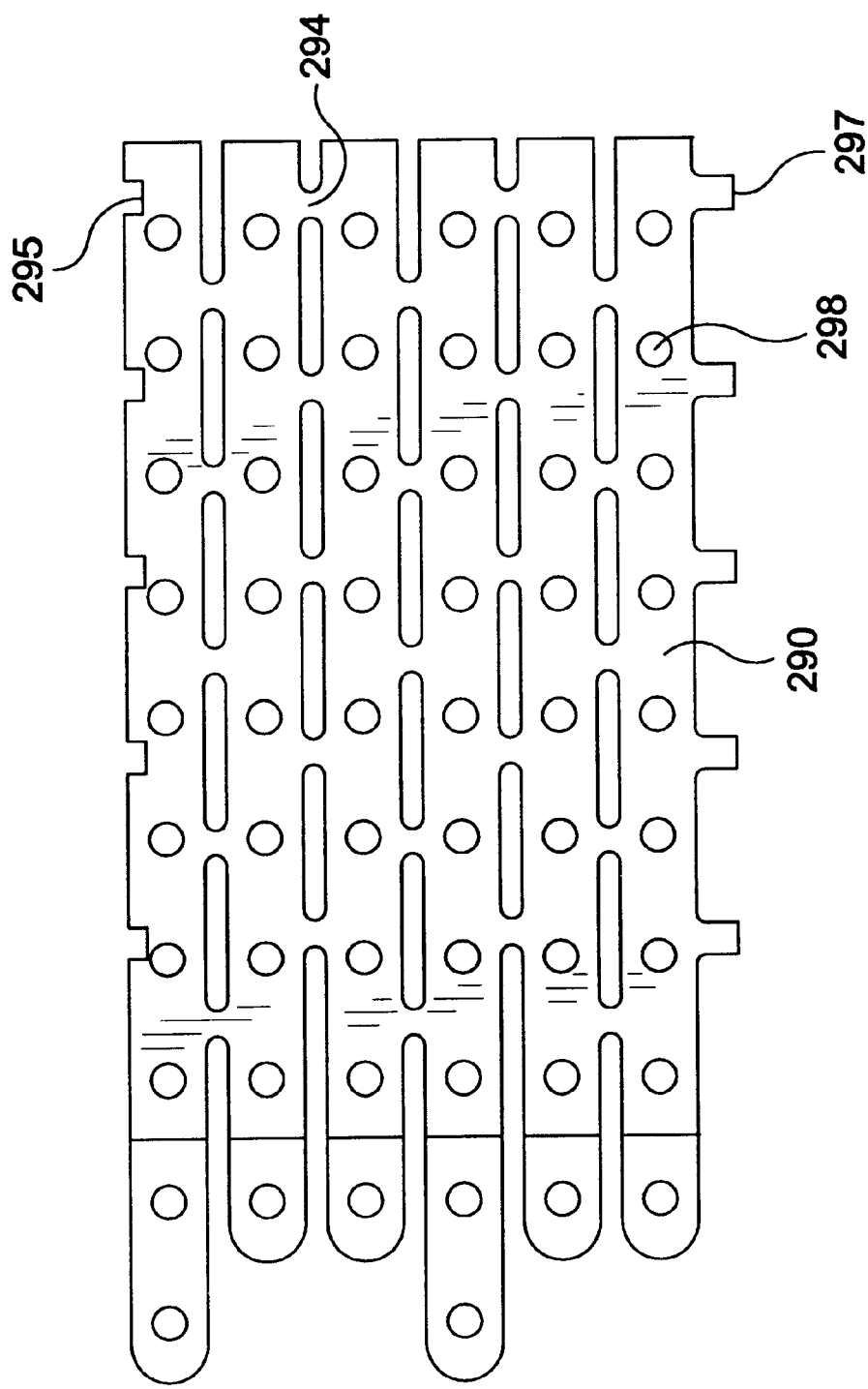
Figure 19D:
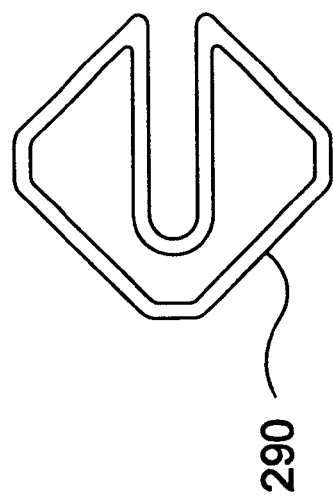
Figure 19C:
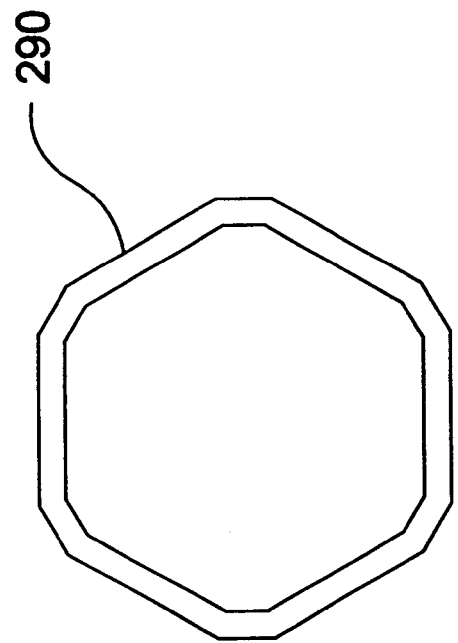

FIGS. 19a–f show an end-to-side fitting 290 that may be folded to insert through a sheath with a smaller diameter than the fitting. As shown in FIG. 19b, the foldable fitting 290 may be fabricated from a sheet of metal material that has been chemically etched, EDM, or laser drilled into the pattern shown. The opposite ends 295 and 297 of the fitting 290 match so they may be bonded together to form the expanded cross-section shown in FIG. 19c. Alternatively, the fitting may be fabricated from a tubular metal material using chemical etching, EDM, laser drilling, or other manufacturing process to form the desired pattern.

In FIG. 19a, the petals 292 are preshaped to expand radially outward once they have been deployed outside the introducing sheath. In this configuration the vessel wall can be compressed between the petals 292 and a compression ring. As shown in FIG. 19d, the fitting is designed to fold into a reduced diameter during deployment and expand toward its resting shape once positioned through the introducing sheath. The fitting includes links 294 that are fabricated by reducing the thickness or width of the fitting material and act as hinges for the fitting to fold into a low profile. The foldable fitting embodiment shown in FIGS. 19a–f is designed with 6 sides connected with links 293, 294 so two adjacent sides are able to fold inward thereby reducing the diameter for insertion through the delivery system. The foldable fitting may further be configured so two more adjacent sides at the opposite end of the initially folded sides are able to fold inward and further decrease the profile for insertion through the delivery system. The foldable fitting may alternatively have more than 6 sides and be configured so multiple adjacent sides fold inward to reduce the profile for introduction.

Figure 19E:
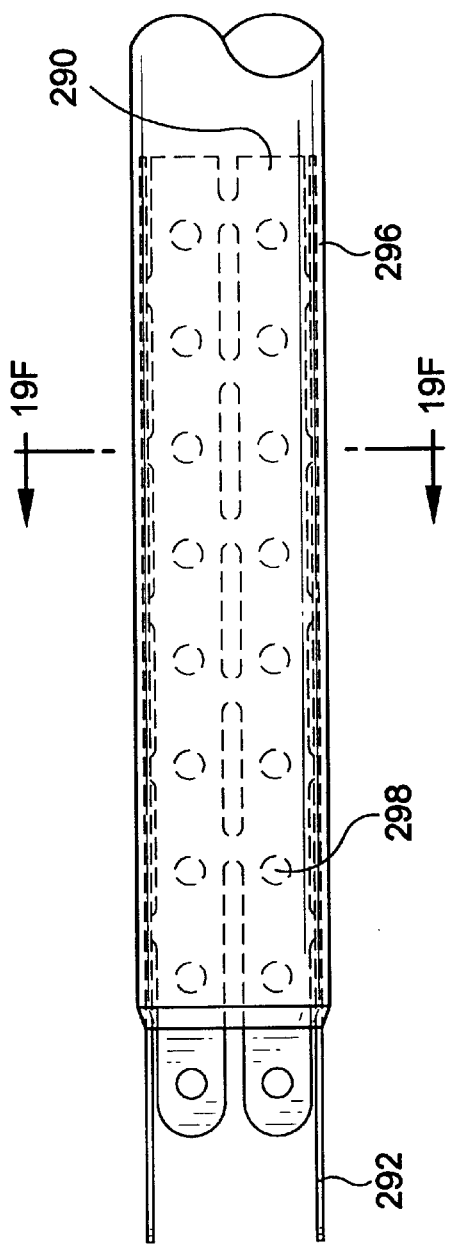
Figure 19F:
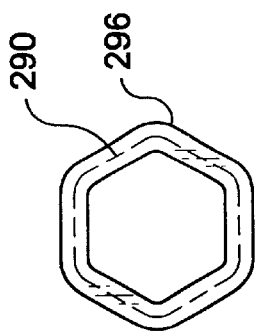

In FIGS. 19e–f, the foldable fitting incorporates a synthetic graft material 296 that is extruded, injection molded, or dipped onto the fitting 290. The manufacturing process causes the graft material to fill slots and holes 298 cut in the fitting 290. This produces a more reliable bond between the synthetic graft material and the expandable, foldable fitting. The covered fitting 290 will expand and fold as long as synthetic graft materials having a high percent elongation characteristic is chosen. The graft material may stretch along the folds incorporated in the fitting. A biological bypass graft (e.g. harvested vessel) may be sutured to the holes 298 incorporated in the fitting. The manufacturing processes and materials for fabricating this fitting 290 may also be used to fabricate end-to-end fittings by excluding the petals from the design. In addition, the foldable support structure may extend throughout the length of the bypass graft and be configured so that the sides rotate around the bypass graft at specific points to increase the axial flexibility but maintain the potential to fold into a reduced diameter.

Figure 20A:
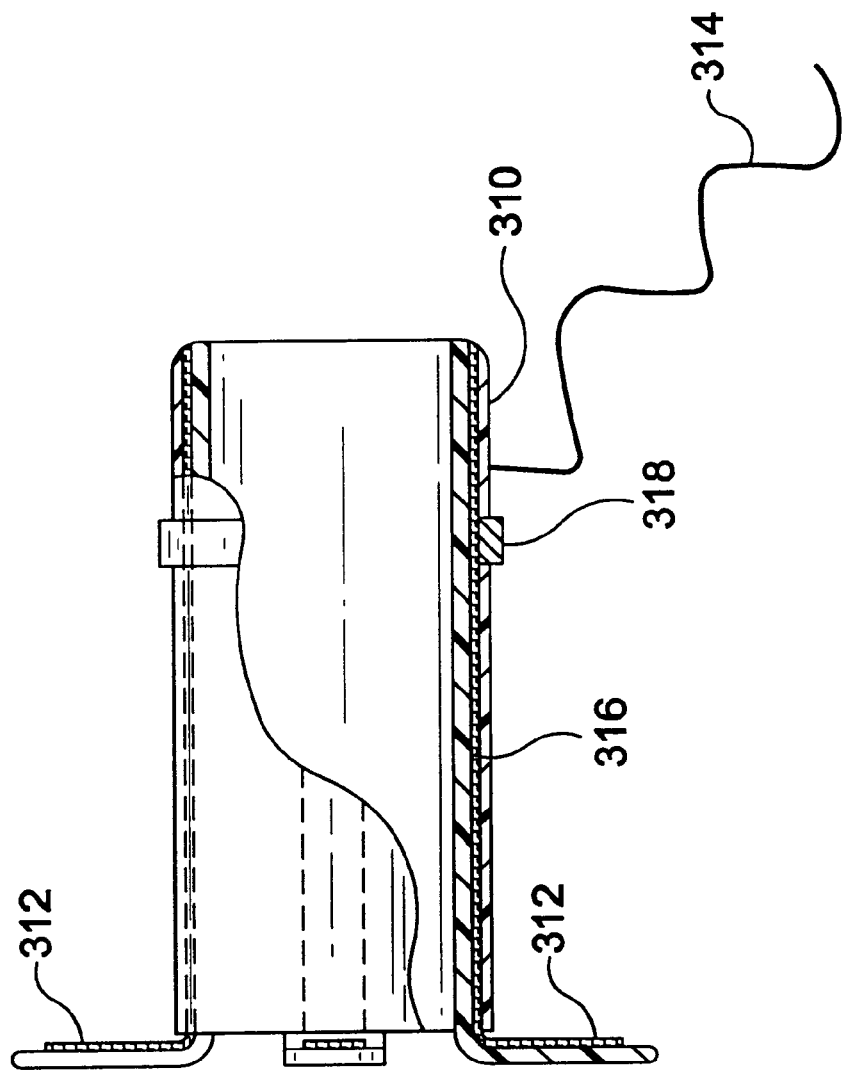
FIGS. 20a–b show an end-to-side fitting incorporating an electrode structure in the petals.
Figure 20B:
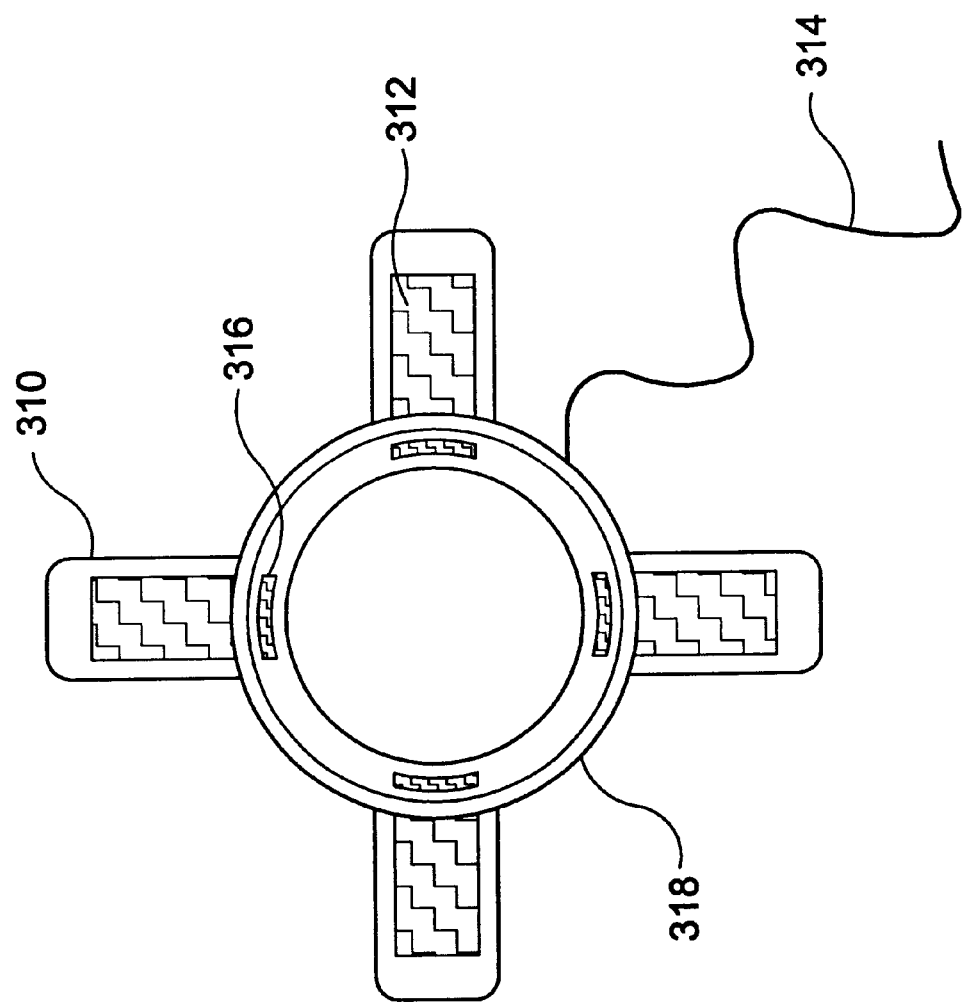

FIGS. 20a–b show an end-to-side fitting 310 having petals, and containing exposed electrodes 312 on the outside surface of the petals facing the vessel wall once deployed. A signal wire 314 is spot welded, crimped, attached using conductive adhesives, or soldered to provide an electrical connection between the electrodes 312 of the petals and a radiofrequency generator (not shown). The fitting 310 is fabricated by extruding, injection molding, or otherwise applying a nonconductive, conformal coating (e.g. elastomer) over an electrode structure 316 configured to include petals. In a second operation, the outside surfaces of the petals are removed exposing the electrodes 312. The petals are preshaped so the outside surfaces defining the electrodes contact the vessel wall, once deployed. As shown in FIG. 20a, a conduction ring 318 is placed into contact with the electrode structure 316 on the proximal end of the fitting and is bonded in place. A signal wire 314, used to transmit radiofrequency energy from a generator, is bonded to the conduction ring 318. As a result, radiofrequency energy transmitted to the conduction ring 318 will be routed to all electrodes positioned on the petals simultaneously. Alternatively, individual signal wires 314 may be attached to each petal electrode 312 and routed to a generator to independently energize each electrode.

The signal wire 314 may be fabricated from platinum, stainless steel, or a composite of materials (e.g. platinum and silver combined by a drawn filled tubing process). The composite signal wire uses the silver as the inner core to better transmit RF energy to the electrode and platinum to ensure biocompatibility. The signal wires may be fabricated with a circular, elliptical, rectangular (flat), or other geometry depending on the design of the electrode and space available in the delivery system. After thermal securing the bypass graft to the host vessel, the signal wire may be mechanically severed near the electrical connection using a pair of dikes. Alternatively, the signal wire 314 may incorporate a notch designed to separate when exposed to a desired amount of tension or torque, less than that required to dislodge the thermally secured bypass graft. Alternatively, the wire can be separated by transmitting pulses of radiofrequency or direct current energy through the signal wire capable of ionizing the signal wire and causing breakdown of the material. A notch may be incorporated in the signal wire to localize the breakdown point along the signal wire.

FIGS. 21a–b show an end-to-side fitting 330 incorporating an electrode structure 332 for thermally securing the fitting 330 to the vessel wall 39. The fitting 30 has a flared distal end with at least one electrode 332 exposed along the outside surface of the fitting. A signed wire 333 to transmit radio frequency energy from a generator may be attached to electrode 332. The at least one electrode 332 extends around the fitting 330 and has axial extensions adapted to orient the fitting along the vessel wall. The extensions provide an additional support structure to prevent rotation of the fitting relative to the vessel and reinforce the bond by using a mechanical securing mechanism such as a compression ring or other suitable means. The fitting 330 is manufactured from a polymer dipped, deposited, coated, or injection molded over a conductive structure such that only the distal outside surface of the conductive structure is exposed. The electrical connection will be established prior to dipping or injection molding of the fitting. The distal end of the flared electrode structure has a detent 334 to better secure the elastomer material to the electrode structure 332. The flared end of the fitting 330 must be flexible enough to be gathered into a low profile for introduction through a sheath and must have enough stiffness to contact the vessel wall and produce a fluid tight seal once secured in place.

Figure 21C:
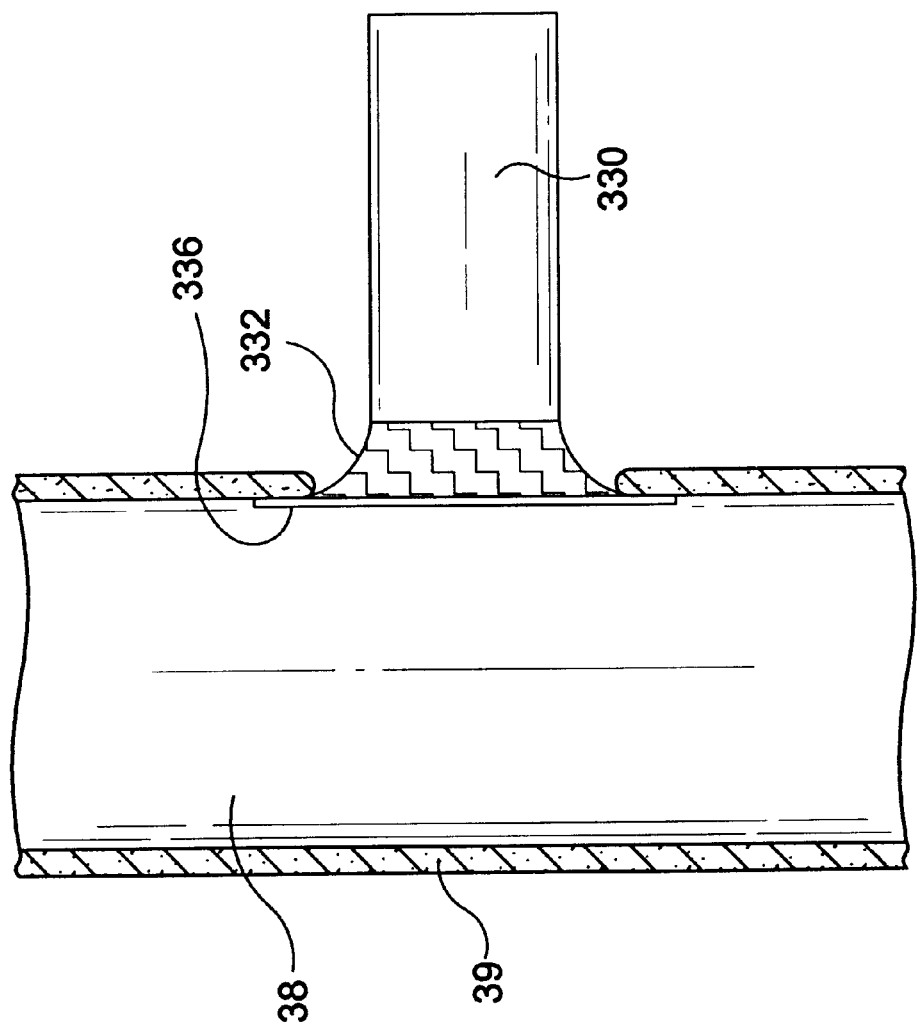
Figure 21D:
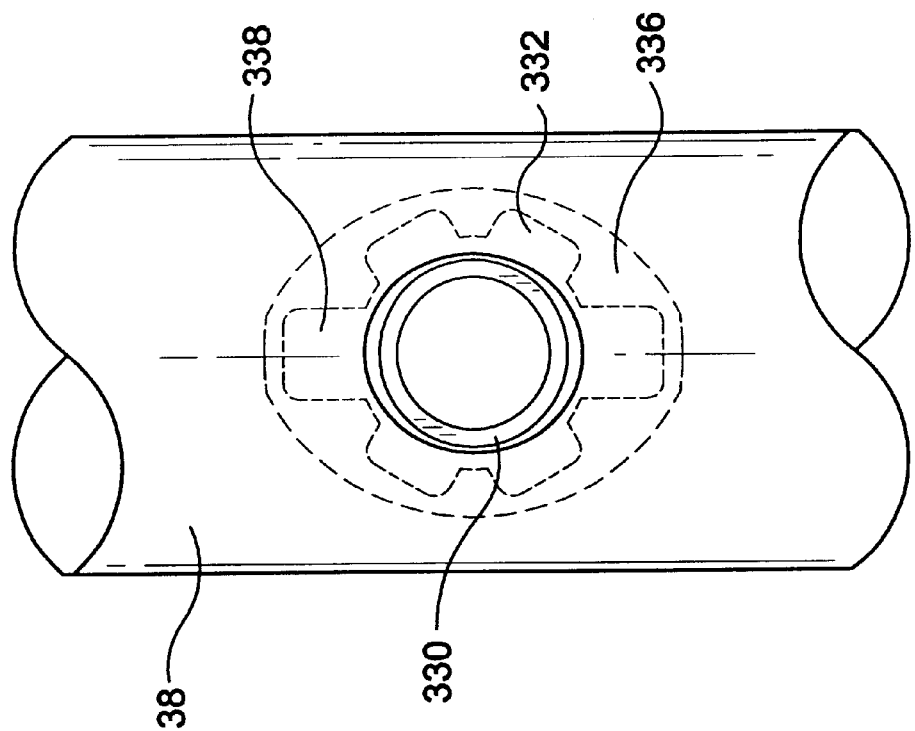

FIGS. 21c–d show another end-to-side fitting 330 incorporating an electrode 332. This embodiment includes an elastomer or other coating 336 around the distal, flared end of the electrode 332. The electrode 332 is configured with petals 338 that collapse during deployment of the fitting into the vessel. The elastomer coating 336 masks the blood flow, maintains the collapsibility of the fitting, and helps ensure a fluid tight bond between the fitting and the vessel wall. The electrode 332 is exposed on the outside surface of the distal, flared end of the fitting. The electrode 332 provides mechanical support to the fitting and enables thermal securing of the fitting 330 to the vessel wall 39.

Figure 22A:
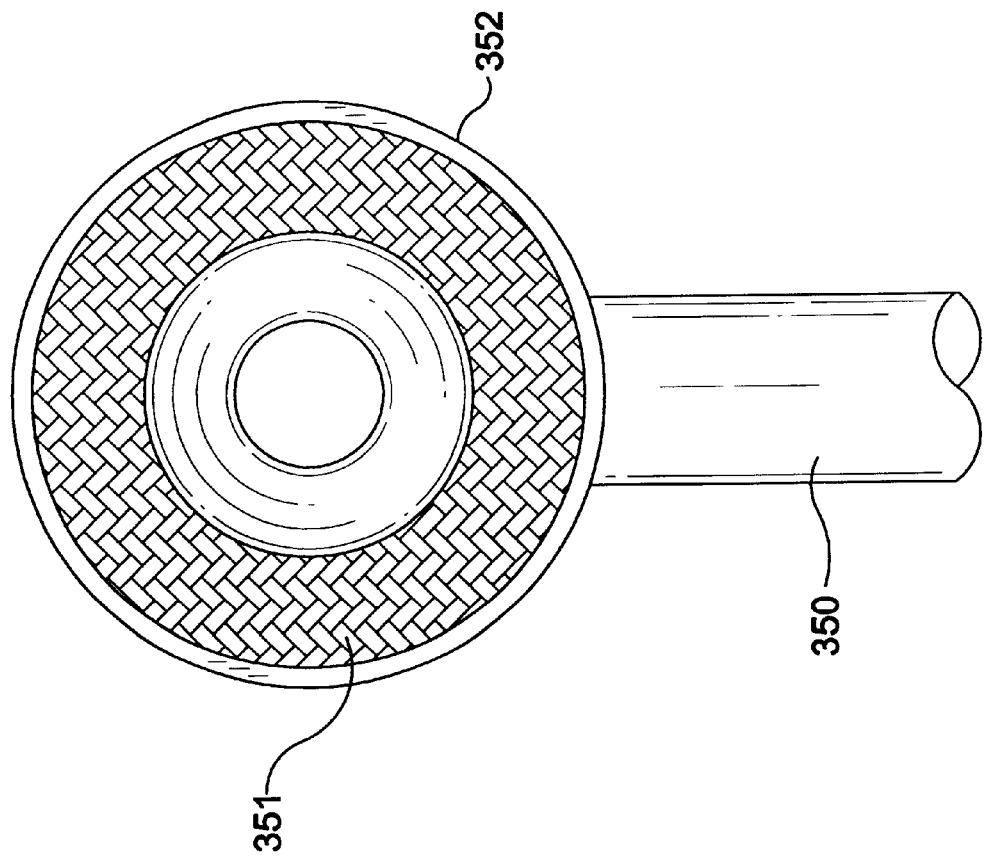
FIGS. 22a–b show an end-to-side fitting containing an electrode and able to fold into a low profile.
Figure 22B:
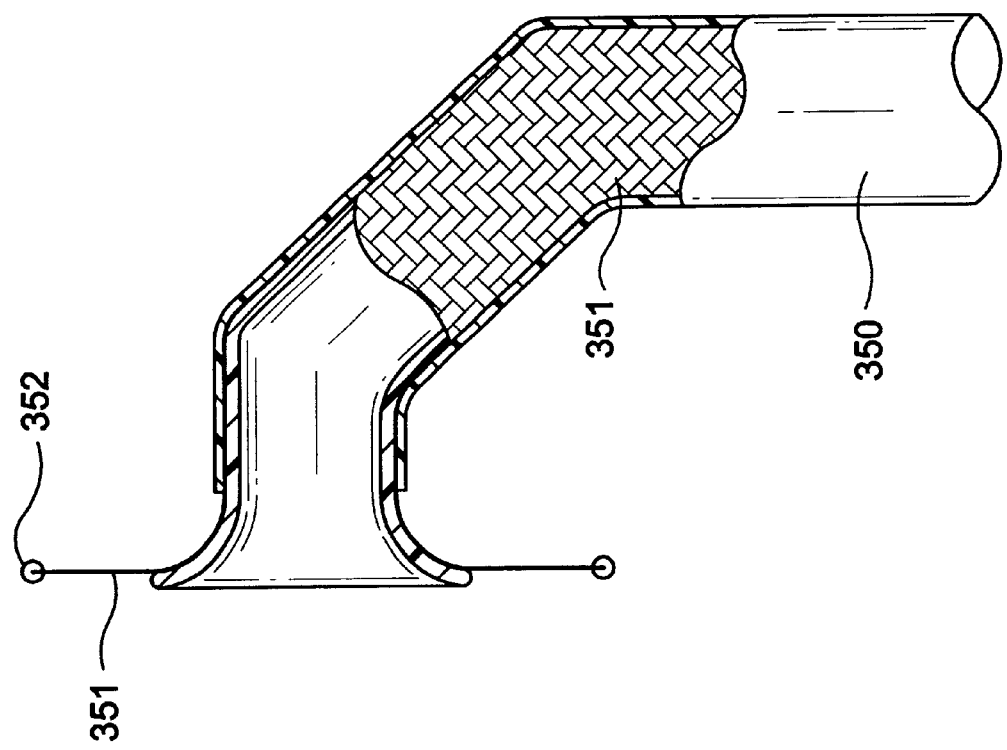

FIGS. 22a–b show an end-to-side fitting 350 incorporating an electrode structure 332 that enables the fitting to collapse into a low profile for insertion through an introducing sheath having a smaller diameter than the fitting 350. The distal flared end of the electrode structure 351 compresses forward and the body of the fitting folds into a low profile for insertion through a sheath. Once deployed outside the sheath, the fitting 350 returns to its expanded, resting configuration. The flared, distal end contacts the interior surface of the vessel wall and provides a structure to compress the vessel wall using a compression ring. The electrode structure is fabricated from a conductive material (preferably but not limited to memory elastic materials) braided over a thermoplastic, thermoset plastic, silicone, or other material and is formed into a preshaped configuration having a flared end. The braided electrode structure may alternatively be composed of a memory elastic material such as nickel titanium for providing structural support intertwined with a good conductor such as platinum. Additionally, the braided material may be deposited with a conductive material to increase conduction. Since the electrode structure 351 is braided, the distal end of the electrode structure 351 is coated with an elastomer or other material 352 to prevent unraveling of the braided material. This electrode structure 351 may also used to thermally secure the fitting to the vessel wall once radiofrequency energy is transmitted to the electrode structure from a generator.

Figure 23:
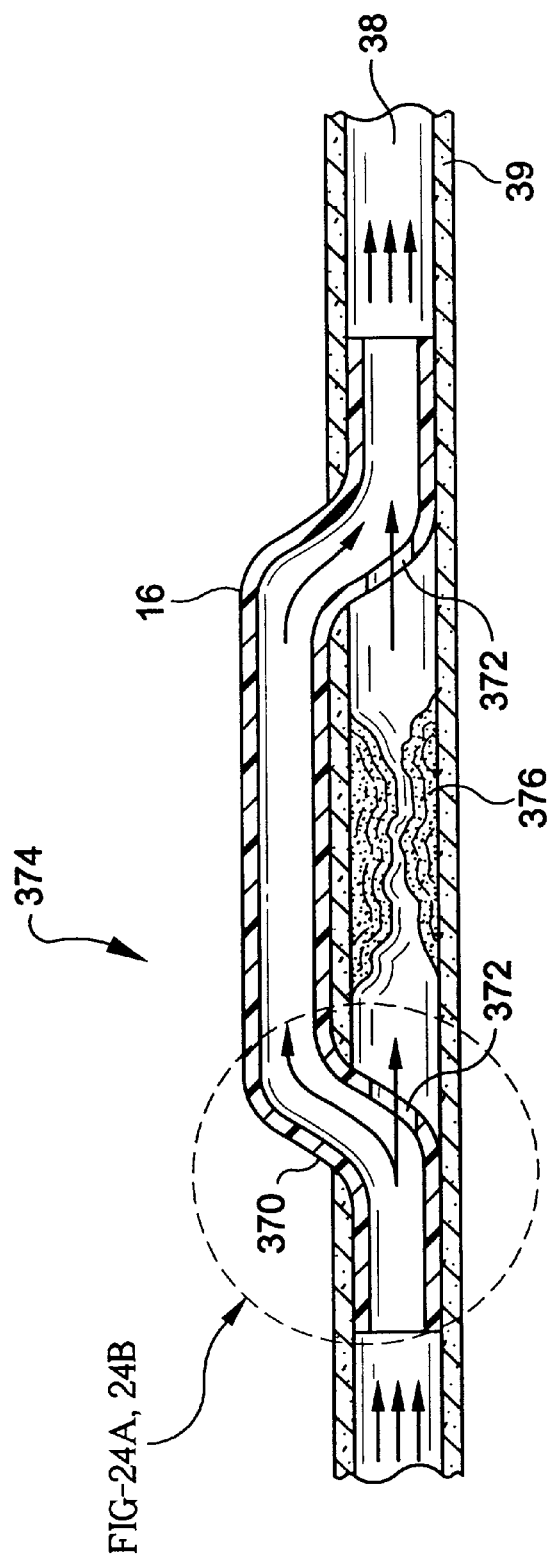
FIG. 23 shows a bypass graft and fitting combination attached to a host vessel and designed to preserve flow proximal to the anastomosis site.

FIG. 23 shows an end-to-end fitting 370 that permits retrograde blood flow through the anastomosis site. The fitting 370 has holes 372 through the angled sections of the fittings to preserve fluid flow through the vessel distal and/or proximal, depending on the location of the fitting within the host vessel. The bypass graft and fitting combination 374, after deployed within and attached to the vessel maintains blood flow through the stenosis as well as establishes a passage around the lesion 376. The fitting 370 maintains blood flow to branching vessels proximal to the anastomosis site.

Figure 24B:
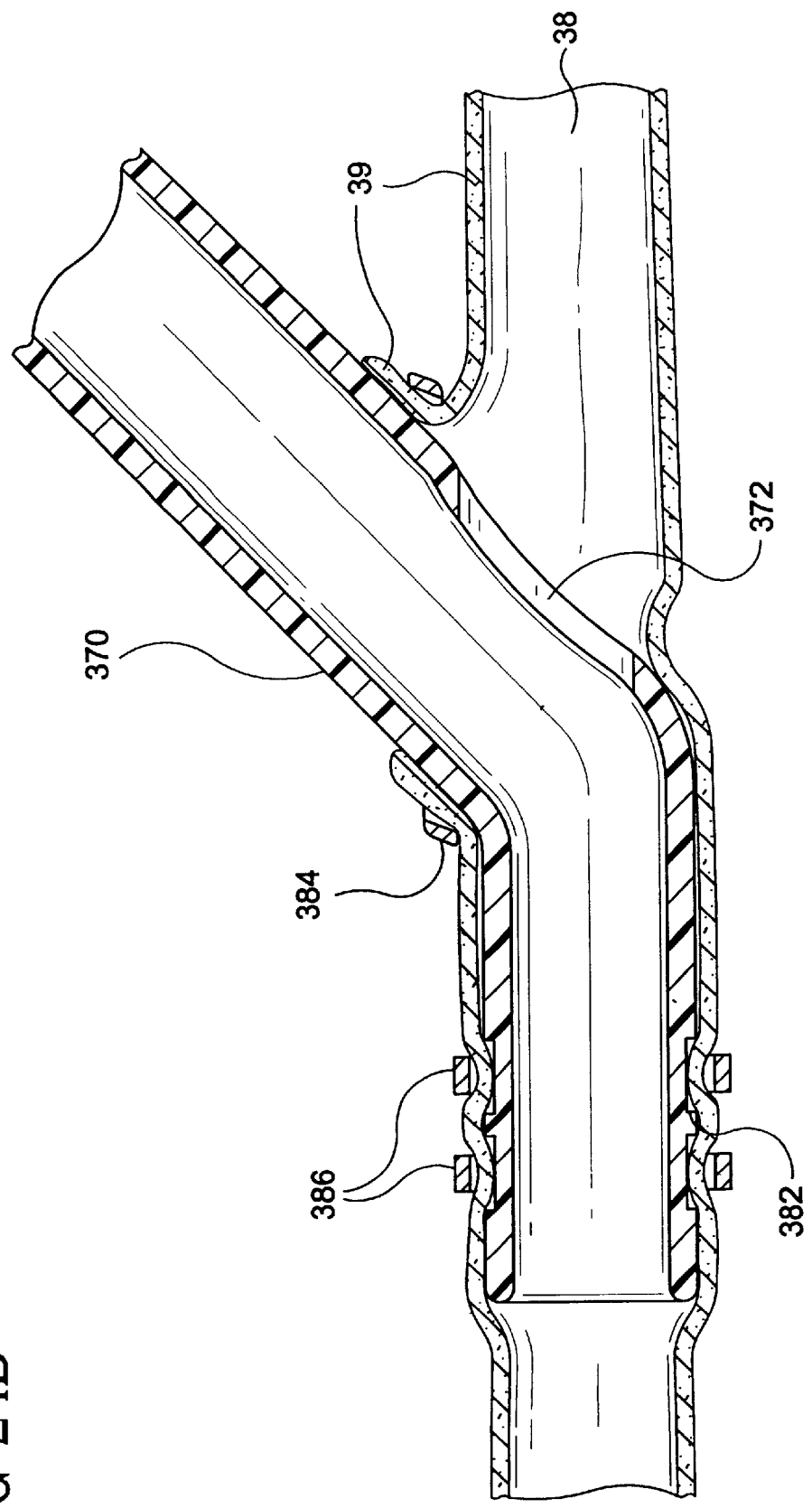
Figure 24C:
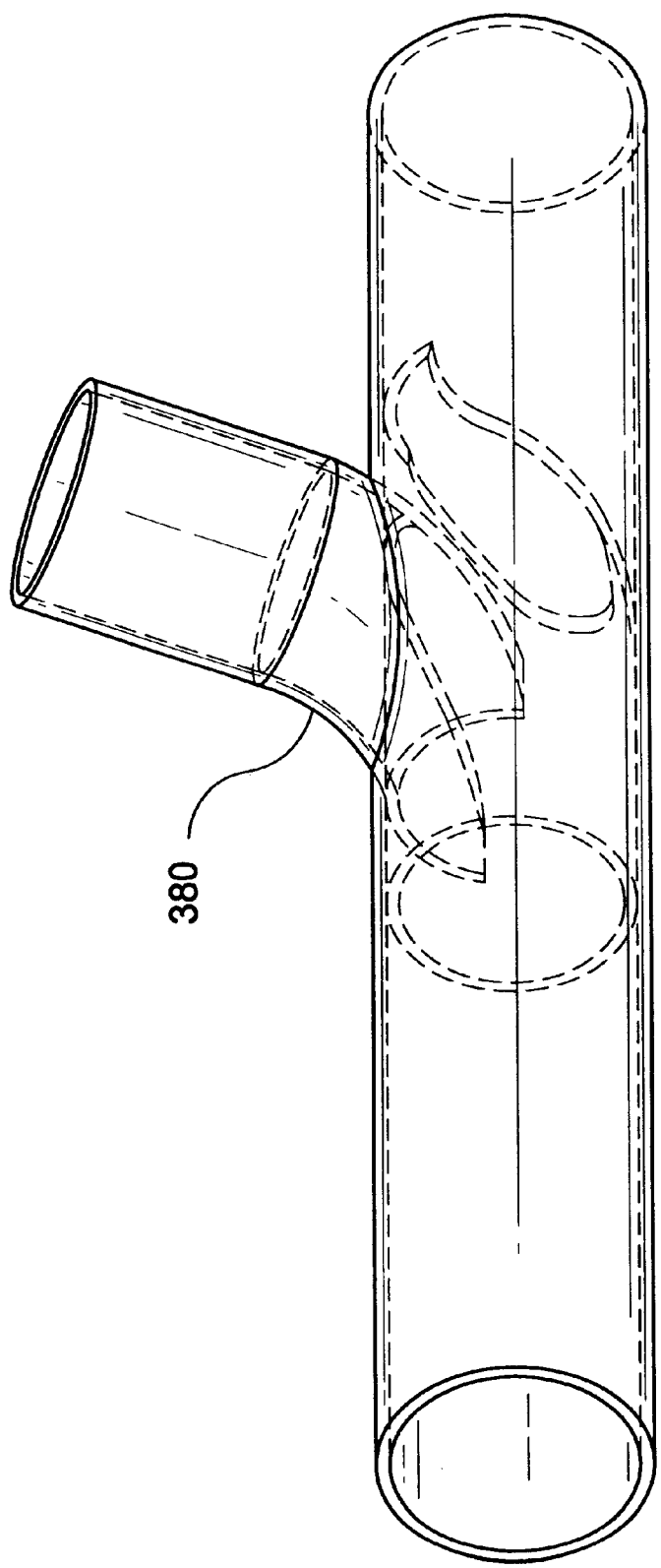
FIGS. 24c–h show alternative bypass graft and fittings designed to maintain retrograde blood flow.
Figure 24D:
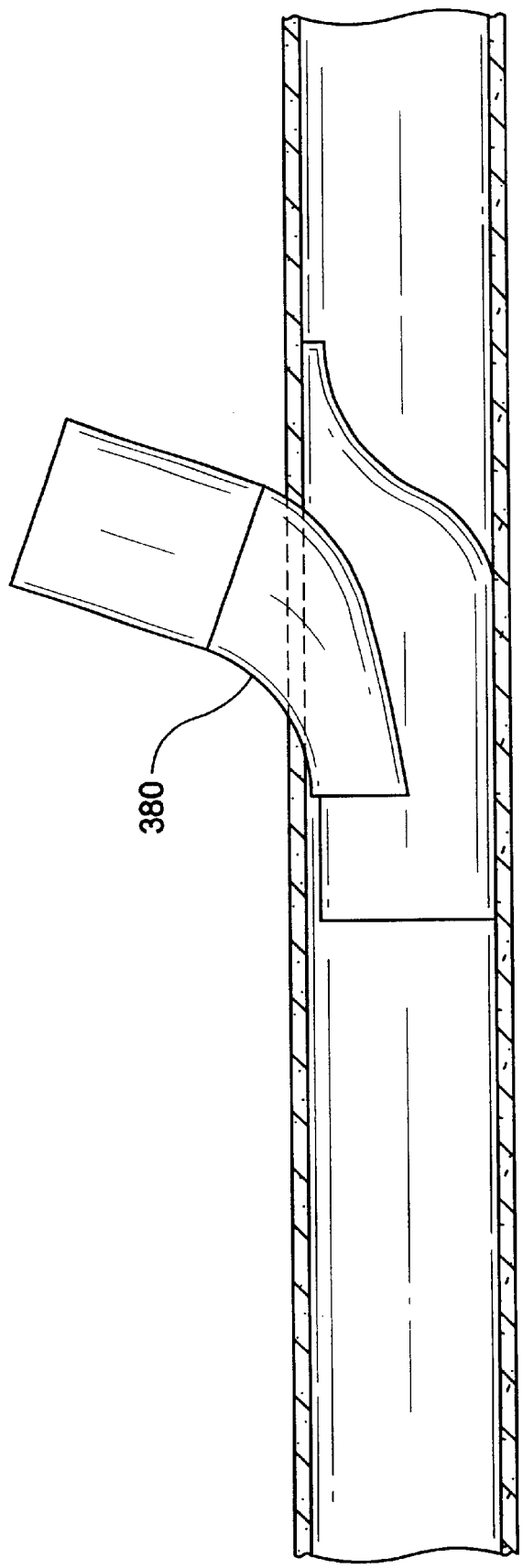

FIGS. 24a–b show fitting 370 attached to the vessel at two locations. The fitting 370 is placed within the vessel and contacts the interior surface of the vessel along a substantial length. FIG. 24b shows that the fitting 370 may incorporate barbs 382 to prevent axial dislodgment of the fitting from the host vessel 38. The barbs may also provide a support to secure a retaining ring or suture to mechanically secure the fitting to the host vessel. A second attachment is located at the insertion site through the vessel wall 39. A compression ring or retaining ring may be used to compress the vessel wall 39 around the fitting 370 and prevent fluid from leaking at the insertion site. Electrodes may additionally or alternatively be positioned around the fitting at the insertion site 384 and/or at the distal end 386 of the fitting to thermally secure the fitting to the vessel wall and provide a fluid tight bond. The electrodes may be fabricated from stainless steel, nickel titanium, platinum, platinum iridium, gold, titanium, tungsten, tantalum, or other material and may also be fabricated to provide structural support to the bypass graft. Alternatively, the electrodes may be deposited (e.g. ion beam assisted deposition, sputter coating, pad printing, silk screening, soldering, or painting conductive epoxy) on the fittings and/or bypass graft such that the electrodes are flexible and follow the contours of the fittings and/or bypass graft. Fitting 370 is particularly useful for medium size diameter vessels (>3 mm) where synthetic bypass grafts are used to supplement the blood flow through the vessel or shunt the blood flow to other vessels or organs.

Figure 24E:
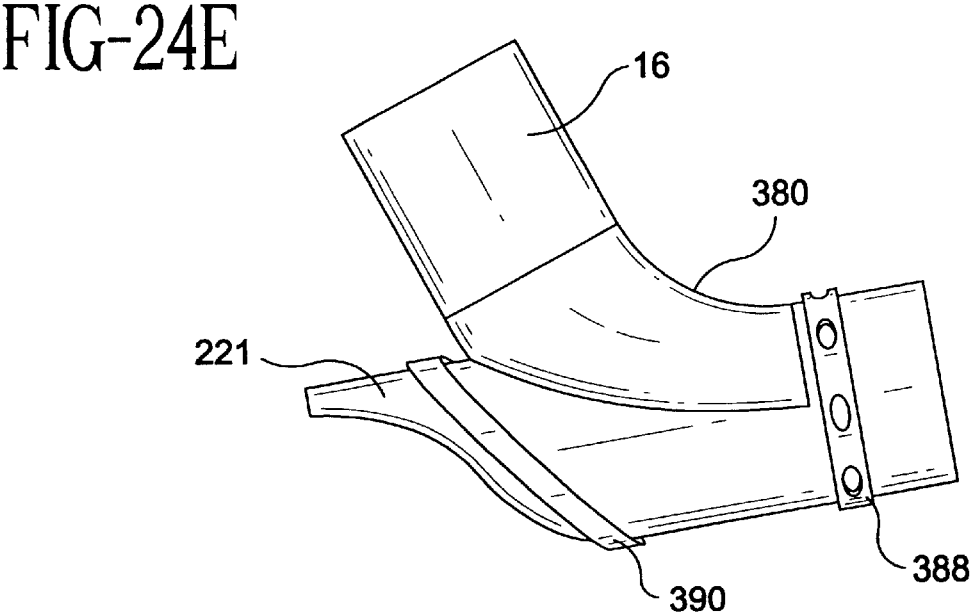
Figure 24F:
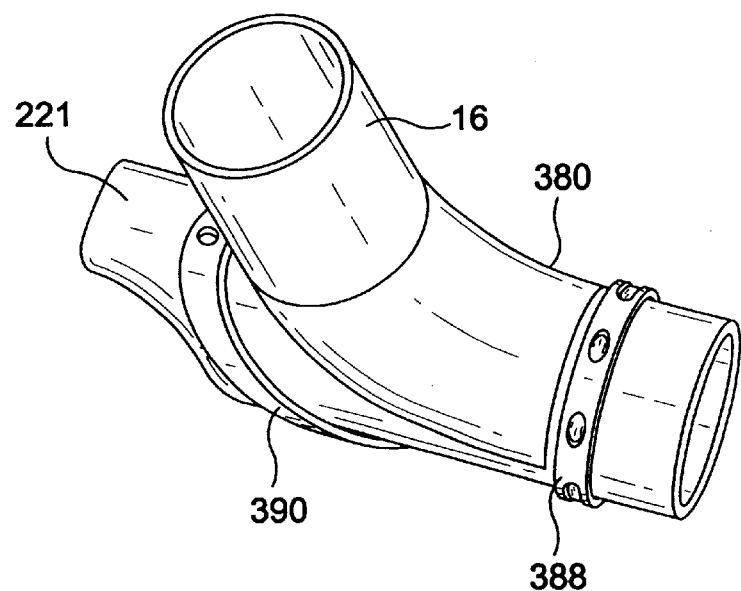

FIGS. 24c–h show additional end-end fitting embodiments that permit retrograde blood flow. The fitting 380 incorporate a modification to provide a short proximal extension that contacts the vessel wall along the insertion site at the host vessel. This provides a structure to attach a compression ring and produce a fluid tight bond at the insertion site. A locking mechanism is incorporated in the fitting design to enable securing a compression ring to the fitting. Alternatively, FIGS. 24e–f show the fitting 380 may incorporate two electrodes, 388, 390 around the distal end and proximal extension of the fitting. An electrode may also be located around the leg of the fitting located at the insertion site. The electrodes, 388, 390 may incorporate holes to improve thermal securing of the electrodes to the host vessel wall.

Figure 24G:
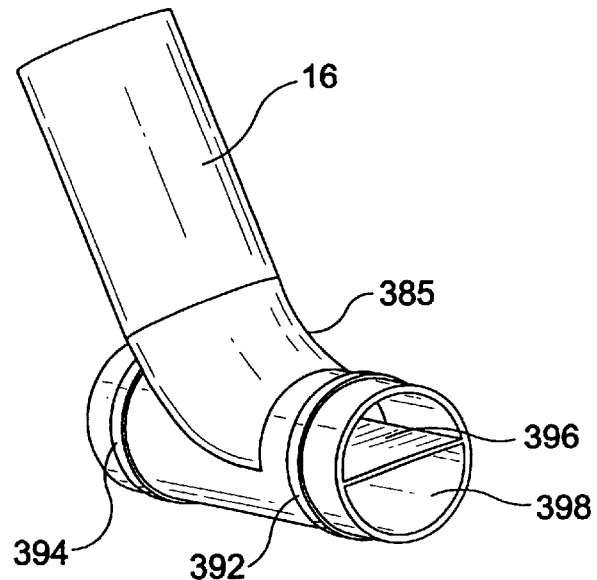
Figure 24H:
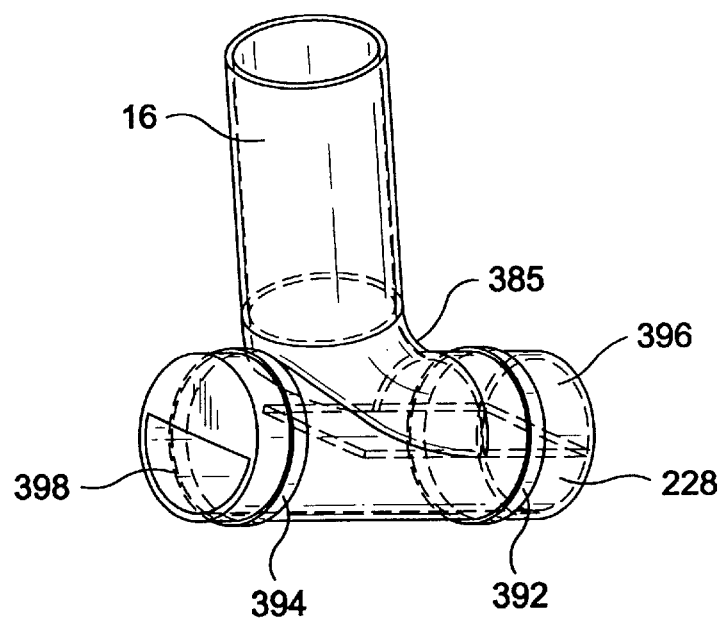

FIGS. 24g–h show another end-end fitting 385 that permits retrograde perfusion and incorporates electrodes, 392, 394 around the distal end and proximal extension of the fitting. This fitting also includes two separate lumens. Lumen 396 connects blood flow from the bypass graft 16 to the host vessel. Lumen 398 connects blood flow between regions of the host vessel proximal to the anastomosis site and distal to the anastomosis site.

The inventions described in this patent application describe embodiments that permit thermally securing bypass grafts to host vessels. The inventions require localized transmission of energy to precisely heat the interior surface of the host vessel and a support structure to maintain contact between the bypass graft and host vessel during and after the thermal securing process. The coagulation of tissue and shrinkage of blood vessels results from the application of heat and thermally secures the bypass grafts to the host vessel.

Figure 25:
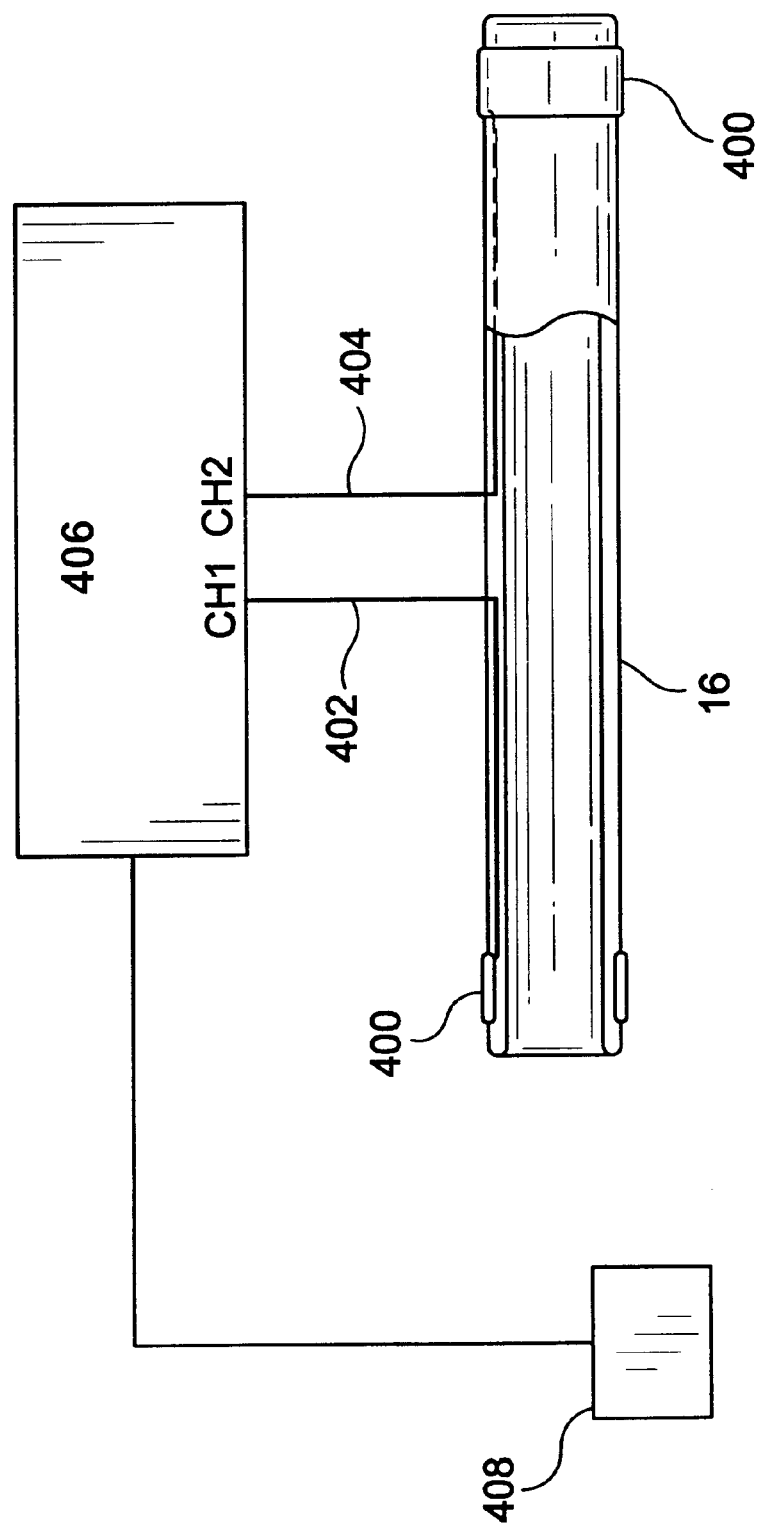
FIG. 25 is a schematic of the system used to thermally secure the ends of the bypass graft to the vessel wall.

A thermal securing mechanisms as shown in FIGS. 14 and 25 is used to increase the strength of the mechanical bond, and ensure a fluid tight seal between the bypass graft and host vessel. Alternatively, thermal securing may be solely used to bond the bypass graft fitting to the vessel wall. This feature may be adapted to all fittings. Thermal securing is accomplished by coagulating tissue to the electrodes and is enhanced by an induced shrinking of the heated tissue region producing an interference fit between the vessel and the fitting. These physiologic responses to heating produce a secure bond between the electrode and the vessel wall and prevent leaking around the fitting.

Coagulating tissue to thermally bond a patch of porous material to the external surface of tissue has been described by Fusion Medical Technologies, Inc. (U.S. Pat. Nos. 5,156, 613; 5,669,934; 5,690,675; 5,749,895; and 5,824,015). A sheet of collagen or similar porous material is placed over tissue and sufficient energy from a radiofrequency inert gas source is delivered over the patch to form coagulum at the tissue surface. The coagulum fills the pores of the external patch and cools to form a bond thereby producing hemostasis between the tissue and the external patch. The Fusion Medical product is suited for applications such as lung resections or reattaching transected vessels where direct exposure to the wound enables positioning the patch over the external surface of the tissue, and an energy source may be used to grossly apply heat over the exterior of the patch.

Published studies evaluating the response of vessels (arteries and veins) to heat have focused on the ability to permanently occlude vessels. Veins have been shown to shrink to a fraction of their baseline diameter, up to and including complete occlusion, at temperatures greater than 70° C. for 16 seconds; the contraction of arteries was significantly less than that of veins but arteries still contracted to approximately one half of their baseline diameter when exposed to 90° C. for 16 seconds (Gorisch et al. Heat-induced contraction of blood vessels. *Lasers in Surgery and Medicine.* 2:1–13, 1982; Cragg et al. Endovascular diathermic vessel occlusion. *Radiology.* 144:303–308, 1982). Gorisch et al also observed vessel relaxation within 8 minutes after exposure to heat with arteries relaxing more than veins; even so, the final diameters of the contracted arteries and veins were less than their baseline diameters. Embodiments of the invention mitigate the concern for vessel relaxation by incorporating a spring mechanism in the fitting and/or electrode design to accommodate subtle changes in vessel diameter.

Gorisch et al explained the observed vessel shrinkage response "as a radial compression of the vessel lumen due to a thermal shrinkage of circumferentially arranged collagen fiber bundles". These collagen fibrils were observed to denature, thus shrink, in response to heat causing the collagen fibrils to lose the cross-striation patterns and swell into an amorphous mass. These published observations into the contraction of vessels due to heat provide evidence to the proposed invention of using radiofrequency energy to produce an interference fit between a contracted vessel and a fitting.

FIG. 25 shows a schematic for a bypass graft 16 incorporating two end-to-end fittings and containing electrodes 400 designed to thermally secure the bypass graft to the vessel wall. The electrodes 400 are secured to the fitting and are bonded to signal wires, 402 and 404, which are routed to a generator 406. Radiofrequency or d.c. current is transmitted to the electrodes unipolar to an indifferent ground patch electrode 408 placed on the patient, or bipolar between the electrodes.

Various features of the electrodes enhance the heating response and improve the bonding between the electrodes and the vessel wall. Contact between the electrode and the vessel is important to ensure an adequate bond when thermally securing the electrode to the vessel wall. The outer diameter of the electrode in its expanded configuration should exceed the inner diameter of the host vessel to ensure adequate contact between the vessel wall and the fitting.

Figure 26A:
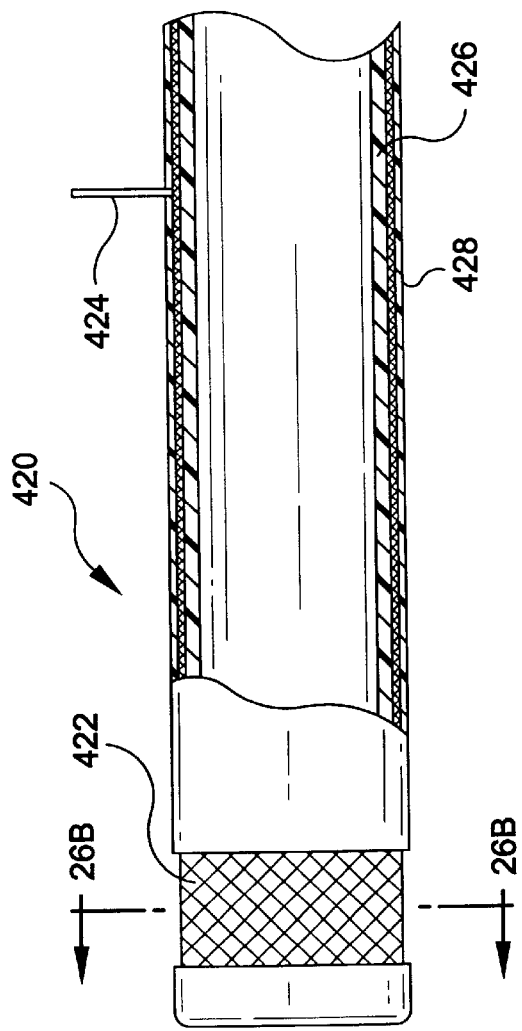
FIGS. 26a–b show an end-to-end bypass graft having an electrode incorporated in the bypass graft.
Figure 26B:
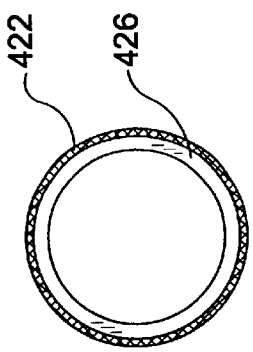

FIGS. 26a–b show an end-to-end fitting 420 incorporating an electrode 422 into the design. The fitting 420 collapses into a low profile during insertion into the vessel and expand towards its resting state upon deployment into the vessel. Such an expandable, collapsible fitting helps ensure contact between the electrode 422 and the vessel wall despite any mismatching of the bypass graft size to that of the host vessel. The fitting may be extruded in a multi-layer configuration. The electrode may be braided into a mesh over an initial polymer layer 426. A second polymer 428 may be extruded, injection molded, or dipped over the braided first layer. To expose the electrode 422, a section of the outer layer is removed. Alternatively, the section of exposed electrode may be masked when extruding, injection molding, or dipping the outer layer. A signal wire 424 is bonded to the braided mesh, before or after fabricating the outer layer, to produce an electrical connection that is routed to a generator.

FIGS. 27a–b show a bypass graft incorporating an electrode 430 that is designed to collapse into a low profile during deployment and expand to contact the vessel wall once inserted into the vessel. The electrode 430 is attached to a signal wire 432, which is used to connect the electrode to a generator 434. This electrode 430 is fabricated from a mesh of memory elastic material formed over an initial polymer layer 436, and preshaped to have an expanded region as shown. The regions proximal and just distal to the expanded electrode have a tubular shape and are coated with a thermoplastic or thermoset insulative material 438. This process forms a fitting incorporating an expandable, collapsible electrode that does not change the inner diameter of the bypass graft during or after deployment.

Another important feature to thermally secure a fitting to a host vessel is the current density profile transmitted from an electrode to tissue. The configurations of the expandable retaining rings, previously discussed in FIGS. 5a–d and FIGS. 6a–d, make them more effective at thermally securing the retaining ring (electrode) and the bypass graft and fitting combination, to the vessel wall. These electrodes are designed with edges at the holes, notches, and slots cut in the ring. These holes, notches, and slots may be fabricated by laser drilling, EDM, milling, or other manufacturing process. Deposited electrodes, when used, may be applied in patterns that contain numerous edges. When radiofrequency energy is transmitted to these electrodes, the edges produce high current densities that locally heat the vessel wall. The small cross-sectional diameters of the conductive material forming the retaining rings ensures minimal depth of penetration, maintains focuses heating of the vessel wall, and helps to prevent damage to adjacent anatomy. In addition, the spaces defined by the electrode holes, notches, and slots provide a place for the vessel to shrink and coagulate. This increases the bond strength between the electrode and the vessel wall. The electrodes may additionally be covered with a porous material, such as collagen, fibrinogen, gelatin, and urethane, to further define a structure incorporating holes, notches, and slots for tissue to shrink and coagulate. The use of materials containing holes, notches and slots may also be used to encourage neointimal cell growth. Porous materials having a low melting point (e.g. 60° C.–120° C.) may be chosen to enhance thermal bonding between the bypass graft and host vessel wall. Heating such porous materials causes them to soften, reform and/or crosslink to coagulated tissue while heating the vessel wall with the electrodes.

As previously discussed, electrodes may also be incorporated in the end-to-side fittings. The electrode features described above which improve thermal securing may be incorporated in the petals or flared regions of the end-to-side fittings. These features are designed to increase contact between the electrode and the interior of the vessel wall, provide a structure to localize bonding between the vessel wall and the electrode, and insulate the electrodes from blood flow.

Figure 28A:
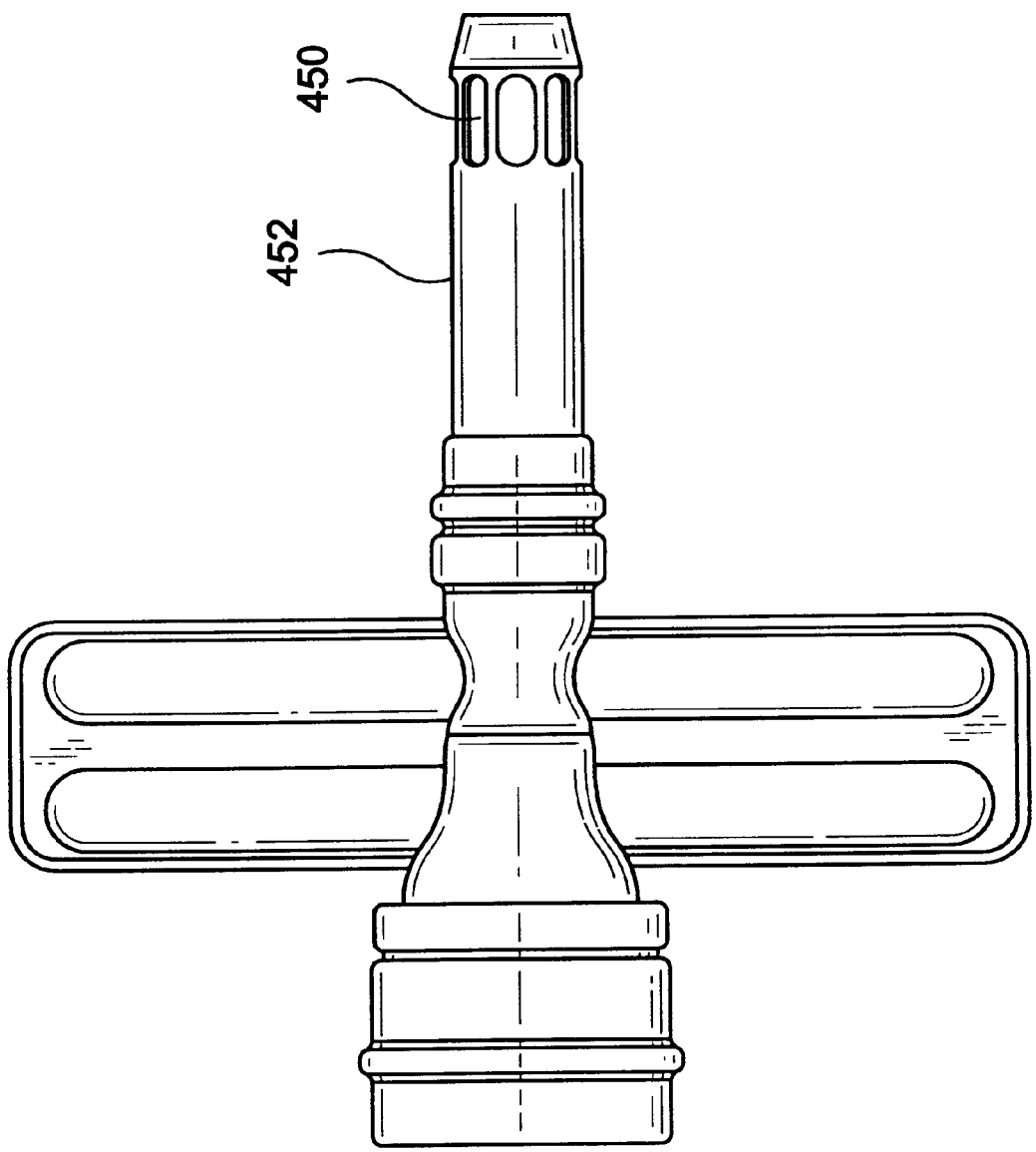
FIGS. 28a–b show tear-away sheath embodiments.
Figure 28B:
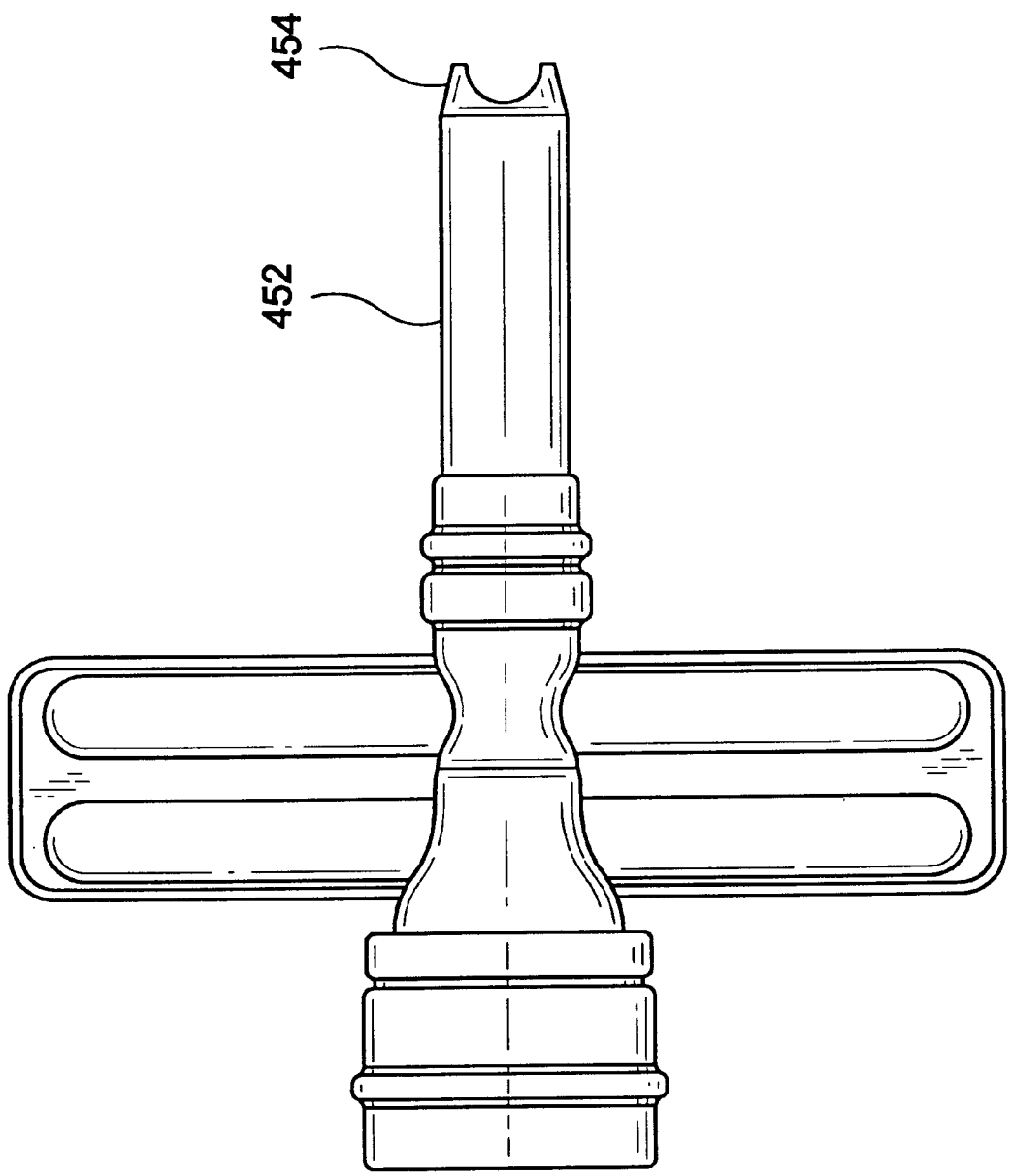

FIG. 28a shows cut-out areas 450 oriented along the tear-away sheath 452 and distributed radially around the sheath 452 that permit blood to flow through the cut-out areas in the sheath and past the distal lumen of the sheath. Alternative distributions and geometries for the cut-out areas may be chosen based on application and insertion requirements for the bypass graft. FIG. 28b shows a tear-away sheath incorporating an anchoring extension 454 at the distal end of the sheath. The extension 454 is designed to maintain access between the tear-away sheath and the host vessel when the sheath is positioned perpendicular to the host vessel. The length of the sheath should be limited to that required to access the interior of the host vessel while ensuring short bypass grafts may be inserted past the distal end of the sheath, especially when the bypass graft has been secured at the opposite end. To make the sheath suitable for less invasive access, a long side arm extension to the sheath may be incorporated to support the sheath during manipulations. The side arm should also permit splitting into two halves to remotely tear the sheath away from the bypass graft.

Figure 29:
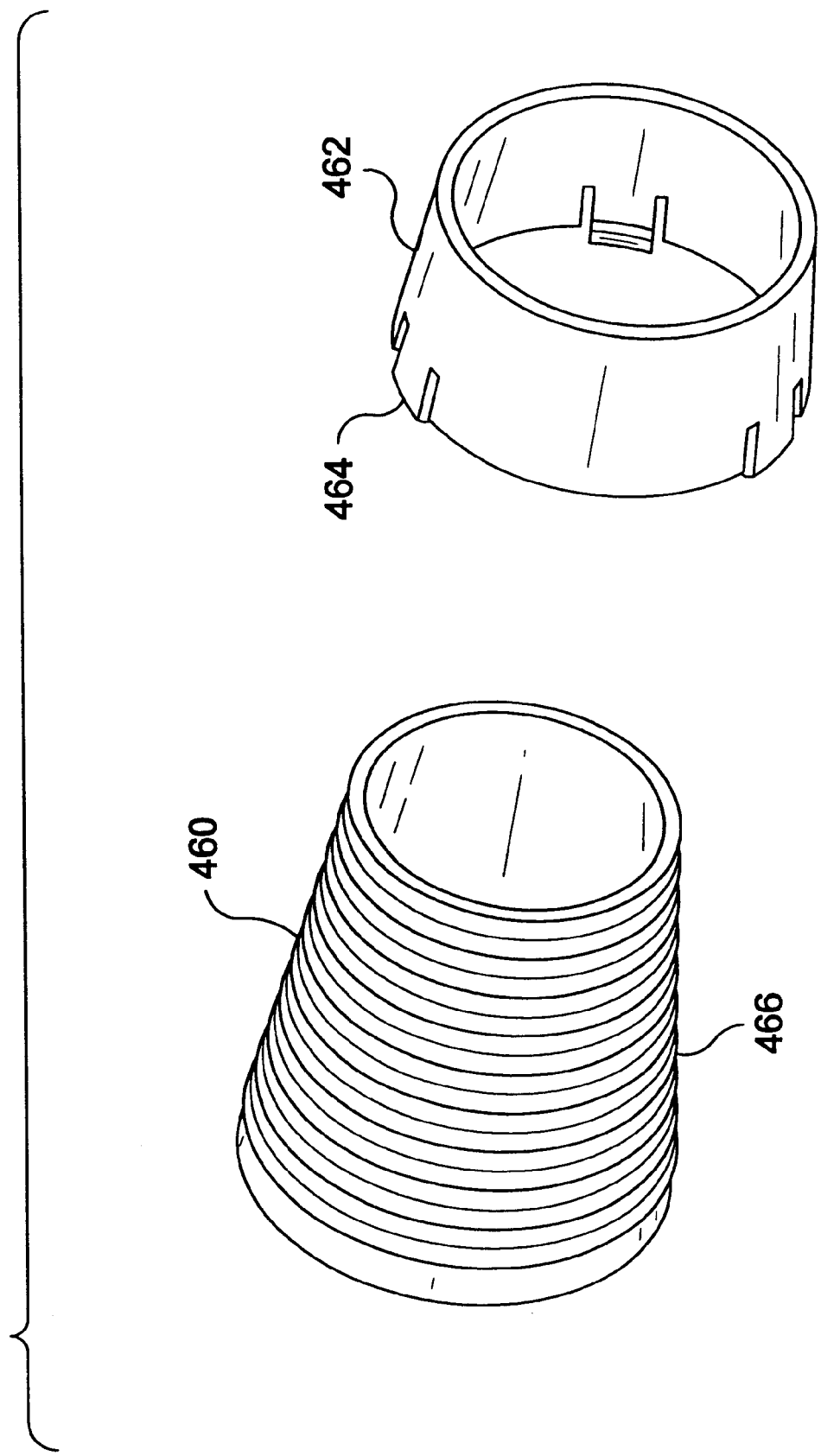
FIGS. 29 shows a fitting system.
Figure 30A:
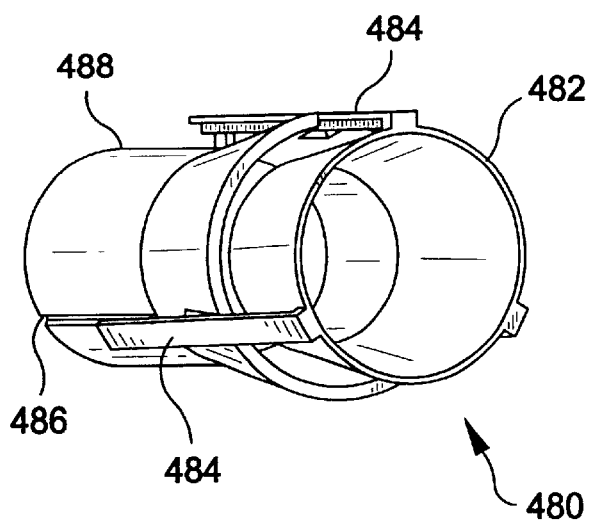
FIGS. 30a–d show other embodiments of a fitting system.
Figure 30B:
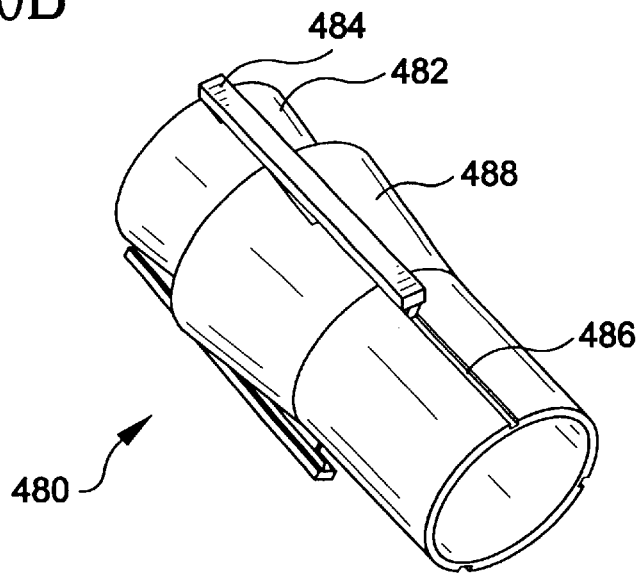
Figure 30C:
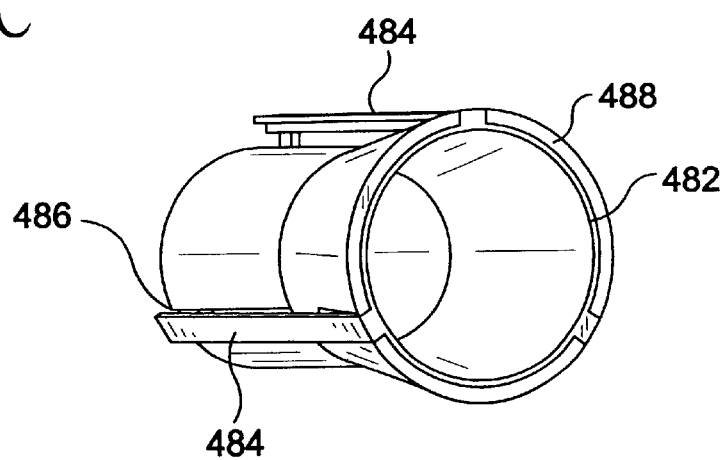
Figure 30D:
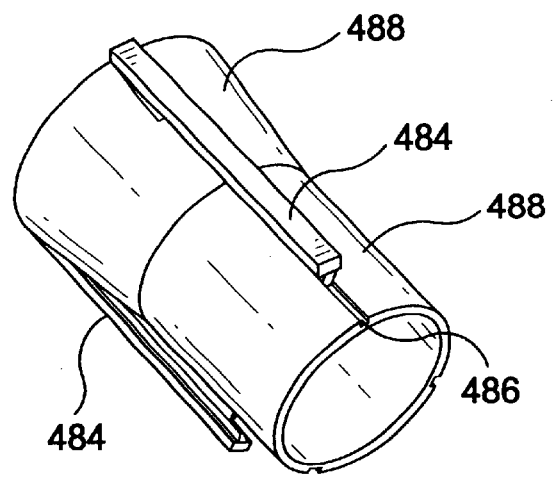
Figure 31D:
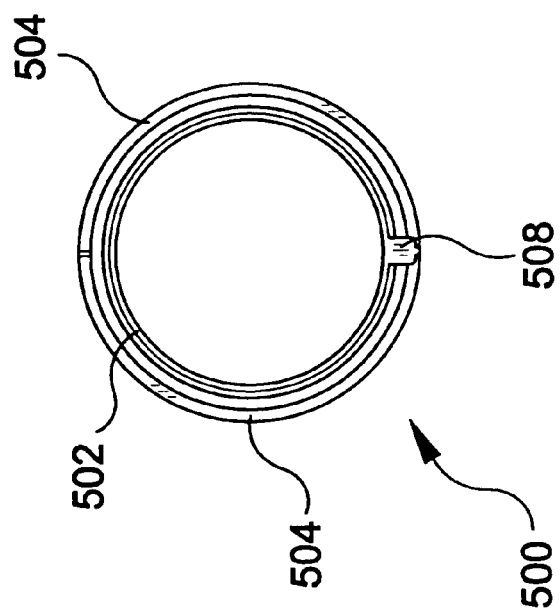
Figure 31C:
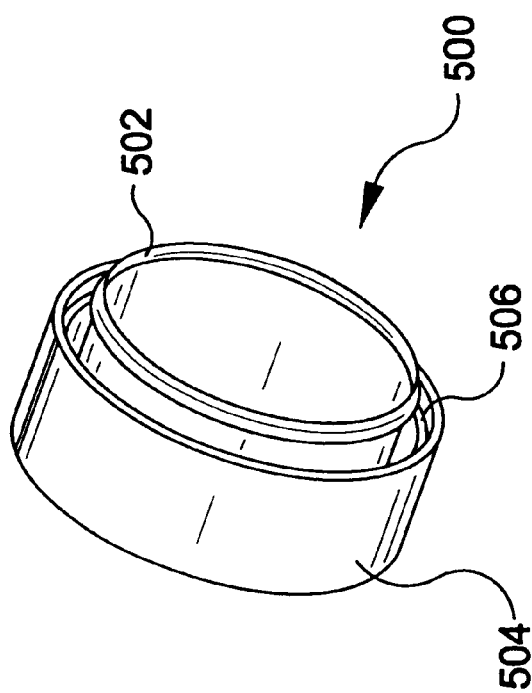

FIG. 29 shows a snap fitting 460 designed to facilitate bonding the bypass graft to the fitting. A distal piece 462 of the snap fitting incorporates extensions 464 designed to lock the distal piece 462 to mating teeth 466 of the proximal snap fitting piece 460. The proximal piece 460 is also tapered to accommodate a range of bypass graft diameters. The bypass graft is inserted through the proximal piece 460 and everted over the external surface of the proximal piece; alternatively, the bypass graft is positioned over the exterior surface of the proximal piece 460. Then, the distal piece 462 is advanced over the bypass graft and proximal piece interface, and is locked to the teeth thereby securing the bypass graft to the proximal piece 460. The distal piece 462 is configured for end-end anastomoses; however, it may be modified with features described below to accommodate end-side anastomoses. The bypass graft and snap fitting combination may be thermally secured to a host vessel by delivering radio frequency energy through the distal piece after placing the distal piece in contact with the vessel wall, as will be described below. Alternatively, an electrode secured to the proximal piece, or the proximal piece also functioning as the electrode may be used to thermally secure the host vessel to the bypass graft and snap fitting combination.

FIGS. 30a–d shows an alternative snap fitting 480. The distal and proximal pieces are integrated into one component. This adaptation facilitates manipulation of the bypass graft relative to the fitting since the operator only needs to hold the bypass graft and single fitting; otherwise, the operator needs to hold the proximal piece, distal piece, and bypass graft while securing the bypass graft to the fitting. The distal piece 482 contains locking hinges 484 designed to move axially along rails 486 incorporated in the proximal piece 488. The locking hinges 484 move along the rails 486 but are unable to be separated from the proximal piece 488. One way to accomplish this is by making the distal end of the locking hinges, positioned inside the rail openings, wider than the rail openings. The distal ends of the locking hinges also have extensions that mate and lock teeth incorporated in the rails of the snap fitting. In operation, the bypass graft is positioned through the open snap fitting and is secured by closing the snap fitting. With the snap fitting open, the bypass graft is inserted through the lumen of the proximal piece 488 and is advanced over the tapered end of the distal piece 482. Then, the snap fitting is closed by moving the proximal piece along the locking hinges of the distal piece thereby compressing the bypass graft between the proximal piece and distal piece. The ends of the locking hinges are secured to the mating teeth of the rails to secure the distal piece relative to the proximal piece. The distal piece 482 as shown is configured for end-end anastomoses; however, it may be modified with features described below to accommodate end-side anastomoses. As stated previously, the distal piece or proximal piece may function as electrodes to permit thermally securing the fitting to the vessel wall.

FIGS. 31a–d show an alternative snap fitting 500 that has a central piece 502 and a lockable outer piece 504. The outer piece is composed of a single cylindrical component or two distinct sections that are designed to pivot about a hinge 506; the hinge connects the central piece and the outer piece, using a tab 508, to facilitate manipulating the snap fitting and the bypass graft. With the snap fitting open, the bypass graft is fed over the central piece 502 from the side of the snap fitting not containing the tab 508 connecting the hinge 506 to the central piece. The tab 508 is located on one side of the central piece to facilitate advancing the bypass graft over the central piece without having to cut an incision through the distal end of the bypass graft. After the bypass graft has been positioned over the central piece, the outer piece is closed together compressing the bypass graft between the outer piece and the central piece. A locking mechanism is designed at the contacting ends of the outer piece and is configured to bond the outer piece in a closed, cylindrical position to reliably secure the bypass graft to the snap fitting. This may be achieved by incorporating mating teeth on opposite ends of the outer piece tailored to interlock when the ends overlap. The outer piece of this snap fitting embodiment may function as at least one electrode for thermally securing the fitting to the vessel wall.

Figure 32B:
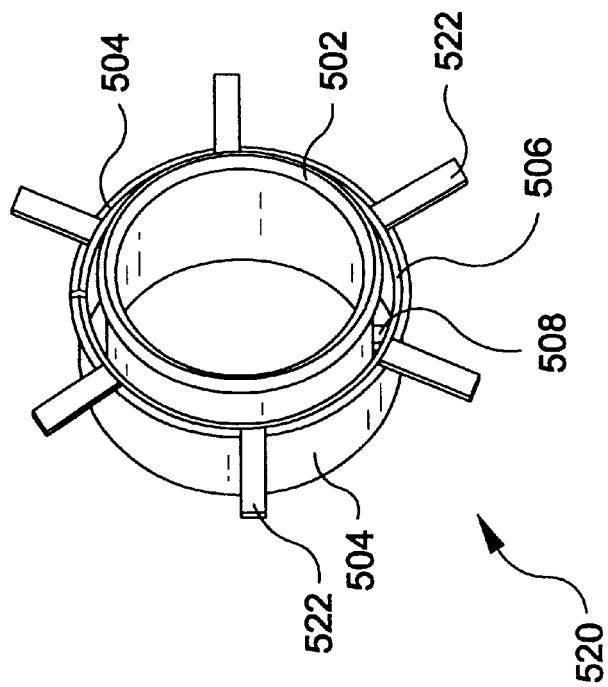
FIGS. 32a–b show other embodiments of a fitting system.
Figure 32A:
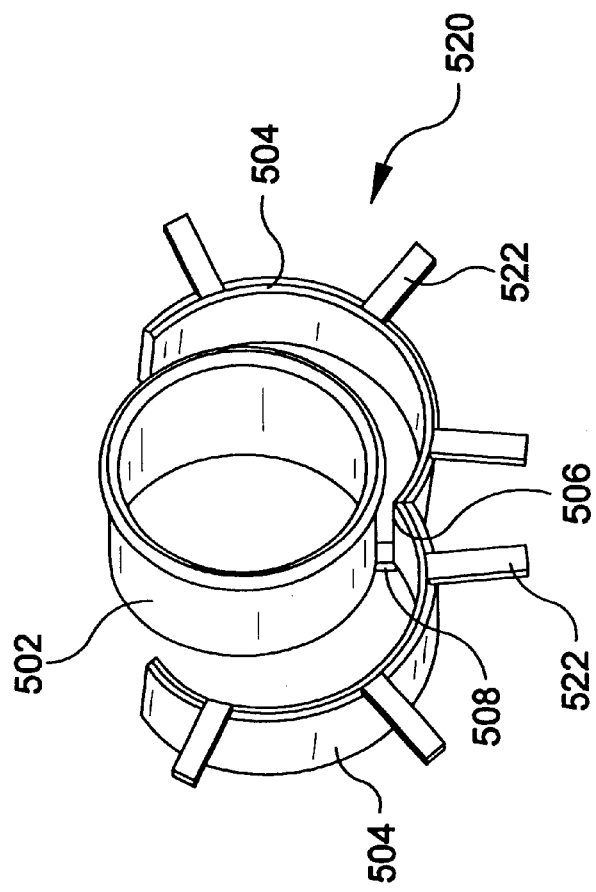

FIG. 32a–b show snap fitting 520 including petals 522 or other suitable modification. The fitting 520 may be used to produce end-side anastomoses. The petals 522 of the snap fitting 520 may function as at least one electrode for thermally securing the fitting to the vessel wall.

Experimental studies of thermal securing were conducted by positioning metallic fittings, into canine femoral arteries and veins during 3 experimental procedures. Signal wires were bonded to the metallic fittings and connected to a generator capable of delivering radiofrequency energy having a frequency of 500 kHz and a maximum power of 50 Watts. The generator was programmed to terminate radiofrequency energy delivery when impedance exceeded 300 $\Omega$, signaling completion of the thermal bond. Radiofrequency energy was delivered between each fitting and an indifferent ground patch electrode placed on the animals' thigh. Radiofrequency power ranged between 5 and 20 Watts for a duration of 5 to 60 seconds. The thermal anastomoses were acutely evaluated for leak resistance, patency, and tensile strength.

All bypass grafts were patent after thermal securing to the host vessel as evidenced by injection of contrast solution, visualized using fluoroscopy, demonstrating continuous blood flow through the bypass grafts. The thermal securing mechanism resisted leaking at the fitting to host vessel interface as demonstrated by hemostasis when the bypass graft was clamped thereby increasing the blood pressure at the anastomoses. The tensile strength of the thermal anastomoses reached 2 lbs. As a result, thermal securing was effective at bonding bypass grafts to host vessels producing end-to-end anastomoses exhibiting a fluid tight bypass graft to host vessel interface capable of withstanding pressures exerted in the vessel.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A bypass graft system comprising:
   a fitting defining an inner surface, an outer surface, at least two ends, and a compression mechanism adapted to attach a bypass graft to the fitting; and
   at least one electrode functionally connected to the fitting and an energy source;
   wherein the energy source is adapted to transmit energy to the electrode and cause functionally adjacent regions of tissue to rise in temperature.

2. A bypass graft system comprising:
   a fitting defining an inner surface, an outer surface, at least two ends, and a compression mechanism adapted to attach the bypass graft to the fitting;
   a sheath adapted for insertion through a puncture in a vessel wall and including a lumen for passing the bypass graft and fitting into the vessel interiors, the sheath adapted to split in two or more pieces for removal from around the bypass graft; and
   at least one electrode connected to the fitting and to an energy source;
   wherein the energy source is adapted to transmit electrical current to the electrode and cause thermal excitation of an adjacent region of tissue.

3. A system for securing a graft comprising;
   a tubular structure having at least two ends, an inner surface, and an outer surface;
   a first fitting attached to one end of the tubular structure and having a cross-section that substantially matches the cross-section of the tubular structure;

a second fitting attached to the other end of the tubular structure and having a cross-section that substantially matches the cross-section of the tubular structure;

a delivery mechanism adapted to access the lumen of the vessel and adapted to hold the lumen in an expanded orientation, the delivery mechanism adapted to functionally cooperate with the fittings and tubular structure in order for the fittings and tubular structure to be inserted through an opening established in the vessel;

at least one first electrode associated with the first fitting adapted to thermally secure the first fitting to a vessel at the one location; and at least one second electrode associated with the second fitting adapted to thermally secure the second fitting to the vessel at a second location.

4. The system of claim 3 wherein the fitting further includes more than two ends and a first electrode is bonded to one end; and the bypass graft attached to the fitting at one end;

wherein the first electrode and second electrode are adapted to thermally secure the fitting to the vessel at one or more ends.

5. A bypass graft system comprising:

a fitting attached to a bypass graft, the fitting including a flared distal end and at least one electrode associated with the flared distal end, the at least one electrode adapted to thermally secure the fitting to a vessel wall.

6. A bypass graft reinforcing structure comprising;

a tubular structure with an inner surface, outer surface, and two ends;

a first fitting attached to the tubular structure at one end;

a first compression mechanism adapted to secure a bypass graft to the first fitting;

a first electrode associated with the first fitting, the first electrode adapted to thermally secure the bypass graft and the tubular structure at one end;

a second fitting attached to the tubular structure at one end;

a second compression mechanism adapted to secure the bypass graft to the second fitting; and a second electrode associated with the second fitting, the second fitting adapted to thermally secure the bypass graft and the tubular structure at the second end.

7. A bypass graft system comprising:

at least one fitting defining an outer surface, an inner surface and at least two ends;

at least one compression mechanism adapted to attach a graft to the at least one fitting;

at least one electrode associated with the at least one fitting, the at least one electrode adapted to transmit thermal energy to at least a region of tissue;

at least one current carrying member attached to the at least one electrode and adapted to be separated from the at least one electrode; and a generator connected to the at least one current carrying mechanism, the generator adapted to transmit an electrical current to the at least one electrode and cause a region of tissue adjacent the at least one electrode to rise in temperature and become secured to one or more members or body regions.

* * * * *